United States Patent
Hastings

(10) Patent No.: US 7,301,451 B2
(45) Date of Patent: Nov. 27, 2007

(54) NOTIFICATION ALARM TRANSFER METHODS, SYSTEM, AND DEVICE

(75) Inventor: David C. Hastings, Rancho Santa Margarita, CA (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 464 days.

(21) Appl. No.: 10/750,493

(22) Filed: Dec. 31, 2003

(65) Prior Publication Data

US 2005/0151640 A1    Jul. 14, 2005

(51) Int. Cl.
G08B 1/08    (2006.01)

(52) U.S. Cl. ............... 340/539.12; 340/539.1; 340/539.11; 340/531; 340/573.1; 128/903; 128/904; 600/300; 600/301

(58) Field of Classification Search ............ 340/573.1, 340/573.4, 539.1, 539.11, 539.12, 539.19, 340/531, 5.8; 128/903, 904; 600/300, 301; 607/32, 60; 705/2, 3
See application file for complete search history.

(56) References Cited

U.S. PATENT DOCUMENTS

| | | | |
|---|---|---|---|
| 5,003,984 A | | 4/1991 | Muraki et al. |
| 5,446,678 A | | 8/1995 | Saltzstein et al. |
| 5,452,356 A | | 9/1995 | Albert |
| 5,481,255 A | | 1/1996 | Albert et al. |
| 5,735,285 A | | 4/1998 | Albert et al. |
| 6,057,758 A | * | 5/2000 | Dempsey et al. ...... 340/539.12 |
| 6,097,308 A | | 8/2000 | Albert et al. |
| 6,198,394 B1 | * | 3/2001 | Jacobsen et al. ......... 340/573.1 |
| 6,264,614 B1 | | 7/2001 | Albert et al. |
| 6,579,231 B1 | * | 6/2003 | Phipps ............... 600/300 |
| 6,602,191 B2 | * | 8/2003 | Quy ............... 600/300 |
| 6,749,566 B2 | * | 6/2004 | Russ ............... 600/300 |
| 2002/0183976 A1 | * | 12/2002 | Pearce | |
| 2003/0045279 A1 | | 3/2003 | Shostak | |

FOREIGN PATENT DOCUMENTS

WO    WO 03/021990 A1    3/2003

OTHER PUBLICATIONS

Vocera Communications System, Wearable Instant Voice Communication, 2003, Vocera Communications, Inc., Cupertino, CA, USA.

(Continued)

Primary Examiner—Hung Nguyen
(74) Attorney, Agent, or Firm—Andrus, Sceales, Starke & Sawall, LLP

(57) ABSTRACT

A method for transferring data may include receiving data from a monitoring device, determining whether the subject being monitored has a condition that may require attention, and sending a notification message to a portable electronic device that is designed to be carried by a caregiver if such a condition exists. The notification message may be sent using one or both of a first wireless data transfer method and a second wireless data transfer method. The system may use both methods to communicate with one device or may use the first method to communicate with a first device and the second method to communicate with a second device. The portable electronic device may include two wireless transceivers such as a transceiver designed to connect the device to a local area network of a facility and a transceiver designed to connect the device to a cellular network.

45 Claims, 16 Drawing Sheets

OTHER PUBLICATIONS

Mobile Pro 900 Handheld PC, 2003, NEC Solutions (America), Inc., Santa Clara, CA, USA.
PPT 8800 Series With Windows, Mobile 2003 Software for Pocket PCs, 2002, pp. 1-4, Symbol Technologies, www.symbol.com/ppt8800.
MiniScan Series, Miniature, High-Performance Scan Modules, 2003, Symbol Technologies, Inc., www.symbol.com/oem.
PSM201, Bar Code Scanning Module for Motorola, IDEN Phones, 2003, Symbol Technologies, Inc., USA.
StatView Alarm Notification System, 2001, General Electric Company, USA.
StatView RespondNow, 2003, General Electric Company, USA.
StatView RespondNow, 2002, General Electric Company, USA.
IBM & Citizen Watch develop Linux-based "WatchPad", Oct. 11, 2001, pp. 1-4, DeviceForge LLC, LinuxDevices.com.
Overview, HP iPAQ Pocket PC h5500 Series, 2003, pp. 1-9, Hewlett-Packard Development Company, L.P., http://www.hp.com/go/iPAQ.
hp iPAQ h4355 pocket pc (FA173A#ABA) 1994-2003, pp. 1-2, Hewlett-Packard Company, http://www.shopping.hp.com/cgi-bin/hpdirect/shopping/scripts/pro....
Biometrics in the real world, AuthenTec, Inc., pp. 1-2, Dec. 3, 2003, http://www.authentec.com/finallnteg/WhyTruePrint.htm.
AT&T Wireless, our biggest store: phones, Nokia 3300, 2003, pp. 1-3, AT&T Wireless, http://www.attwireless.com/personal/products/phonedetails.jhtml?i....
Aloysius Choong, HP's Biometric PDA, Dec. 10, 2002, pp. 1-3, CNET Networks, Inc., http://www.zdnet.com.au/reviews/coolgear/pda/story/0,20000235....
AT&T Wireless, our biggest store: phones, Sony Ericsson P800, 2003, pp. 1-3, AT&T Wireless, http://www.attwireless.com/personal/products/phonedetails.jhtml?i....
Microban Protection, Dec. 8, 2003, pp. 1-3, Microban Products Company, Huntersville, NC, http://www.ca-innovations.com/smartfeatures.asp?page=microban....
Plastic fabrics: Keeping prices down as material costs go up, Jul. 7, 2003, pp. 1-4, Trade Media Holdings Ltd, http://www.trimmings.globalsources.com/am/article_id/900000004....
Raised toilet seats, Dec. 8, 2003, pp. 1-3, Gordon Ellis & Co., UK.
Linux on a wrist watch, Nov. 1, 2001, p. 1 of 1, Linus Torvalds, http://www.research.ibm.com/WearableComputing/factsheet.html.
MWS antibacterial/anti-mold chain, 1997-2003, pp. 1-3, Tsubakimoto Chain Co, http://tsubakimoto.com/products/chain/conveyor_chain/mws_antib....
Universal Display Corporation, Product Concepts, 2001-03, p. 1 of 1, Universal Display Corporation, http://www.universaldisplay.com/concepts.php.
Universal Display Corporation, Technology, High Efficiency Materials, 2001-03, p. 1 of 1, Universal Display Corporation, http://www.universaldisplay.com/high.php.
Universal Display Corporation, Technology, SOLED Stacked Organic Light Emitting Device, 2001-03, pp. 1-2, Universal Display Corporation, http://www.universaldisplay.com/soled.php.
Universal Display Corporation, Technology, TOLED Transparent Organic Light Emitting Device, 2001-03, pp. 1-2, Universal Display Corporation, http://www.universaldisplay.com/toled.php.
Universal Display Corporation, Technology, FOLED Flexible Organic Light Emitting Device, 2001-03, pp. 1-2, Universal Display Corporation, http://www.universaldisplay.com/foled.php.
Universal Display Corporation, OLED Technology, 2001-03, pp. 1-2, Universal Display Corporation, http://www.universaldisplay.com/tech.php.
The Changing Display Industry: CRT and Flat Panel, Jan. 2002, pp. 1-12, Business Communications Co., http://www.mindbranch.com/catalog/product.jsp?code=R2-540.
Leslie Versweyveld, eMagin Supplies OLED Displays as 3D Imaging Source for VRmagic Surgical Training Simulator, Sep. 24, 2003, pp. 1-4, http://www.hoise.com/vmw/03/articles/vmw/LV-VM-10-03-26.html.
BlackBerry 7280 Wireless Handheld, Dec. 3, 2003, p. 1 of 1, http://www.blackberry.net/products/blackberry7200/blackberry728....
RIM 950 Wireless Handheld, Dec. 3, 2003, 2003, Research In Motion Limited, http://www.blackberry.net/products/handhelds/rim950.shtml.
Blackberry 5810 Wireless Handheld, 2003, p. 1 of 1, Research In Motion Limited, http://www.blackberry.net/products/blackberry5810/index.shtml.
RIM 850 Wireless Handheld and RIM 950 Wireless Handheld, 2003, p. 1 of 1, Research In Motion Limited, http://www.blackberry.net/products/rim850_950/index.shtml.
AuthenTec, Inc., Fingerprint Sensors using TruePrint, Technology for Convenient Security, 2003, p. 1 of 1, AuthenTec, Inc., http://www.authentec.com.
2002 BiometriTech Product Of The Year Winners, 1997-2003, pp. 1-10, Technology Marketing Corporation, Norwalk, CT, http://www.biometritech.com/features/poty03.htm.

* cited by examiner

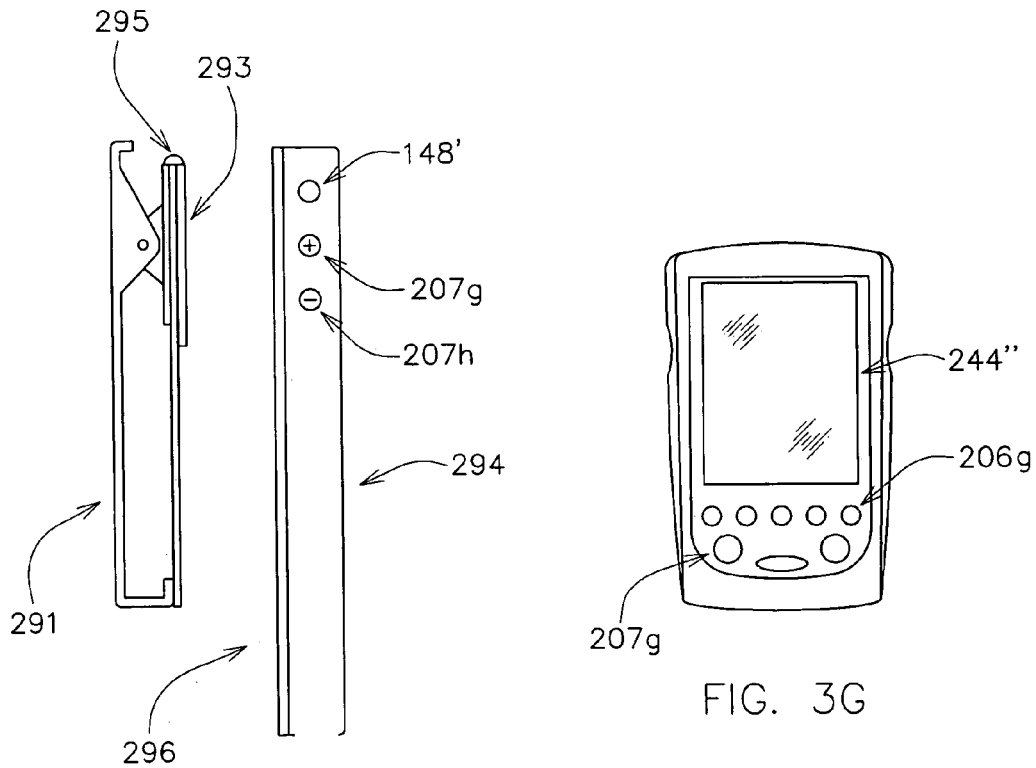
FIG. 3F
FIG. 3G
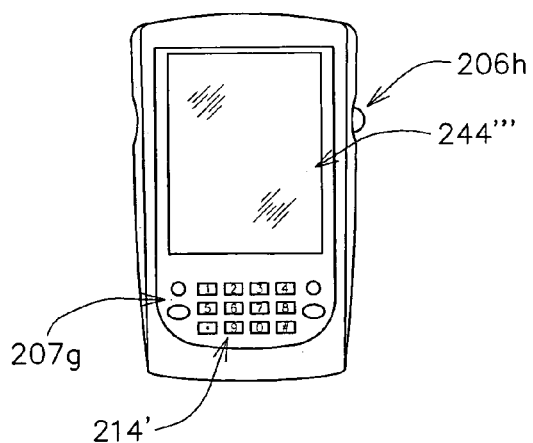
FIG. 3H
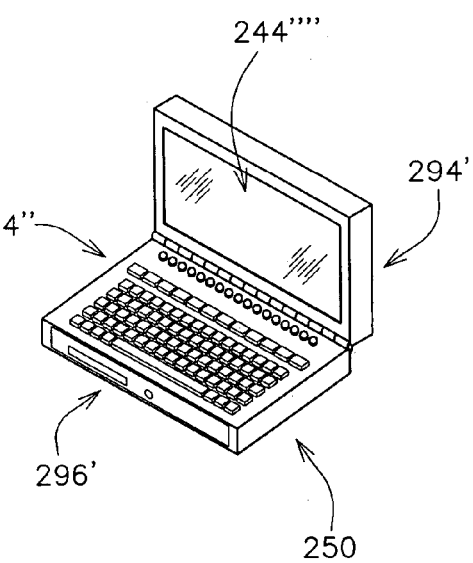
FIG. 3I

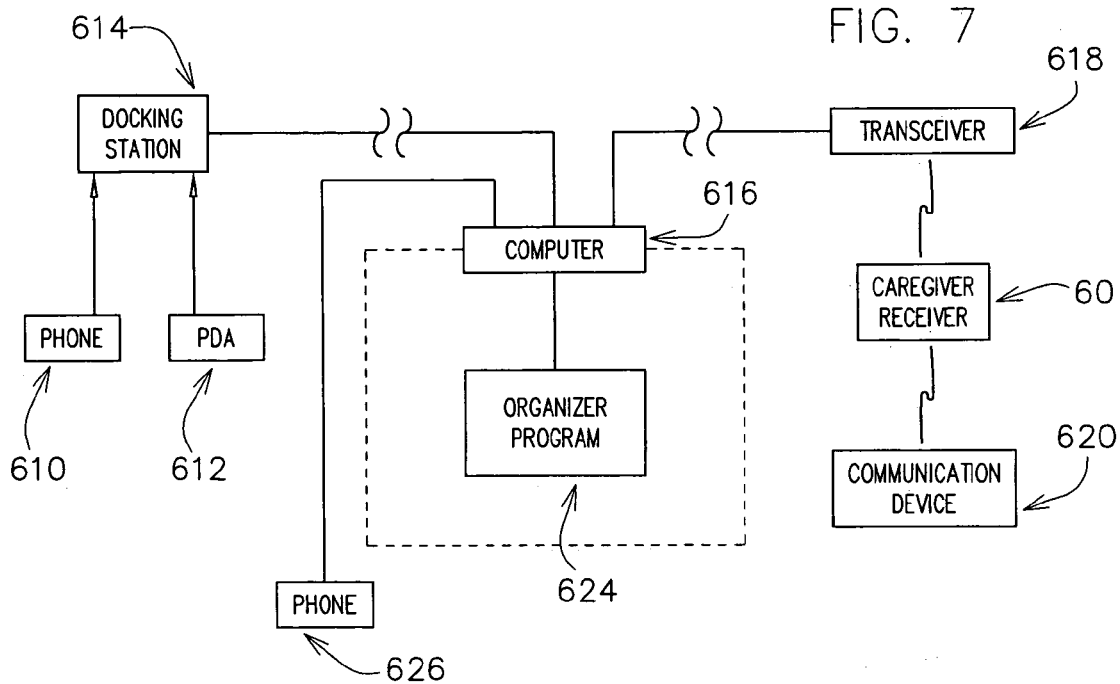
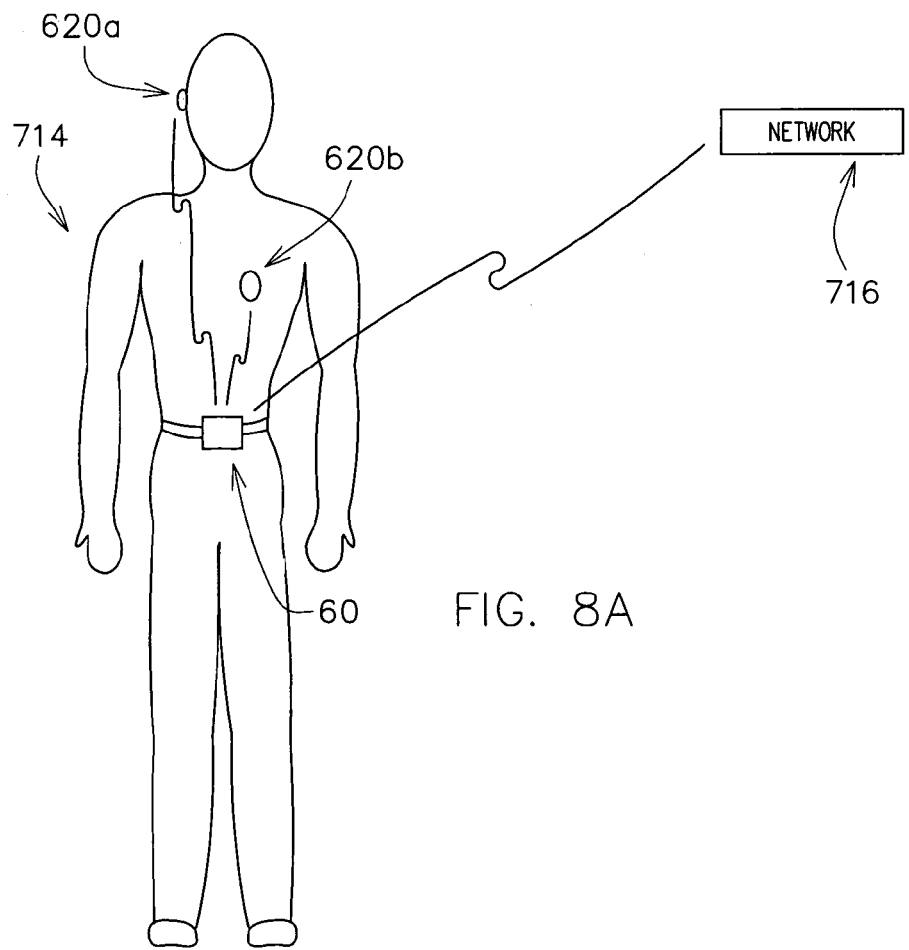

FIG. 11A

| Name | Receiver Number | Unit | Pendant Id | Options | | | |
|---|---|---|---|---|---|---|---|
| Caregiver_3 | 0020126 | LAB1 | eeddcc | [Send Page] | [Change Name] | [Patient Assignment] | [Schedules] |
| Caregiver_2 | 0020125 | LAB1 | aabbcc | [Send Page] | [Change Name] | [Patient Assignment] | [Schedules] |
| Caregiver_1 | 0020123 | LAB1 | abcdef | [Send Page] | [Change Name] | [Patient Assignment] | [Schedules] |
| Everyone | 0000009 | LAB1 | | [Send Page] | | | |
| Group_1 | | LAB1 | | [Send Page] | [Change Name] | [Patient Assignment] | |

PATIENTS  CAREGIVERS     UNIT: LAB1     Caregiver Administration
[Caregiver Setup (Add/Remove)] [Clear Assignments For All Caregivers] [Group Setup]

FIG. 11B

PATIENTS  CAREGIVERS     Caregiver Setup
[Add Caregiver]

| Name | Receiver Number | Unit | Pendant Id | Options | |
|---|---|---|---|---|---|
| Caregiver_1 | 0020123 | LAB1 | abcdef | [Remove] | [Edit] |
| Caregiver_2 | 0020125 | LAB1 | aabbcc | [Remove] | [Edit] |
| Caregiver_3 | 0020126 | LAB1 | eeccdd | [Remove] | [Edit] |

FIG. 11C

PATIENTS  CAREGIVERS     UNIT: LAB1     Add Caregiver

Name: [Jane Wilson] (Required. Can be a maximum of 20 characters)
Receiver Id: [1234567]
Unit: [LAB1]
Pendant Id: [aabbcc] (Optional. Must be 5 characters)
[Add] [Reset]
[Back to Caregiver Setup][Back to Caregiver Administration]
[Set Info for Caregiver]

Groups

Available Groups
LAB1 All
Nurse Manager LAB1
Nurse Manager All
Cardiac Care

[Assign]

NOTIFICATION ALARM TRANSFER METHODS, SYSTEM, AND DEVICE

BACKGROUND

Hospitals and clinics that offer sophisticated patient care typically have a patient monitoring system that collects and reports patient health information such as vital signs, cardiac assessment, and carbon dioxide output, along with other information. Patient monitoring systems are available from a variety of vendors and collect and display the patient health information in a variety of ways and may use both wired and Wireless approaches to collect and distribute data. For example, a patient monitoring system may be utilized in conjunction with a Wireless telemetry system that collects and transmits data to the patient monitoring system for handling and reporting.

The patient monitoring system analyzes the data of the one or more patients being monitored and sends an alarm when a particular patient parameter triggers an alarm criterion. In some facilities, an alarm notification system may be used in conjunction with the patient monitoring system to notify caregivers (such as nurses) of such alarms. The alarm notification system monitors the patient monitoring system for alarms and notifies appropriate caregivers of the alarms when they occur.

Alarm notification systems are typically used in conjunction with a paging network to distribute alarm information to caregivers. Caregivers are assigned a receiver that receives the alarm information and may also include a transmitter used to send information to the alarm notification system. The alarm notification system is typically treated as a secondary alarm system in that it distributes alarm information to caregivers but is not utilized to actually acknowledge and reset patient monitoring system alarms. The alarm notification system may or may not be made by the same vendor as the patient monitoring system and accordingly, some alarm notification systems are configured to collect and distribute alarm information from patient monitoring systems made by various vendors and using various data transfer protocols.

Depending on the level of sophistication of the alarm notification system, the system may be able to transmit various types of information to the receivers carried by caregivers. The caregiver receivers may have graphical capability in addition to text display capability and the alarm notification system may transmit graphical information such as a snippet of an electrocardiogram (ECG) waveform collected at about the time of the alarm, which waveform may be displayed on the receiver.

The distribution of alarm information, such as the particular caregivers that are sent alarms and the frequency of such pages, may be configured in various ways on different alarm notification systems. The system may send reminder pages when an initial alarm notification has not been acknowledged and status pages that provide patient health information to one or more caregivers during pre-set intervals.

While conventional alarm notification systems provide several advantageous features for use by hospitals and clinics, especially in conjunction with patient monitoring systems, there are several challenges with respect to the conventional systems that new features and designs may address.

As technology provides caregivers with an ever increasing array of devices used to aid in patient care, caregivers, especially nurses, are asked to carry an increasing number of electronic devices in the workplace. One such device is the receiver associated with an alarm notification system. It would be advantageous if the alarm notification receiver functionality was capable of being added to a caregiver's set of tools without adding to the burden of the caregiver.

A caregiver or technician is typically required to reset a patient monitoring system alarm at either the bedside or a central monitoring station. This configuration is not ideal because the caregivers who are able to recognize and respond to alarms, and reset those alarms if proper, are not typically at the patient's bedside or the central monitoring station. Accordingly, it would be advantageous to have a system that provides a caregiver more flexibility in responding to alarms.

Currently, certain sophisticated alarm notification systems provide a snippet of an ECG waveform (typically six to nine seconds of data acquired at about the same time as the alarm was triggered) to the caregiver receiver such that a caregiver in the field may assess the waveform upon the receipt of an alarm notification to determine the proper action. A typical approach to sending the waveform data is to send a several second waveform gathered at the time the associated alarm was received. There are some instances when more and/or different information may be desirable. It would be desirable to have a notification system capable of providing a caregiver with more information when needed.

Conventional alarm notification systems may offer bi-directional communication capability, thus permitting the caregiver to acknowledge an alarm. A receiver with more sophisticated communication capabilities would be desirable.

Alarm notification system receivers do not typically have a great deal of onboard computer memory, in an effort to reduce the size, complexity, and expense of the receiver. A system that compensates for this small memory capacity would be beneficial.

In alarm notification systems having a large number of caregiver receivers, one design challenge is determining how to associate the individual receivers with particular caregivers in an efficient manner. A system capable of associating a receiver with a caregiver in an efficient manner would be beneficial.

Another design challenge presented by conventional alarm notification systems relates to the paging methodology. In many cases, an alarm notification system page may be sent to an individual caregiver when an alarm is received in the patient monitoring system. A system that could more efficiently send out pages to appropriate caregivers would be beneficial.

The teachings hereinbelow extend to those embodiments that fall within the scope of the appended claims, regardless of whether they accomplish one or more of the above-mentioned needs.

SUMMARY

One aspect relates to a notification system having a caregiver receiver with improved functionality. The caregiver receiver may serve as a PDA, a phone, and/or a wireless subject identification device. The wireless subject identification device may include components of a barcode scanner and/or an RFID transceiver circuit.

Another aspect relates to a notification system having a caregiver receiver with improved data transfer capabilities. The caregiver receiver according to this aspect may include the ability to communicate with a system point-to-point, over a healthcare network, over a cellular network, with a long-range transceiver, with a medium range transceiver, and/or with a short range transceiver. The caregiver receiver according to this embodiment may be configured to transfer data using more than one type of wireless data transfer protocol.

Another aspect relates to a notification system having increased data sharing capabilities. A system according to this aspect may be configured such that data may be shared between caregiver receivers.

Another aspect relates to a notification system with additional alarm enunciator options. A system according to this aspect may be configured such that a caregiver receiver may serve as a primary enunciator. The caregiver receiver may serve as a primary enunciator in all circumstances or may only serve as a primary enunciator in limited circumstances.

Another aspect relates to a notification system capable of providing additional information to a caregiver receiver. The additional information may be patient medical records (or portions thereof) or may be live waveform data. The live waveform data may be received from various sensors including ECG, cardiac output, and SpO2 sensors.

Another aspect relates to enabling voice communication in a hospital system. Voice communication may occur using a number of different protocols. The system may be configured to allow a user to control and use a personal wireless phone with a caregiver receiver. The system may be configured to automatically adjust contact numbers based on staffing changes and/or assignment changes. The system may be configured to automatically forward alarm data sent to a caregiver receiver when a call is placed using the caregiver receiver while the alarm data is being displayed on the caregiver receiver.

Another aspect relates to a transparent data retrieval process. Memory in a caregiver receiver may be used more efficiently according to this aspect since data may be transferred between the caregiver receiver and a remote storage device with little or no lag noticeable by a user.

Another aspect relates to alarm acknowledgement techniques. According to one method a user silencing an alarm may be identified based on voice recognition. According to one method, a user may be identified based on a biometric input such as a fingerprint identification. Based on the identity of the user, a determination can be made as to whether further actions are necessary to acknowledge the alarm. Identifying a user may occur before or after the notification is sent.

Another aspect relates to alarm paging sequences. Alarms may be sent to pre-selected groups which are a subset of the globally available users if an alarm is not answered initially (for instance based on affiliation with a team), to users based on characteristics of the user (location, job title, etc.), or based on other criteria.

Another aspect is directed to using an OLED as a display in a portable medical device. The OLED display may be controlled by a transistor array formed on a plastic substrate. The OLED display may be flexible and may be designed to be in a roll when not in use.

Another aspect relates to a ruggedized caregiver receiver. The caregiver receiver is preferably ruggedized such that it can withstand tough environments for which it is intended, such as use by an active caregiver.

Another aspect relates to protecting the caregiver receiver from bacterial growth. This may be done by providing a housing that is resistant to bacterial growth and/or may be done by providing a housing that is resilient to an antibacterial solution to be applied to the housing.

Another aspect relates to tracking a user using a signal transmitted by a caregiver receiver. The location of the caregiver determined in this manner can be used as an input and/or control for any number of applications of a hospital-based system.

Another aspect relates to ensuring that a caregiver receiver may implement a notification program with sufficient quickness. This may be accomplished by excluding implementation of programs unrelated to the care of patients. This may also be accomplished by monitoring an amount of processing power being used by programs on the caregiver receiver.

Another aspect relates to receiving positive acknowledgment that a page has been received by a particular caregiver or set of caregivers without requiring a manual response by the caregiver. This may be accomplished by any number of methods. For instance, this may aspect include using a system that allows an acknowledgement of a response to be sent without user intervention and/or may include sensors which allow a determination to be made regarding whether a user has viewed the message.

A system according to the claims may incorporate one or more aspects of a system according to the disclosure. Further, additional novel aspects may be evident from the description of the exemplary embodiments and from the appended claims such that a claim does not incorporate one of the above-listed aspects. Further still, many of these aspects may have application outside the field of medicine such as other portable electronic devices and/or other monitoring systems.

One embodiment is directed to a portable electronic device including a receiver configured to receive wireless signals, a transmitter configured to transmit wireless signals, and an acoustic sensor configured to receive user audio inputs. The portable electronic device further comprises a processing circuit configured to control an alarm to notify a user of a condition of a patient requiring attention in response to signals from the receiver, to process signals representative of an identity of an object of interest, and to process data representative of user audible inputs received from the acoustic sensor to be transferred wirelessly across a network by the transmitter. The device also includes a speaker coupled to the processing circuit and a display coupled to the processing circuit. The device may also include a housing configured to carry the receiver, the transmitter, the acoustic sensor, the speaker, the display, and the processing circuit and which is configured to be portable by a user.

Another embodiment provides a portable electronic device for use in a medical monitoring system that generates notification messages indicating that a patient being monitored may have a condition that requires attention and wirelessly transfers the notification messages to the portable electronic device. The portable electronic device includes a processing circuit configured to receive the notification messages indicating that the patient being monitored may have a condition that requires attention, and an identification device coupled to the processing circuit and configured to input data representative of an identity of a subject of interest from an information source at a distance from the identification device.

Another embodiment relates to a portable electronic device for use in a medical monitoring system that generates notification messages indicating that a patient being monitored may have a condition that requires attention and wirelessly transfers the notification messages to the portable electronic device. The portable electronic device includes, a wireless transceiver configured to receive the notification messages and a processing circuit configured to receive the notification messages from the wireless transceiver, send a control signal to alert a user to the receipt of the notification message, and implement an organizer function.

An additional embodiment is directed to a portable electronic device for use in a medical monitoring system that generates notification messages indicating that a patient being monitored may have a condition that requires attention and wirelessly transfers the notification messages to the portable electronic device. The portable electronic device includes an audio signal input, an audio signal output, a wireless transceiver configured to transfer data using a cellular protocol, and a processing circuit configured to receive the notification messages, generate a control signal to display physiological data associated with the notification message, and to facilitate transfer of voice data to the audio signal output and from the audio signal input by way of the wireless transceiver. Facilitating transfer of voice data may include initiating calls to other cellular devices and receiving calls from other cellular devices.

An additional embodiment provides a portable electronic device for use in a medical monitoring system that generates notification messages indicating that a patient being monitored may have a condition that requires attention and wirelessly transfers the notification messages to the portable electronic device. The portable electronic device includes an audio signal input, an audio signal output, a wireless transceiver, and a processing circuit. The processing circuit is configured to receive the notification messages indicating that the patient being monitored may have a condition that requires attention, send a control signal to alert a user to the receipt of the notification message, and implement an organizer function, and to facilitate transfer of voice data to the audio signal output and from the audio signal input by way of the wireless transceiver. The device also includes a barcode scanner coupled to the processing circuit.

An additional embodiment relates to a portable electronic device for use in a medical monitoring system that generates notification messages indicating that a patient being monitored may have a condition that requires attention and wirelessly transfers the notification messages to the portable electronic device. The portable electronic device includes an audio signal input, an audio signal output, a wireless transceiver, and a processing circuit. The processing circuit is configured to receive the notification messages indicating that the patient being monitored may have a condition that requires attention, send a control signal to alert a user to the receipt of the notification message, implement an organizer function, and to facilitate transfer of voice data to the audio signal output and from the audio signal input by way of the wireless transceiver. The device further includes a radio frequency circuit coupled to the processing circuit and configured to receive data comprising a code associated with an identity of a subject of interest.

Another embodiment is directed to an alarm notification system for use in a medical monitoring system configured to monitor a patient. The system includes a processing circuit configured to receive data indicating that the patient being monitored may have a condition that requires attention and to send notification messages based on the data indicating that the patient being monitored may have a condition that requires attention. The system also includes a portable electronic device comprising a processing circuit configured to receive the notification messages indicating that the patient being monitored may have a condition that requires attention; and an identification device coupled to the processing circuit and configured to input data representative of an identity of a subject of interest from an information source at a distance from the identification device.

Another embodiment provides a portable electronic device for use in a medical monitoring system that generates notification messages indicating that a patient being monitored may have a condition that requires attention and wirelessly transfers the notification messages to the portable electronic device. The portable electronic device includes a processing circuit configured to receive the data associated with the notification messages and a first wireless transceiver coupled to the processing circuit and configured to receive data associated with the notification messages and transfer at least some of the data to the processing circuit, the first wireless transceiver configured to operate using a first wireless data transfer method. The portable device also includes a second wireless transceiver coupled to the processing circuit and configured to receive data associated with the notification message and transfer at least some of the data to the processing circuit, the second wireless transceiver configured to operate using a second wireless data transfer method different than the first wireless data transfer method.

Another embodiment relates to a method to be implemented by electronic devices of a medical monitoring system of a health care facility where a patient's physiological characteristics are being monitored for conditions that may require attention by a clinician. The method includes receiving data from a monitoring device configured to monitor a patient, determining whether the patient has a condition that may require attention based on the data received from the monitoring device, sending a notification message to a portable electronic device using a first wireless data transfer method if the patient has a condition that may require attention, sending a notification message to the portable electronic device using a second wireless data transfer method different than the first wireless data transfer method if the patient has a condition that may require attention.

An additional embodiment is directed to a method to be implemented by electronic devices of a medical monitoring system of a health care facility where a patient's physiological characteristics are being monitored for conditions that may require attention by a clinician. The method includes receiving data from a monitoring device configured to monitor a patient, determining whether the patient has a condition that may require attention based on the data received from the monitoring device, sending a notification message to a first portable electronic device using a wireless data transfer method if the patient has a condition that may require attention, receiving a user input from a user input device, and sending data associated with the notification message, which data was received by the first portable electronic device, to a second portable electronic device based on the user input.

An additional embodiment provides a method to be implemented by electronic devices of a medical monitoring system of a health care facility where a patient's physiological characteristics are being monitored for conditions that may require attention by a clinician. The method includes receiving data from a monitoring device configured to monitor a patient, determining whether the patient has a condition that may require attention based on the data received from the monitoring device, sending a notification message to a first portable electronic device using a first wireless data transfer method if the patient has a condition that may require attention, and sending the notification message to a second portable electronic device using a second wireless data transfer method different than the first wireless data transfer method.

An additional embodiment relates to a portable electronic device for use in a medical monitoring system that generates notification messages indicating that a patient being monitored may have a condition that requires attention and wirelessly transfers the notification messages to the portable electronic device. The portable electronic device comprising, a processing circuit configured to receive the notification messages indicating that the patient being monitored may have a condition that requires attention, a first radio frequency wireless transceiver coupled to the processing circuit and configured to receive data associated with the notification message, the first wireless transceiver configured to operate using a first wireless data transfer method, and a second radio frequency wireless transceiver coupled to the processing circuit and configured to receive data associated with the notification message, the second wireless transceiver configured to operate using a second wireless data transfer method different than the first wireless data transfer method.

Another embodiment is directed to a portable electronic device for use in a medical monitoring system that generates notification messages indicating that a patient being monitored may have a condition that requires attention and wirelessly transfers the notification messages to the portable electronic device. The portable electronic device includes a processing circuit configured to receive the notification messages indicating that the patient being monitored may have a condition that requires attention, a first wireless transceiver coupled to the processing circuit and configured to receive data associated with the notification message, the first wireless transceiver configured to operate using a cellular data transfer protocol, and a second wireless transceiver coupled to the processing circuit and configured to receive data associated with the notification message, the second wireless transceiver configured to operate using a wireless local area network data transfer protocol.

Another embodiment provides a system for use in a medical monitoring system of a health care facility where a patient's physiological characteristics are being monitored for conditions that may require attention by a clinician. The system includes a first processing circuit configured to receive data from a monitoring device configured to monitor a patient, determine whether the patient has a condition that may require attention based on the data received from the monitoring device, generate a control signal to send a notification message to a portable electronic device using a first wireless data transfer method if the patient has a condition that may require attention, and generate a control signal to send a notification message to the portable electronic device using a second wireless data transfer method different than the first wireless data transfer method if the patient has a condition that may require attention, and the portable electronic device comprising a second processing circuit configured to receive data from a wireless signal comprising a notification message.

Another embodiment relates to a method for use in a medical monitoring system of a health care facility where a patient's physiological characteristics are being monitored for conditions that may require attention by a clinician. The method includes receiving a notification message indicating that the patient may have a condition that requires attention with a portable electronic device designed to be carried by the clinician, and receiving live physiologic data of the patient with the portable electronic device based on the notification message.

An additional embodiment is directed to a method for use in a medical monitoring system of a health care facility where a patient's physiological characteristics are being monitored for conditions that may require attention by a clinician. The method includes receiving a notification message indicating that the patient may have a condition that requires attention with a portable electronic device designed to be carried by the clinician, and receiving live physiologic data of the patient with the portable electronic device.

An additional embodiment provides a method for use in a medical monitoring system of a health care facility where a patient's physiological characteristics are being monitored for conditions that may require attention by a clinician. The method includes receiving live physiologic data of the patient with a portable electronic device, wherein the portable electronic device has a volume of less than about 60 cubic inches.

An additional embodiment relates to a method for use in a medical monitoring system of a health care facility. The method includes receiving physiologic data from sensors connected to a patient, processing the physiologic data from the sensors to identify a condition of the patient that may require attention by a clinician, sending a notification message to a portable electronic device designed to be carried by a clinician to indicate that the patient has a condition of the patient that may require attention by a clinician, and sending live physiologic data from the sensor to the portable electronic device based on a notification message sent to the portable electronic device.

Another embodiment is directed to a notification system for use in a medical monitoring system of a health care facility. The system includes a portable electronic device configured to receive notification messages and designed to be carried by a clinician, and a processing circuit configured to receive data from monitoring devices that are monitoring patients, generate a control signal to send a notification message to the portable electronic device to indicate that the patient has a condition that may require attention by a clinician based on the data received from the monitoring devices, and generate a control signal to send live physiologic data, relating to the notification message, acquired from one or more monitoring devices to the portable electronic device.

Another embodiment provides a portable electronic device for use in a medical monitoring system of a health care facility that generates notification messages indicating that a patient being monitored may have a condition that requires attention and wirelessly transfers the notification messages to the portable electronic device. The portable electronic device includes an audio signal input device, an audio signal output device, a wireless transceiver, and a processing circuit. The processing circuit is configured to receive the notification messages indicating that the patient being monitored may have a condition that requires attention and to facilitate transfer of voice data to the audio signal output and from the audio signal input by way of the wireless transceiver.

An additional embodiment is directed to a system for establishing voice communication in a health care facility having a monitoring system that generates notification messages indicating that a patient being monitored may have a condition that requires attention and wirelessly transfers the notification messages to portable electronic devices. The system includes a portable electronic device comprising an audio signal input device, an audio signal output device, a wireless transceiver, and a processing circuit configured to receive the notification messages indicating that the patient being monitored may have a condition that requires attention and to facilitate transfer of voice data to the audio signal output and from the audio signal input by way of the wireless transceiver. The system also includes a second processing circuit configured to receive voice data sent from the portable electronic device and facilitate transfer of the voice data to a recipient.

An additional embodiment provides a method to be implemented by electronic devices of a medical monitoring system of a health care facility where a patient's physiological characteristics are being monitored for conditions that may require attention by a clinician. The method includes receiving data from a monitoring device configured to monitor a patient, determining whether the patient has a condition that may require attention based on the data received from the monitoring device, sending a notification message to a portable electronic device if the patient has a condition that may require attention, and wirelessly transferring voice data received from the portable electronic device to a recipient.

An additional embodiment relates to a method to be implemented by electronic devices of a medical monitoring system of a health care facility where a patient's physiological characteristics are being monitored for conditions that may require attention by a clinician. The method includes receiving data from a monitoring device configured to monitor a patient, determining whether the patient has a condition that may require attention based on the data received from the monitoring device, wirelessly sending a notification message to a first portable electronic device if a patient has a condition that may require attention, the notification message including physiologic data, wirelessly sending a notification message to a second portable electronic device if a patient has a condition that may require attention, the notification message including physiologic data, forwarding data to the second portable electronic device based on a user input received from a user input device of one of the first portable electronic device and the second portable electronic device, the data that is forwarded being data associated with a notification message being displayed on the portable electronic device, and transferring voice data received from one of the first portable electronic device and the second portable electronic device to the other of the first portable electronic device and the second portable electronic device. Transferring voice data comprises transferring the voice data using one of a network of the health care facility, a direct wireless connection between the first portable electronic device and the second portable electronic device, and a cellular network.

Other principle features and advantages of the invention will become apparent to those skilled in the art upon review of the following drawings, the detailed description, and the appended claims.

BRIEF DESCRIPTION OF THE DRAWINGS

FIGS. 3A-I are exemplary embodiments of portable electronic devices for use in a notification system according to various embodiments which may be constructed according to the features of FIG. 2;

FIG. 7 is a diagram of a data system according to one embodiment which may be used in conjunction with the system of FIG. 1;

FIG. 8A is a diagram of a communication system according to one embodiment which may be used in conjunction with the system of FIG. 1;

FIGS. 11A-F are exemplary user interfaces for configuring who notification messages are sent to according to one embodiment which may be implemented by the server of FIG. 9;

DETAILED DESCRIPTION

Figure 1:
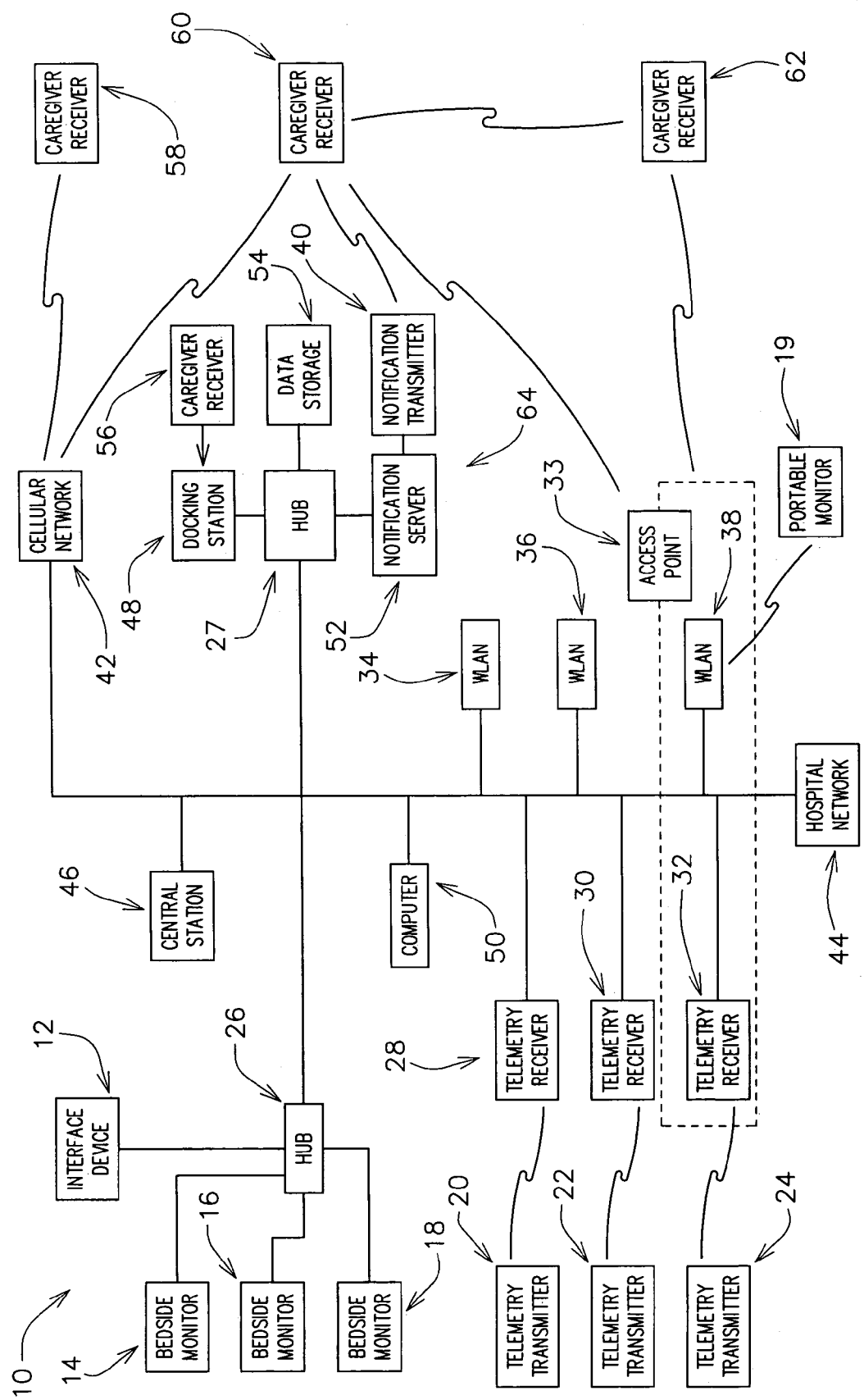
FIG. 1 is a diagram of a monitoring system according to one embodiment.

A caregiver receiver may take various forms and provide various functions depending on the type of alarm notification system. Typically, the alarm notification system is informed as to which caregiver is associated with which receiver such that information may be specifically targeted at particular caregivers or groups of caregivers. The receiver typically has a display for textual information, or in more sophisticated units, graphical information. The graphical display may be used to display an electrocardiogram (ECG) waveform, such as several seconds of a patient's ECG readings, allowing the caregiver to determine whether an associated alarm merits an immediate response. The mechanical structure of the receiver may vary depending on the manufacturer and how it is intended to be worn or carried by the caregiver.

The caregiver receiver may be capable of bi-directional communication such that an incoming alarm may be acknowledged by the caregiver, therefore silencing future pages associated with the same alarm. The receiver may also be able to allow the caregiver to direct an incoming alarm or status message to other caregivers. In a typical bi-directional communications configuration, the caregiver may be able to silence future pages from the alarm notification system upon assessment of the information provided by the system. In some embodiments the caregiver receiver will be able to actually acknowledge and reset the patient monitoring system alarm if the alarm notification system functions as a primary alarm enunciator. The alarm notification system may serve as a primary enunciator of all alarms, or only for some alarms.

An alarm notification system may be configured in many ways depending on the needs of the user. The interface with the alarm notification system may be via a separate computer that houses the alarm notification system software. In other embodiments, the alarm notification system may be accessed via the associated patient monitoring system, either from a central station or via a browser located on another computer.

In one embodiment, an alarm notification system may interface with other hospital electronics and transfer data over a wired phone network, a wireless phone/radio network, a wireless computer network, and a paging transmission system. The interface with other hospital systems may be for alarm notification purposes, such as by providing the ability to send an ECG waveform over a cellular network to a doctor for analysis. Further, the interface with another electronic system may be for other purposes entirely. One example may be for medical records management, such as by sending patient data to a wireless local area network to interface with the hospital's medical records management system.

According to one embodiment, an alarm notification system receiver has the capability of receiving and displaying live data gathered from the patient monitoring system. One type of data that may be transferable is live ECG waveforms.

In one embodiment the receiver includes voice communication capability. The integration of voice communication capability with the alarm notification system may permit a caregiver to discuss alarm information with other caregivers or even the patient by voice communication (e.g. by utilizing Internet protocols). Many advantageous features may become available with voice communication, thus providing a more sophisticated interface without the addition of a complicated communication interface on the caregiver receiver itself.

In one embodiment an alarm notification system permits the storage of data on a central computer but includes the ability to provide the data to caregiver receivers in a seamless fashion thus giving the appearance that the data resides on the caregiver receiver itself. Such a system would permit the use of and access to additional data via the caregiver receiver without requiring the addition of additional computer memory to the caregiver receiver.

One embodiment is directed to a system having receivers that are generic and not customized to one particular user. These generic receivers need to be assigned to particular caregivers. One way of approaching this issue is to assign individual receivers to caregivers at a central computer workstation, thus associating a particular receiver with a particular caregiver in the alarm notification system software. Other ways of accomplishing this include using biometric inputs, smart cards, barcodes, RFID codes, other detectable codes, and voice recognition. If voice recognition is used, the system may be configured to recognize the user's voice using any input and/or may require a user to speak a predetermined word/phrase (a pre-determined input such as a password).

One embodiment is directed to a more sophisticated paging system implementing a more sophisticated paging method such that more flexibility is afforded to the group of caregivers in determining how and when individuals, small groups, or large groups of caregivers are notified of patient monitoring system alarms so that a minimum number of caregivers are interrupted by alarm notification system pages while still ensuring a proper response to alarms.

In one embodiment, the alarm notification system is configured to receive positive acknowledgment that a page has been received by a particular caregiver or set of caregivers without requiring a manual response by the caregiver. Such positive acknowledgment may be one step in the pathway toward using an alarm notification system as a primary enunciator rather than as a secondary enunciator as conventional systems are typically used.

Referring to FIG. 1A, a monitoring system 10 designed to notify a caregiver, such as a clinician, of a condition of the patient that requires attention (an alarm condition) includes a number of monitoring devices 12-24. Monitoring devices 12-24 include monitors 14-19 carrying a number of sensors and typically programmed to run monitoring programs. Based on the monitoring programs, monitors 14-19 set off alarms to indicate that the patient being monitored has a condition that may need attention. Bedside monitors 14-18 typically include a display (either integral with the processing components or separate from the processing components) and a communication interface configured to couple bedside monitors 14-18 to a central station 46 and/or hospital network 44.

Monitoring devices 12-24 may also include a portable monitor 19. Portable monitors 19 generally include sensor inputs, a display, input devices, and processing components within a common housing. Portable monitor 19 also may include a communication interface configured to couple portable monitors 19 to a central station 46 and/or hospital network 44. The communication interface of portable monitor 19 may include a wireless transceiver capable of connecting portable monitors 19 to a wireless local area network access point 34-38. The communication interface of portable monitors 19 may also be configured to make a wired connection. Portable monitors 19 are generally configured to be of lighter weight and include a handle so that they can be readily transported by hospital staff.

Monitoring devices 12-24 may further include interface devices 12 that carry additional sensors and/or equipment to monitor a patient. Interface devices 12 typically do not run monitoring programs, and instead have a primary purpose of expanding on the functionality of the various monitors 14-19. Interface devices 12 may be coupled to a monitor 14-19 and/or central station 46 by way of a network connection (as shown in FIG. 1) or may be directly connected to a monitor 14-19.

Monitoring devices 12-24 may also include telemetry transmitters 20-24. Telemetry transmitters 20-24 can include inputs for any number of sensors used to monitor a patient and typically operate largely from battery power. Telemetry transmitters 20-24 may or may not process data before transmitting the data by way of a communication interface. The communication interface of telemetry transmitters 20-24 is typically configured to transmit data wirelessly to a telemetry receiver 28-32, thereby coupling telemetry transmitters 20-24 to central station 46 and/or hospital network 44. Telemetry transmitters 20-24 are generally designed to be small, compact, lightweight devices such that they may easily be carried by hospital patients. Telemetry transmitters 20-24 may include a clip or a carrying case to facilitate easy carrying by a patient.

Data from monitoring devices 12-24 is typically sent to central station 46, which is typically monitored by a clinician. Data sent from monitoring devices 12-24 may include monitoring data which may include the data acquired from the sensors, data from the sensors which has been processed, and/or alarm data indicating that a condition of the patient may require attention. Based the data received at central station 46, clinicians at central station 46 may determine which patients have conditions which may need attention. Central station 46 may be configured to further process the data including executing additional monitoring programs. Central station 46 is also typically usable to access various health care facility files and programs such as accessing medical record databases that maintain medical records for the patients.

Since clinicians are typically attending to patients and not able to monitor the data displayed at central station 46, an alarm notification subsystem 64 may be included within monitoring system 10.

Alarm notification subsystem 64 includes notification server 52 which acquires patient information from the patient monitoring devices 14-24 (possibly by way of central station 46 or other portion of the system), manages the initiation of notification message transmission, converts the data to proper format for transmission to notification transmitter 40, and sends the message to notification transmitter 40 via a wired connection. Notification transmitter 40 may then send the notification message and may use standard POCSAG paging protocol or other wireless data protocols (such as IEEE 802.11 protocols). One or more of the caregiver receivers 58-62 may receive the message.

Data may be transferred between notification server 52 and caregiver receivers 58-62 (portable electronic devices) point-to-point by way of notification transmitter 40. Data may alternatively be transferred from notification server 52 by way of wireless local area network (WLAN) transceivers 34-38 which may use a IEEE 802.11 protocol.

As another alternative, data may be transferred from notification server 52 to caregiver receivers 58-62 by way of a cellular network transceiver 42, or by more than one of these methods.

The method used to transfer data may be based on the availability of the caregiver receiver 60 which is to receive the data. For instance, a hierarchy may be set up such as notification transceiver 40 may be used if caregiver receiver 60 is within range of notification transceiver 40, WLAN transceiver 34 may be used if caregiver receiver is not within range of notification transceiver 40, and cellular transceiver 42 may be used if caregiver receiver 60 is not within range of either notification transceiver 40 or WLAN transceiver 34.

Notification server 52 may be used to transmit status signals to caregiver receiver 60 to determine the availability of caregiver receiver 60 and then send data to the appropriate receiver when an alarm is to be sent. Alternatively, notification server 52 may sequentially send data using each method until notification server 52 determines that data was received by caregiver receiver 60. Caregiver receivers 58-62 may be configured to send response messages to notification server 52 to indicate that data has been transferred. Also, notification server 52 may use a technology that allows notification server 52 to automatically determine that data has been received.

Clinicians may carry caregiver receivers 58-62 to keep apprised of conditions of patients for which they are responsible and/or other patients. For instance, notification server 52 may be configured to provide periodic status messages indicating the status of the patient. The status message may include physiological data from the patient and may include interpretations of data acquired from the patient.

Caregiver receivers 58-62 are configured to receive information from notification server 52. Information to be received may include notification messages which provide notification of a possible condition of a patient that may require attention. ECG waveform data or other physiological data and interpretations of the data may be transferred as part of the notification message.

Information received from notification server 52 may also include live physiologic data from a patient such that a clinician may evaluate a condition of a patient as if the clinician were viewing a patient monitor 14-19.

Also, medical records for patients for which the clinician is responsible may be accessed by caregiver receivers 58-62. These medical records may be entire medical records, but would preferably contain a less data intensive record which is tailored for the clinician. For instance, a clinician may desire immediate access to a patient's list of allergies, a patient's recommended activities/treatment, a patient's prescribed medication and time schedule for giving those medications, contact numbers for others responsible for the patient, availability of specialists involved with the patient, and a patient's previously recorded physiological values.

Other information may also be transferred between notification server 52 and caregiver receivers 58-62. For instance, inputs from caregiver receivers 58-62 regarding actions to be taken (such as silencing an alarm) may be transferred.

Caregiver receiver 58-62 may be equipped with a large amount of memory 152, 154 (FIG. 2) to store all of the data. Alternatively, caregiver receiver 58-62 may be configured to store data in a remote data storage device 54 wirelessly coupled to caregiver receiver 58-62. Some data that may be stored in remote data storage device 54 may include schedule/calendar information, task information, patient medical data, phone and contact numbers, and other types of data. A data management scheme may be used to make access to the data stored in remote data storage device 54 transparent to a user of caregiver receiver 58. For instance, waveforms may be stored as a series of points which are connected by a program running on caregiver receiver 58 when the data is received. Thus, less data needs to be transferred between storage device 54 and caregiver receiver 58. For transparency, a protocol capable of fast transfer of data (11 Mbps or faster) is preferably used to transfer data. The faster the protocol that is used and the fewer devices that are using a particular bandwidth, the larger the amount of data that can be transferred between storage device 54 and caregiver receiver 58 while still appearing transparent to the user.

Caregiver receivers 58-62 may also communicate directly with each other. For instance, caregiver receivers 58-62 may forward data from one caregiver receiver 62 to a second caregiver receiver 60 or other portable electronic device. This may allow one caregiver receiver 62 to share data (for instance, data sent caregiver receiver 62 with an alarm) with a second caregiver receiver 60 rather than requiring one clinician (e.g. a nurse) to have to explain the data (e.g. an ECG waveform) to a second clinician (e.g. a doctor) over the phone in order for the two clinicians to collaborate to arrive at a course of action. Caregiver receivers 58-62 may also communicate with each other over a hospital network 44, a cellular network 42, and/or some other network.

Caregiver receivers 58-62 may also be configured to communicate with monitors 14-19. For instance, caregiver receivers 58-62 may receive a page from notification server 52 but then communicate with monitors 14-19 to obtain live waveform data. Also, caregiver receivers 58-62 may communicate directly with monitors 14-19 to silence alarms. For instance, caregiver receivers 58-62 may silence alarms by sending a command to monitors 14-19 over the hospital network 44 or may silence alarms by transmitting data directly from a transmitter 120, 122 (FIG. 2) of caregiver receiver 62 to a transmitter of monitor 14 when caregiver receiver 62 is in proximity to monitor 14.

Caregiver receivers 56-62 may further be configured to communicate with some or all of the other portions of the monitoring system by way of a docking station 48. For instance, a caregiver receiver 56 may receive data from notification server 52 by way of docking station 48 to control operation of caregiver receiver 56. Docking station 48 may also be configured to provide power to caregiver receivers 56-62. Docking station 48 may be further configured to identify a user and then send a signal to control association of caregiver receiver 56 with a particular user. This identification may be a biometric input, a unique code identifiable at a distance (such as RFID and/or barcode), password input, or some other method. Docking station 48 may also be configured to communicate with other electronic devices such as a cell phone or personal digital assistant. The cell phone and/or PDA may be a user's personal phone or PDA which they use outside of a work environment. Docking station 48 may also include a wireless transceiver, for instance a short-range link wireless receiver.

Caregiver receivers 58-62 are designed to be transported by caregivers in an easy manner. Caregiver receivers 58-62 would be unlikely to have a volume more than 75 cubic inches, and would likely be cumbersome if they had a volume of more than about 50 to 60 cubic inches. More preferably, caregiver receivers 58-62 would be small enough for a user to place in a pocket and would preferably have a volume of no more than about 30 to 35 cubic inches. Additionally, to facilitate ease of portability, caregiver receivers 58-62 would be unlikely to have a weight of more than 35 oz. More preferably, caregiver receivers 58-62 may have a weight which is less than or equal to 10 oz.

In exemplary embodiments, WLAN transceivers 34-38, telemetry receivers 28-32, and notification transmitter 40 operate in the ISM (Industrial, Scientific and Medical) and/or WTMS (Wireless Medical Telemetry Service) radio frequency bands to transmit data. WTMS generally represents a frequency band of 608-614 Mhz, 1395-1400 MHz, and/or 1429-1432 MHz. WLAN transceivers 34-38, telemetry receivers 28-32, and notification transmitter 40 may be separate devices, may share common components, and/or may share a common housing. For instance, they may be integrated into a common access point 33. Further, some of WLAN transceivers 34-38, telermetry receivers 28-32, and notification transmitter 40 may be integral while others of WLAN transceivers 34-38, telemetry receivers 28-32, and notification transmitter 40 are not integral. Further still, the four types of wireless components described above (WLAN transceivers 34-38, telemetry receivers 28-32, cellular transceiver 42, and notification transmitter 40) may be arranged in any sub-combination. WLAN transceivers 34-38, telemetry receivers 28-32, and notification transmitter 40 may all use the same method to transfer data or, alternatively, may use different methods to transfer data. Different methods could include transmitting data at different frequencies, transferring data using different protocols, and transmitting data relying on other differences that would facilitate transfer of different types of data with less interference between broadcast signals. For examples of potential access points usable in a wireless network established in a hospital, see U.S. patent Ser. No. 10/640,784 titled "WIRELESS LAN ARCHITECTURE FOR INTEGRATED TIME-CRITICAL AND NON-TIME-CRITICAL SERVICES WITHIN MEDICAL FACILITIES" which is hereby incorporated by reference.

While monitoring system 10 has been described with respect to a health care facility, monitoring system 10 may have uses outside the field of health care where a plurality of subjects need to be monitored and an immediate notification of a potential problem which a subject being monitored would be useful.

Also, while components of notification sub-system 64 have been shown as separate from other components of monitoring system 10, the components of notification sub-system 64 may be integral With other components of monitoring system 10. For instance, some of the components of notification sub-system 64 may be integral with central station 46.

Also, while notification server 52 is described as receiving data from central station 46, notification server 52 may be directly coupled to monitoring devices 12-24 or may receive data from monitoring devices 12-24 byway of a hospital network 44. Further, while notification server 52 is described as having a number of functions, these functions may be divided between any number of separate components which, when their functions are combined, collectively become notification server 52.

Additionally, notification transmitter 40 and WLAN transceivers 34-38 may have common components or may be housed in a common housing.

Also, while data from monitoring devices 12-18 are be shown as being coupled to hospital network 44 by way of central station 46, other arrangements are possible.

Also, while data sent to caregiver receivers 58-62 is shown as being sent from a common device (notification server 52), the notification process may be less centralized and may be a function controlled by individual patient monitors 14-19 or by a plurality of processors.

Figure 2:
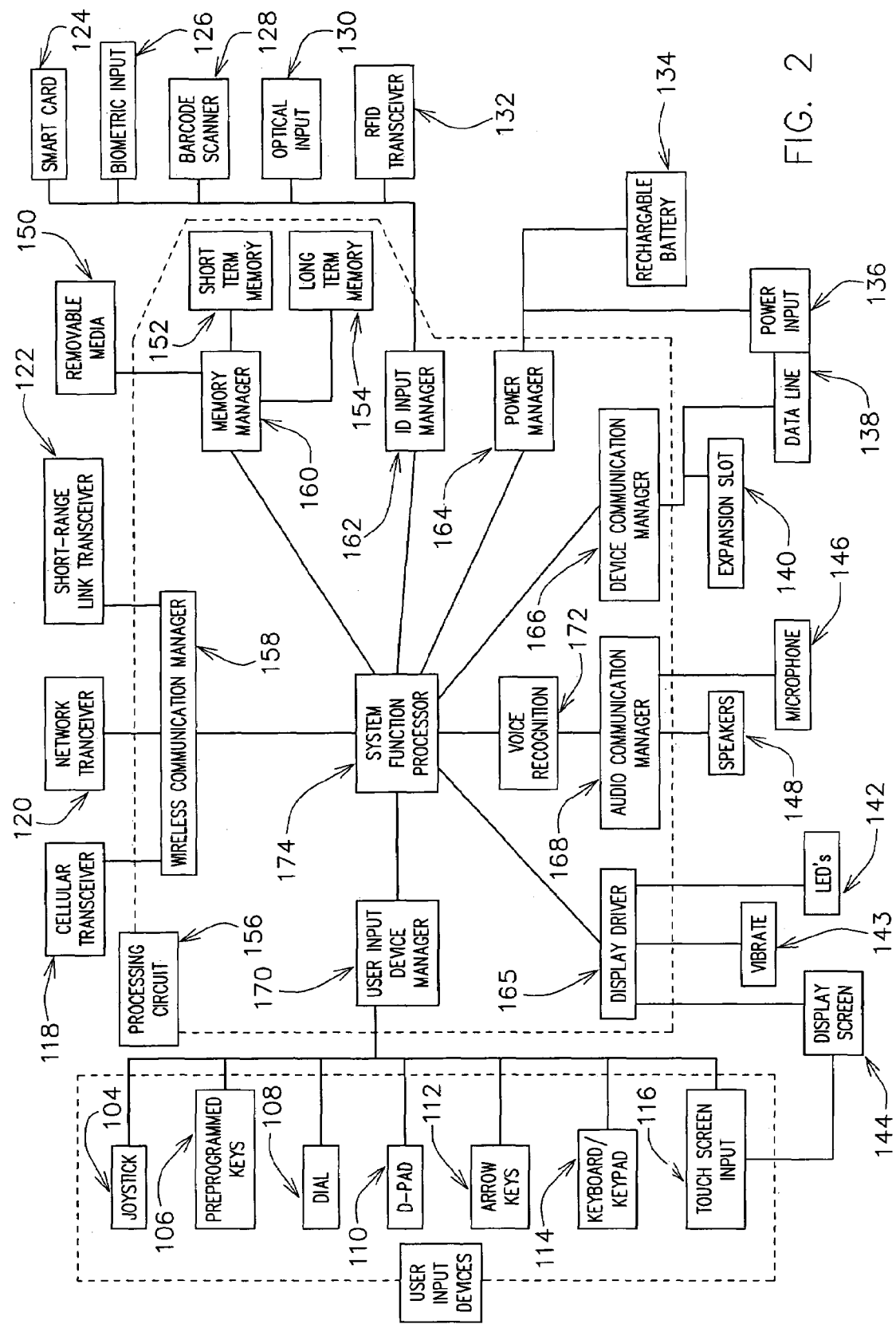
FIG. 2 is a block diagram of a portable electronic device according to one embodiment, which device may be used in the system of FIG. 1.

Referring to FIG. 2, a potential caregiver receiver may include one or more data communication devices 118-122. For instance, caregiver receiver 60 may include a cellular transceiver 118. Cellular transceiver 118 may be configured to transmit voice data and/or computer (digital) data. Cellular transceiver 118 may use TDMA (time-division multiple-access), CDMA (code division multiple access), GSM (GPRS session management), OFDM (orthogonal frequency-division multiplexing), CDPD (cellular digital packet data), GPRS (general packet radio service), and/or any other cellular protocol. Cellular transceiver 118 may be configured to use one or more protocols, and may be comprised of one or more transceivers, transmitters, and receivers. Cellular transceiver 118 may be used to make cellular calls and/or access network data. Also, cellular transceiver 118 may be used as a modem to make a connection to another electronic device (such as another caregiver receiver 58) to transfer data. For instance, when the person desired to be reached by the user of caregiver receiver 60 is not within range of caregiver receiver 60 and/or a hospital network 44, data may be transferred from caregiver receiver 60 by way of cellular network 42. Data to be transferred may include patient data. The patient data may include data of a notification message received by the user of caregiver receiver 60 relating to a condition of a patient that may require attention. This may be useful where the user desires help determining the severity and/or proper treatment of the potential condition.

Caregiver receiver 60 may also include a wireless local area network (WLAN) transceiver 120. WLAN transceiver 120 may be configured to connect caregiver receiver 60 to a hospital network 44 by way of access point 33. WLAN transceiver 120 may also be configured to connect caregiver receiver 60 to notification transceiver 40. WLAN transceiver 120 may be further configured to transfer data between caregiver receivers 58-62.

WLAN transceiver 120 may use any number of protocols including IEEE 802.11 protocols. The IEEE 802.11 standard is the family of specifications created by the Institute of Electrical and Electronics Engineers Inc. for wireless, local area networks in 2.4 and 5 gigahertz bandwidth spaces. IEEE 802.11 is a way to connect computers and other electronic devices to each other and/or to the Internet at high speeds without requiring wiring. IEEE 802.11(b) protocol currently may allow devices to communicate at up to 11 Mbps and IEEE 802.11(g) protocol currently may allow devices to communicate at up to about 54 to 108 Mbps. IEEE 802.11 protocols typically have a range of up to about 100 meters indoors and 400 meters outdoors.

WLAN transceiver 120 may use a radio frequency signal to transmit data and may operate in an ISM band, in a WTMS band, or in some other band. WLAN transceiver 120 may be used to track the location of caregiver receiver 60 by any number of techniques including determining the receiver(s) 34-38 which receive a strongest signal from WLAN transceiver 120, or determining the relative strengths of signals received by receiver(s) 34-38 from transceiver 120, determining an amount of time needed to transmit a signal from transceivers 34-38 to WLAN transceiver 120 and to receive a response, and/or by some other technique.

The determined location of caregiver receiver 60 may be used to control caregiver receiver 60. For instance, certain wireless frequencies or Wireless data transfer protocols may be restricted and/or unavailable in some areas of a health care facility. In response to a determination that caregiver receiver 60 is entering a restricted area (or an area of unavailability), caregiver receiver 60 may adjust its wireless data protocols. For instance, wireless caregiver receiver may automatically switch to transfer data using a different protocol or may be configured to go to a stand-by mode wherein caregiver receiver 60 is configured to receive data but not to send wireless signals.

Caregiver receiver 60 may also include a short-range transceiver 122 which has a shorter range than either of the other transceivers. Short-range transceiver 122 may use BLUETOOTH™ technology. The BLUETOOTH trademark is owned by BLUETOOTH SIG, Inc. BLUETOOTH wireless technology provides wireless connections; enabling links between mobile computers, mobile phones, portable handheld devices, and connectivity to the Internet. BLUETOOTH devices tend to have a low power consumption and a low cost.

The BLUETOOTH wireless specification includes both link layer and application layer definitions for product developers which supports data, voice and content-centric applications. Radios that comply with the Bluetooth™ wireless specification operate in the unlicensed, 2.4 GHz ISM (Industrial, Scientific and Medical) Band radio spectrum. These radios use a spread spectrum, frequency hopping, full-duplex signal at up to 1600 hops/sec. The signal hops among 79 frequencies at 1 MHz intervals to give a high degree of interference immunity. BLUETOOTH's synchronous bands are geared to carry relatively high-quality voice, while the asynchronous communication will support data at slightly more than 700 Kbps.

Distance for standard BLUETOOTH devices is limited to about 10 meters, but can be expanded to much larger distances (such as 100 meters) if desired. Once the devices are within the distance boundary, the devices can be connected automatically. BLUETOOTH also provides a fast and secure transmission of voice and data even when the devices do not have a line of sight. Short-range transceiver may be used as a lower power alternative to transmitting data between electronic devices (such as monitors 14-18 and caregiver receiver 60) and may be used to determine proximity of other components to caregiver receiver 60.

Caregiver receiver 60 may also include one or more subject/user identification devices 124-132. A subject identification device is a device used to identify a subject of interest other than a user (record, patient, etc.). A user identification device is a device that is used to identify a user of caregiver receiver 60. Subject/user identification devices 124-132 may be used as security measures, may be used to customize caregiver receiver 60, and/or may be used as an administrative device (such as linking data to or accessing appropriate records).

A first subject/user identification device is smart card slot 124 which is configured to receive a smart card carrying a unique code representing the user. The user would insert a card 124 into smart card slot 124 and caregiver receiver 60 would identify the user based on the code carried by smart card 124. Smart card 124 may also carry information about the user including PDA data (calendar, task list, contacts, etc.), phone data (phone numbers, customized voice dialing inputs, etc.), patient data for the patients for which the user is responsible, cellular phone protocols, other programs to be run that are particular to the user, or any other type of information. Smart card 124 may contain an internal microprocessor or other processing circuit that regulates access to the data stored on smart card 124.

Another subject/user identification device is a biometric input 126. A biometric input 126 can identify a user of caregiver receiver 60 based on a unique physical attribute of the user. Examples of biometric inputs 126 would be fingerprint identification and retinal scan. Other biometric inputs 126 may also be possible.

Still another subject/user identification device is an barcode scanner 128 that can identify a unique code in the form of a barcode. A barcode may be associated with hospital records, with a patient, or with other subjects of interest. Also, a user may have an ID badge containing a unique barcode representing the user. Barcode scanner 128 may be capable of scanning codes formed in one dimension or in two dimensions. Barcode scanner 128 may use fuzzy logic, may use an omni-directional scanning technique, and may use a raster pattern to improve performance and/or increase ease of the scanning process.

Yet another subject/user identification device is an optical input device 130. Optical input device 130 may be a solid-state camera and may have a resolution of between about 0.3 megapixels and about 3.3 megapixels. More preferably, optical input device 130 has a resolution of at least about 1.0 megapixels and a resolution of no more than would allow a picture to be transferred over a network in which the device is used in a short amount of time. Further, the resolution of optical input device 130 may be variable. Optical input device 130 may be configured to identify patterns in an optical image, for instance a unique code that is based on a unique arrangement of components (lines, boxes, etc.). Optical input device 130 may also be configured to obtain images of a subject of interest. These images may be transferred to other users. This may be useful when a patient has a condition that may require treatment (such as hives), where a user would like to obtain input from a remote user, and where seeing the condition would be valuable for treating the condition.

One more possible subject/user identification device is an RFID (radio frequency identification) transceiver 132. RFID transceiver 132 may be used to identify a unique signal associated with a subject of interest. RFID transceiver may be configured to obtain data from passive RFID tags associated with patients, records, or other subjects of interest. Also, a user may have an ID badge containing an RFID tag having a unique code representing the user.

If a unique code associated with a patient or record is identified by a subject identification device 124-132, that identification may be used as an input to a field of a program being run by caregiver receiver 60 (such as assigning a test result or record to a proper patient). Additionally, that code may be used to keep track of a patient's medication (by identifying the codes associated with both the medication and the patient), could be used to admit and discharge patients, could be used to print information associated with the patient, could prompt display of a task list of tasks associated with the patient which need to be done, could be used to sort patients, and/or could be used to associate a patient with the user of caregiver receiver 60. Also, that identification could be used to prompt display of information regarding that patient on display screen 144 of caregiver receiver 60 (e.g., a medical record, status of the patient's lab results, location of patient's medication, etc.). See, for instance, U.S. patent application Ser. No. 10/304,538.

If a unique code associated with a user is identified by a user identification device 124-132, that code can be used to customize caregiver receiver 60. For example, a user may desire that certain information be arranged in a particular manner. Additionally, if data associated with the user is not permanently stored on notification device, identifying the user can be used to indicate the proper file from which to download/access data. Data to be accessed can include any of that discussed above including PDA data, phone data, patient data of patients for whom the user is responsible, etc.

Caregiver receiver 60 may include one or more microphones 146 and one or more speakers 148. Microphones 146 (acoustic input transducer) may be used to dictate notes, may be used to input data to be analyzed, may be used to input a user's voice to be transferred in voice communication applications, or may serve some other purpose. Speakers 148 (acoustic output transducer) may be used to output data that has been collected, to play music, to serve as an earpiece for voice communications, or to serve some Other purpose. Microphone 146 and speaker 148 may alternately (or additionally) be in the form of output jacks for receiving an acoustic sensor or acoustic output transducer. Microphone 146 and speaker 148 preferably cooperate with processing circuit 156 and at least one of cellular transceiver 118, WLAN transceiver 120, and/or short-range transceiver 122 to form a wireless voice communication device (wireless phone) that allows voice data to be shared over a cellular network (cellular phone), between two notification devices 58, 60 or other electronic devices (walkie-talkie phone), and/or over some other network (network phone) such as hospital network 44 (hospital network phone).

Caregiver receiver 60 may include various visual display devices 142-144. Caregiver receiver 60 may include one or more display screens 144 that display data. Display screens 144 are preferably able to capable of displaying graphical data (i.e. the screen is able to illuminate pixels in order to draw waveforms and other images that are not text). A caregiver receiver 60 with graphical display capability may provide more information for use by a caregiver than a caregiver receiver that has only textual display capabilities or no visual display capabilities. Display screens 144 may be in color or may be in some other format such as grayscale. Display screens 144 may comprise OLED display screens and may be at least partially flexible (for instance when using a Polyethylenenapthalate-substrate-based (PEN) or Polyester-substrate-based (PET) active matrix to control the OLED display).

Caregiver receiver 60 may also include LEDs 142. LEDs may be arranged as point sources of light which are generally used as indicators or may serve some other purpose.

Caregiver receiver 60 may also include a vibrating device 143 configured to vibrate in response to a control signal from processing circuit 156 sent to alert a user to the receipt of the notification message. Vibrating device 143 may be used to indicate an alarm where the use of noise or flashing lights may be distracting. Vibrating device 143 may be made integral with the rechargeable battery assembly 134.

Caregiver receiver 60 may also include memory 150-156 for storing data. Memory for caregiver receiver 60 may be in the form of a removable media drive 150 that can read data written on a removable computer writable media. Examples of computer writable media include computer writable chips (multimedia card—MMC, secure digital—SD, compact flash—CF, memory stick—MS, smart media—SM, etc.), floppy disks, DVDs, CDs, etc. Removable media drive 150 is preferably compact in size and is preferably a drive capable of reading computer writable chips. Removable media drive 150 may be configured to read more than one type of computer writable chip and may be configured to accept data from four or five different types of chips. Memory for caregiver receiver 60 may also be in the form of integral short term memory 152 which requires the presence of an electrical charge to maintain the stored data. Memory for caregiver receiver 60 may also include integral long term memory 152 that is configured such that an electrical charge is not needed to maintain the stored data. In alternate embodiments, at least one of the three types of memory is not present to save space, and may typically be long term memory 154. Smartcard slot 124 and removable media drive 150 may share a common slot and common electronic components.

Caregiver receiver 60 may also include one or more user input devices 102. Potential user input devices 102, include a joystick 104, directional pad (D-pad) 110, and arrow keys 112. Joystick 104, D-pad 110, and arrow keys 112 may be used to navigate menu options of caregiver receiver 60. Also, joystick 104, D-pad 110, and arrow keys 112 may have selection features that allow a user to select an option using these user input devices 102. For instance, using the keys to move up and down may scroll between options, moving forward may select an option and moving backwards may unselect an option. Alternatively (or additionally), pressing the center of joystick 104 or d-pad 110 may select an option and moving the user input devices 102 in a direction moves an indicator or the display in that direction.

User input devices 102 may also include a dial 108. Dial 108 may be located on a surface of caregiver receiver 60 and have its entire circumference visible or dial 108 may be recessed into a face of caregiver receiver 60 with only a portion of its circumference showing. A user may use dial 108 to scroll between menu options displayed on a display screen 144. Dial 108 may also be configured to have a selection feature which allows a user to actuate dial 108 in a manner that allows the user to select a highlighted option. For instance, dial 108 may be configured to also be a button that a user may push to make a selection. Using a dial 108 with a selection feature would allow a user to quickly navigate and select menu options on caregiver receiver 60 using only a single hand.

Another potential user input device 102 is a set of preprogrammed/hot keys 106. Pre-programmed keys 106 are preset to perform a function and may be preset by a manufacturer and/or by a user. For instance, three pre-programmed keys 106 may be used to automatically switch the mode of operation of caregiver receiver 60 between use as a personal digital assistant, a subject identification device, and a communication device. Alternatively, caregiver receiver 60 may include five or six pre-programmed keys 106 which may be used to access five or six different functions of caregiver receiver 60 such as access a calendar, access a task list, access a communication tool (phone book, dialer, voice-dialer, etc.), access a memo pad, initiate subject identification, and initiate transfer of patient data. Pre-programmed keys 106 may be in the form of buttons, switches, areas on a touch screen, or other types of keys.

Another potential user input device 102 is a keyed input device 114 such as a keyboard or keypad. One such keyed input device 114 is a keyboard which generally includes keys for each of the letters of the alphabet. Keyboard 114 may be a full size keyboard which is typically used with computers, but is preferably a small keyboard such as a thumb keyboard. Small keyboards typically have smaller keys, and thumb keyboards typically have small bumps for each key. A small keyboard is preferably no wider than about seven inches, and more preferably no wider than about three and a half inches. Another keyed input device 114 is a keypad. A keypad generally has fewer than a full set of keys. A keypad may include keys for each of the numbers from 0 to 9, #, and * and may include the ability to use a single key to input more than one character, typically by pressing the key more than once for the additional character.

Still another potential user input device 102 is a touch screen 116 which allows a user to touch a portion of a screen to input a command. An advantage of a touch screen 116 is that it can be made integral with a display screen 144. This may allow the commands that are implemented by actuating touch screen 116 to vary. In one embodiment, areas of touch screen 116 that may be actuated would be large enough to allow a user to use a finger to actuate the command.

Caregiver receiver 60 may be powered by a rechargeable battery 134 and may have an power input 136 configured to receive power from an external power source.

Caregiver receiver 60 may also include one or more data ports 138 (such as a serial port) that are configured to allow wired transfer of data between caregiver receiver 60 and an external electronic device (such as docking station 48). A data port 138 may have a common connection with power input 136 such that caregiver receiver 60 may be configured to make both a wired data connection and a power connection with a single connection. Caregiver receiver 60 may also include one or more expansion slots 140 that may be used to add peripheral devices to caregiver receiver 60 to increase the functionality of caregiver receiver 60. Expansion slots 140 may use common components with data port 138 and/or removable media drive 150.

A data port 138 may also be used to make a wired voice communication channel for caregiver receiver 60. This may be useful, for instance, when the user is an area where wireless devices are restricted because they may be harmful to conditions of patients, they may interfere with operation of medical diagnostic instruments, or they may be have difficulty transferring data due to interference from the medical diagnostic instruments. A user would be able to connect caregiver receiver 60 to hospital network 44 (FIG. 1A) by way of a wired connection instead. The wired connection may be made by way of a serial communication line, a telephone line, an Ethernet line, etc.

Data port 138 may likewise be able to connect caregiver receiver to other portable electronic devices (such as a cell phone, PDA, etc.) using a wired connection.

Caregiver receiver 60 may also include a processing circuit 156 configured to process data received from and sent to the various components 102-154 and to run programs associated with the functions of caregiver receiver 60. Processing circuit 156 can include various types of processing circuitry, digital and/or analog, and may include a microprocessor, microcontroller, application-specific integrated circuit (ASIC), field-programmable gate array (FPGA), or other circuitry configured to perform various input/output, control, analysis, and other functions to be described herein. Processing circuit 156 may include one or more microprocessors/microcontrollers, ASICs, and/or FPGAs. Also, while the functions of processing circuit 156 are preferably controlled by a common, consolidated set of components, each of the functions of processing circuit 156 may be performed by separate components and remain within the definition of processing circuit used herein.

Processing circuit 156 is preferably configured to operate as a notification device capable of notifying a user of a condition of a patient that may require attention. To perform this function, processing circuit 156 may be configured to wirelessly transfer data to notification server 52 using data received from a wireless transceiver 118-122. Processing circuit 156 may output a control signal to control speaker 148, vibrating device 143, display screen 144, and/or LEDs 142 to output a signal to alert a user to the receipt of the notification message. For this function, processing circuit 156 may also be configured to output patient physiological data to screen 144. One example of patient physiological data may include ECG waveform data that led to the alarm (possibly 6 seconds of data) and data gathered shortly after the alarm. Physiological data may also include near real-time/live data (i.e. as it is gathered or shortly after it is gathered, patient physiological data is displayed). For this function, processing circuit may also display a list of options for the user. Options may include an option to contact other clinicians, an option to display live data, an option to display additional or different types of patient data (such as trend data, pulse oximetry data, processed data, etc.), an option to display one or more interpretations of the data (such as check ECG connection or check pulse oximetry probe off, HRV risk evaluation, and other risk evaluation—see U.S. patent application Ser. No. 10/440,747 titled "METHOD AND APPARATUS FOR MONITORING USING A MATHEMATICAL MODEL" and U.S. patent application Ser. No. 10/625,633 titled "MONITORING SYSTEM AND METHOD USING RULES"), an option to silence alarms for the caregiver receiver, an option to forward data, an option to transfer the alarm to a group, an option to silence an alarm globally, an option to add a task to a task list, and/or other options. Processing circuit 156 may be configured such that some or all of this data is displayed along with the notification of the alarm when the alarm is received.

Processing circuit 156 may also be configured to perform the functions of a personal digital assistant. Processing circuit 156 may be configured to receive, store, and display lists of tasks, schedule information, and notes. Processing circuit 156 may be configured to store this data in memory 152-154 until deleted or overwritten (permanently) or may be configured to store this data temporarily based on the identity of the user. For instance, in response to receiving an input of an identity of a user, processing circuit 156 may be configured to use a transceiver 118-122 to communicate a request for data and receive data from a network where the data comprises one or more of the task, schedule, and notes information for the user. Processing circuit 156 may also be configured to run one or more user specific programs such as a word processing program, an internet client, an intranet client, a database program, or some other program. Processing circuit 156 may also have contact information stored in a contact manager or other database.

When acting as a personal digital assistant, caregiver receiver 60 is preferably configured such that it is not running so many programs that if the notification function is launched the notification function will operate slowly. In order to accomplish this, caregiver receiver 60 is preferably configured such that it does not run programs unrelated to patient care. Some functions unrelated to patient care may include-MP3 players, an unrestricted internet browser (i.e. a browser may be run which is restricted to medical and or patient-related sites and data), games, etc. Processing circuit 156 may be configured to reject the addition of programs unrelated to patient care and/or may be configured to only allow installation of such software with approval from a manager.

Processing circuit 156 may also be configured to serve as a wireless voice communication device, such as a wireless phone. Processing circuit 156 may be configured to process and transfer data between microphone 146 and speaker 148 and a wireless transceiver such as a transceiver of a different caregiver receiver, a WLAN transceiver 34-38, a cellular network transceiver 42, or some other transceiver. Processing circuit 156 may be configured to establish a voice link with another electronic device based on a user input received from keypad 114. Processing circuit 156 may be configured to establish a voice link with another electronic device based on a comparison of user audio inputs and stored user voice dialing data. Processing circuit 156 may be configured to send user audio inputs to a separate electronic device, such as central station 46, which may be coupled to a database 54 containing stored user voice dialing data. Processing circuit 156 may also store phone contact information in a phone book or other database.

Processing circuit 156 may also be configured to perform a subject identification function. Processing circuit 156 may be configured to initiate a scan for a unique code using a subject identification device 124-132. Processing circuit 156 may receive data representative of an ID code from a subject identification device 124-132 and may apply the ID data from the subject identification device 156 to a program being run, such as filling in an appropriate field in a chart. Processing circuit 156 may be configured to display data based on the ID data received. For instance, processing circuit may be configured to display data relating to a patient who has been identified based on the ID data. Processing circuit 156 may be configured to store the patient data displayed, or may be configured to request/receive certain data based on the identity of the patient.

When running any of these additional functionalities, processing circuit 156 is preferably configured such that the alarm notification program has a highest priority. If an alarm is sent, that alarm will be displayed instead of the information with which a user is working. Further, if an event occurs in another program unrelated to the notification program (such as a meeting notice from a calendar or an incoming call from a phone) and the notification program is being used, information relating to the event is either not displayed until the notification program is no longer being actively used or the information is displayed in a manner such that it does not interfere with the display of data relating of the notification program. For instance, if a user has a meeting scheduled in a calendar program and has set a reminder, that reminder may be displayed across a full screen with all of the details displayed in a normal mode and may be displayed as an asterisk in a corner of a display screen with few of no details when the notification program is being actively used.

If an alarm occurs, the notification program may be configured to automatically minimize any other application being run and switch over to the notification application.

Processing circuit 156 may be configured to run an operating system that allows multi-tasking to occur, such as a Windows CE or a Pocket PC operating system. Other examples of operating system that may be used include Linux, Palm OS, Symbian, or some other operating system directed to operate a PDA.

While reference is made herein to patient data, caregiver receiver 60 may be applicable to other types of subject data as well where other subjects of interest are being monitored. Further, while description has been made with respect to a caregiver receiver configured to notify a user of a condition of a subject that may require attention, the portable electronic device shown in FIG. 2 may be applicable to a number of other uses as well.

Also, while a number of different types of user input devices are shown, to conserve space and cost, some types of input devices may not be found together. For instance, D-pad 110, arrow keys 112, and joystick 104 have similar inputs and so caregiver receiver 60 may only have one or two of those input devices. Also, caregiver receiver 60 may use only one or two types of data communication transceivers 118-122. Additionally, caregiver receiver 60 may only include only one device configured to identify a subject of interest and/or one device configured to identify the user. Further, the subject identification device and/or the user identification device may be coupled to caregiver receiver 60 by way of expansion port 140. Further still, while multiple subject identification devices 124-132 are possible, a barcode scanner 128 and/or an RFID transceiver 132 may be the best suited subject identification devices.

Additionally, while reference has been made to a transceiver, it should be understood that a receiver and a transmitter may, together, perform substantially the same function as a transceiver in substantially the same way. Thus, reference to a transmitter or a receiver in the claims is not meant to indicate that the transmitter or the receiver are not a portion of a transceiver or other similar device, and reference to both a transmitter and a receiver is not meant to indicate that the transmitter and the receiver are separate devices.

Also, while only one cellular transceiver 118, one WLAN transceiver 120, and one short-range transceiver 122 are shown, more than one of each of these transceivers may be used to perform one or more of the functions of the portable electronic device.

Figure 3A:
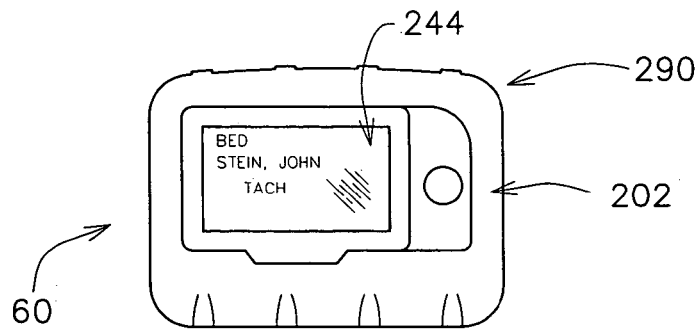

Referring to FIG. 3A, a caregiver receiver 60 includes a user input device 202 and a display screen 244 in a housing 290. Housing 290 is preferably configured to be sufficiently rugged for the application in which it is used. In a health care environment, housing 290 may be able to withstand impacts such as being dropped, temporarily coming into contact with sharp objects, having pressure applied by leaning on the device, and may be resistant to liquids. Housing 290 may be rugged enough to withstand repeated drops from about 3 ft to about 5 ft. (about 1 m to about 1.5 m) to a hard floor of a health care facility.

Further, housing 290 is preferably resilient to bacterial growth. For instance, housing 290 may be configured such that it may be safely wiped with an anti-bacterial substance. The anti-bacterial substance may be a lotion, may be a liquid, or may take some other form. Also, housing 290 may be configured to contain anti-bacterial agents within the material of the housing. In one exemplary embodiment, anti-bacterial agents may be incorporated in a polymer's molecular structure and then the polymer is used in forming a housing. Another option would be to use a polymer including a host molecule that can host an anti-bacterial agent and then introducing the anti-bacterial agent to the host molecule.

Housing 290 is preferably compact enough to be easily carried around, yet large enough to have a sufficient screen size to display information. Housing 290 preferably has a volume less than about 30 to 35 cubic inches and more preferably less than about 10 cubic inches. Housing 290 may have a height that is less than about 7 inches and preferably no more than about 5.6 inches. Housing 290 may have a width that is no more than about 3.5 inches and preferably no more than about 2 inches. Housing 290 may have a thickness less than about 1.5 inches and preferably no more than about 0.85 inches. In one embodiment, housing 290 is about 5.75 in. by 3.25 in. by 1.25 in. In a more ideal embodiment in terms of housing size, housing 290 is about 5.6 in. by 2.0 in. by 0.85 in.

Housing 290 is also preferably light weight. Housing 290 may have a weight of less than 20 oz, and more preferably has a weight of no more than about 10 oz. Most preferably, housing 290 weighs no more than about 2.5 oz.

Figure 3B:
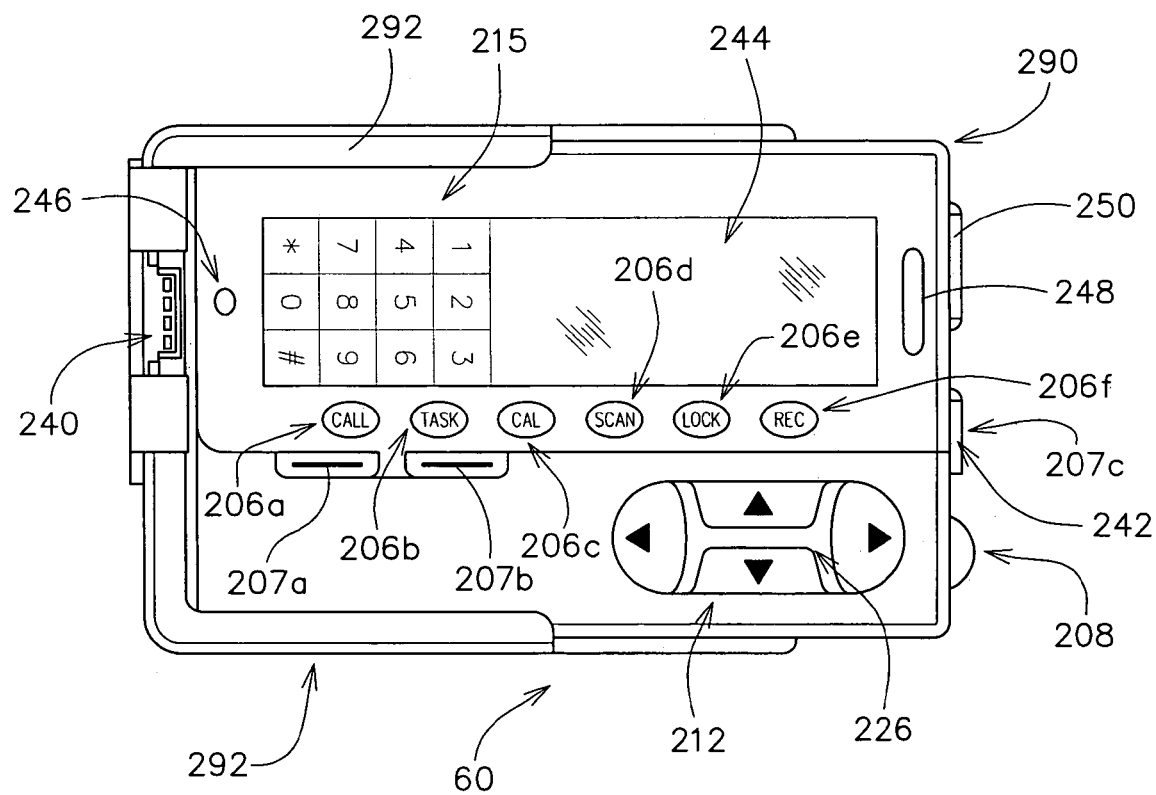

Referring to FIG. 3B, a caregiver receiver 60 includes a display screen 244. Display screen 244 may also be configured as a touch screen that may receive user inputs. Display screen 244 may be configured to display data horizontally (here, the dimension with the longer length) or vertically (here the dimension with the shorter length). The characters of soft keypad 215 are shown as displayed vertically. The direction of the displayed data may be switchable based on a user input. Also, the direction of displayed data may be switchable automatically by a program. For instance, if a phone program is used then the display may display data in a first direction (vertically) whereas if a notification alarm is received then data (such as ECG waveform data) may be displayed in a second direction (horizontally). Data from notification alarms is preferably displayed in a manner such that a user can tilt caregiver receiver 60 towards their viewing direction to view the data in a normal manner.

Caregiver receiver 60 may also include a number of user input devices 102 (FIG. 2). User input devices 102 may include arrow keys 212, a dial operator 208, buttons 207*a-h*, and pre-programmed keys 206*a-f*.

Buttons 207*a* and 207*b* may be used to toggle menus, change the volume of the output from speakers 248, or perform some other function. Button 207*c* may be used as a power button to operate screen 244.

Pre-programmed key 206*a* may actuate a phone related function. For instance, when pre-programmed key 206*a* is actuated, processing circuit 156 (FIG. 2) may control display screen 244 to display soft keypad 215 on display screen 244. Soft keypad 215 is an area of a touch-screen that may be used to replicate a keypad. Soft keypad 215 may always be displayed, or may be displayed only in response to a user selection such as actuating pre-programmed key 206*a*. Pre-programmed key 206*a* may also be used to display a contact list, to make a connection with a central calling list (see FIG. 13), or to perform some other phone related task.

Pre-programmed key 206*b* may be used to access a task list, pre-programmed key 206*c* may be used to access a calendar, and pre-programmed key 206*d* may be used to operate a subject identification device such as a barcode scanner or an RFID transceiver.

Pre-programmed key 206*e* may be used to "lock" the other keys such that processing circuit 156 (FIG. 2) will not be responsive to actuation of other user input devices 102 (including screen 244) until the device becomes unlocked. To unlock the keys, a user may be asked to actuate two particular keys, to actuate pre-programmed key 206*e* followed by the desired function, or may unlock the system by some other method. If an alarm is received by caregiver receiver 60 indicating that a patient being monitored has a condition that may require attention, all of the keys may become unlocked. The keys may become permanently unlocked, unlocked for a set amount of time, or unlocked until the alarm is cleared. Alternately, certain keys may remain locked when the alarm is received such as pre-programmed keys 206*b* and 206*c*. As another option, only certain keys become unlocked when an alarm is received such as dial 208, pre-programmed key 206*a*, pre-programmed key 206*f*, and arrow keys 212.

Pre-programmed key 206*f* may be used to access patient records. Actuation of pre-programmed key 206*f* may bring up a list of patients for whom the caregiver is responsible, and selection of a patient using dial 208 will result in display of a patient record. The patient record may include a full record, may include tasks on the caregiver's task list associated with that patient, may include a truncated record containing only the more useful information for the user, and/or may contain some other information.

Caregiver receiver 60 may further include a data port 240 that may be used to transfer data from caregiver receiver 60 to another device using a wired connection. Data port 240 may also be an expansion slot 140 (see FIG. 2) to add peripheral devices to caregiver receiver 60. Data port 240 may be formed as a slot, a projection, a recess and/or some combination of these forms Caregiver receiver 60 may also include a removable media slot 250. Removable media slot 250 may be a secure digital input/output (SDIO) port configured to receive removable media and to receive plugs from expansion devices such that expansion devices may communicate with processing circuit 156 and/or screen 144 (FIG. 2).

Caregiver receiver 60 may also include a microphone 246 which may be used with speaker 248 in a voice communication application where caregiver receiver 60 is a voice communication tool with integrated audio components.

Caregiver receiver 60 also includes an indicator LED 242. Indicator LED 242 may be used to indicate any number of types of information. For instance, indicator LED 242 may be configured to indicate system power information, may be configured to indicate the type of wireless connection (direct, network, cellular) available to be made with notification server 52 (FIG. 1), may be configured to indicate that an alarm has been received, may be used to indicate a severity of an alarm being received, etc. Indicator LED 242 may include a single LED and output a single color, may include a plurality of LEDS that output the same or different colors, or may include an LED configurable to output more than one color of light.

Caregiver receiver 60 may also include a biometric device 226 capable of identifying a user's fingerprint. Biometric device 226 may be configured to use a thermal scanning technique that measures differences in temperature between ridges and valleys on a finger; biometric device 226 may use a capacitative-based fingerprint technology and/or a radio frequency imaging technique that allows the sensor to generate an image of the shape of the finger print (potentially based on a structure of the live layer of the skin that is beneath the surface of the finger). Other biometric devices 126 (FIG. 2) may include a device configured to recognize an iris pattern or a facial shape of a user. In response to an input received from biometric device 226, processing circuit 156 (FIG. 2) may be configured to customize programs running on caregiver receiver 60.

Caregiver receiver 60 may also be configured to be mounted in a carrying case 292 having sidewalls configured to snap fit with caregiver receiver 60. Carrying case 292 may be made of plastic and may be rigid. Alternatively, carrying case may be made of other materials and may include portions that are not rigid.

Figure 3C:
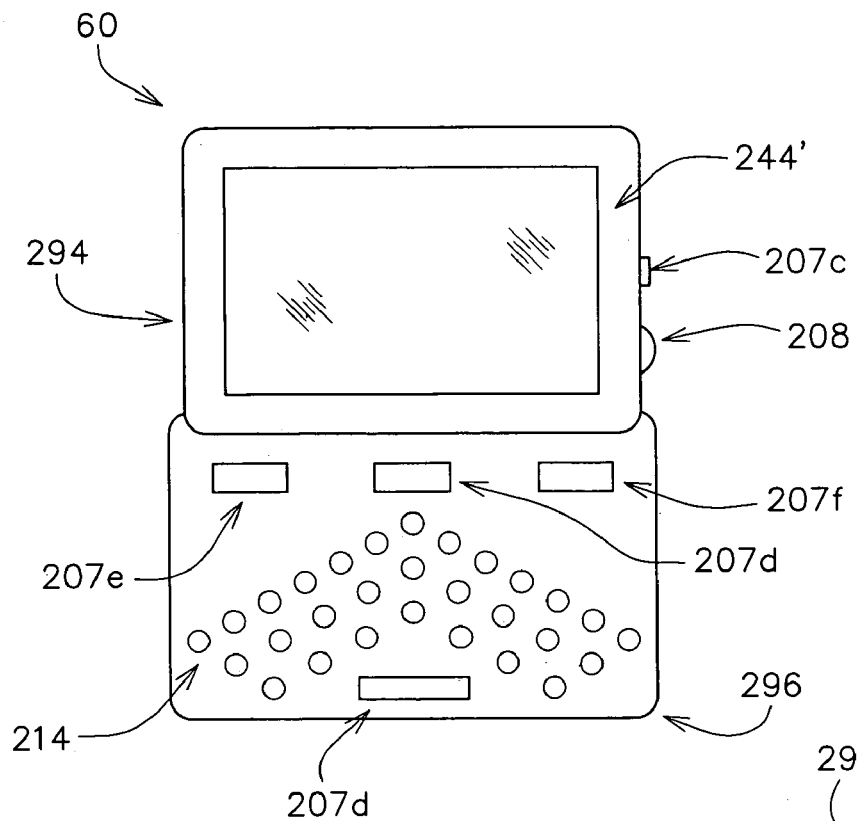

Referring to FIG. 3C, housing 290 may be configured to be a two-part housing having a first part 294 and a second part 296. Parts 294 and 296 may be configured to snap shut in a closed position (as seen in FIGS. 3A and 3B). First part 294 is the thicker part carrying most of the components of caregiver receiver 60. Screen 244', located in first part 294, becomes accessible in the open position. Screen 244' may be a display screen and/or a touch screen. In one embodiment, screen 244 is only a display screen and screen 244' is both a display screen and a touch screen. In another embodiment, screen 244' is only a display screen and screen 244 is both a display screen and a touch screen. Screen 244' is generally larger than screen 244.

Second part 296 carries a thumb keyboard 214 with the keys arranged in an arrow formation. Second part 296 also includes additional keys 207e-f.

Figure 3D:
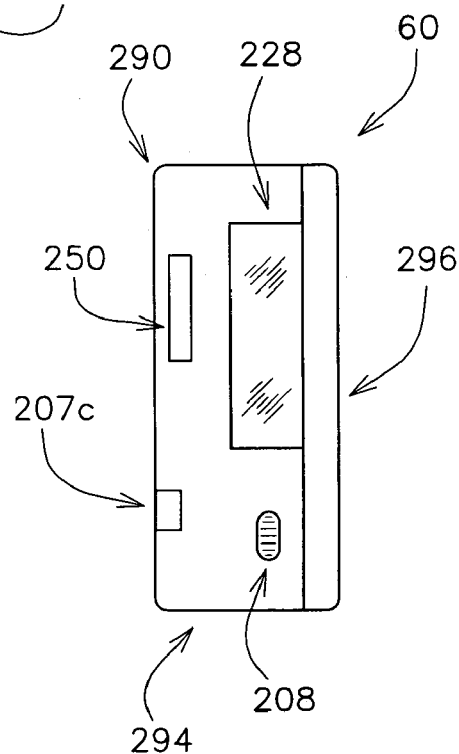

Referring to FIG. 3D, caregiver receiver 60 includes a barcode scanner 228 housed within housing 290. Alternatively, housing 290 may be configured to carry a barcode scanner 128 (FIG. 2) by including an adapter to which barcode scanner 128 may be affixed.

Figure 3E:
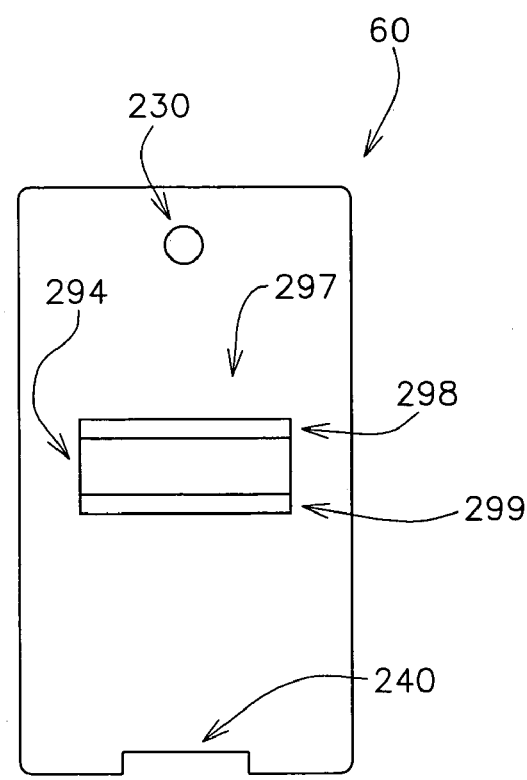

Referring to FIG. 3E, caregiver receiver 60 includes a camera 230. Caregiver receiver 60 may also include an attachment mechanism 297 to removably attach caregiver receiver 60 to a carrying clip. Attachment mechanism 298 may include a pair of recess and ridges 298, 299.

Referring to FIG. 3F, caregiver receiver 60 includes additional keys 207g and 207h. Keys 207g and 207h may be used to increase and decrease volume. Caregiver receiver 60 also includes a speaker/microphone jack 148' which may be used to allow a user to removably attach a speaker and/or microphone to housing 290.

Caregiver receiver 60 also includes a clip 291 that may facilitate connection of caregiver receiver 60 to a user's clothing. Connector 293 of clip 291 may be removably connected to attachment mechanism 297 of caregiver receiver 60. Clip 291 may be configured such that caregiver receiver 60 may rotate (up to 110 degrees in one embodiment) with respect to clip 291 around pivot point 295 of clip 291. In this manner, a user may quickly flip up caregiver receiver 60 to view the information displayed on screen 244.

Figure 4:
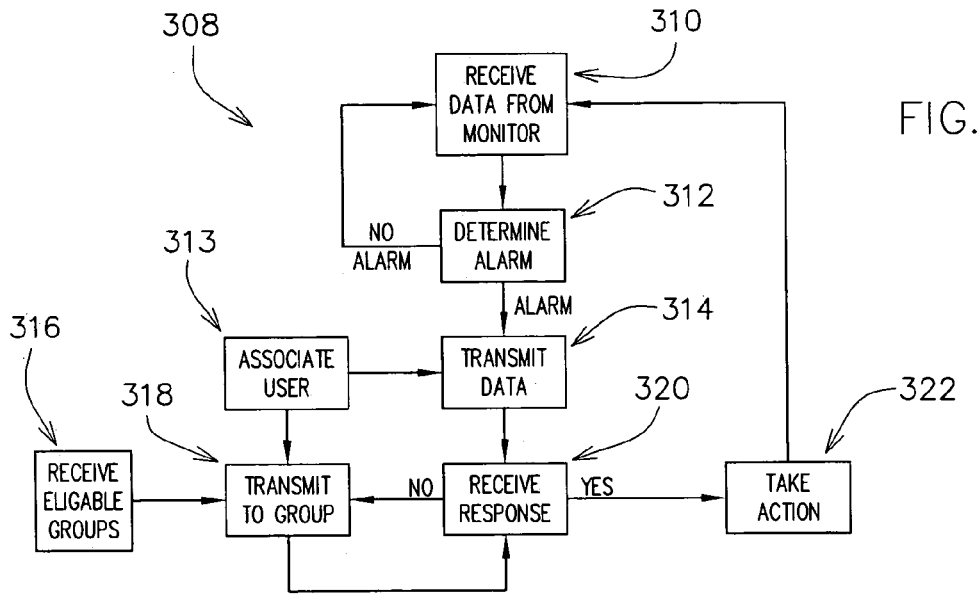
FIG. 4 is a flow chart of server and/or system functions according to one embodiment which may be used in a monitoring system such as that shown in FIG. 1.

Referring to FIG. 4, a method 308 that may be implemented in a monitoring system 10 having a notification feature, such as a monitoring system 10 including a notification server 52 running a notification program, may include receiving data at a monitoring device 14-24 at block 310. Based on the monitoring data received at block 310, a determination can be made at block 312 as to whether a patient being monitored has a condition that may require attention.

If a patient has a condition that may require attention at block 312, then data may be sent at block 314 to caregiver receiver 60 as a notification message in order to alert a user of caregiver receiver 60 of the condition. A notification message can specifically point out that a patient has a condition or the message may be conveyed to a user based on the fact that the user is receiving data relating to a patient. The notification message may be displayed in any number of manners including audibly, visually, etc.

Data may be transferred in parts. For instance, an initial notification message may include the patient's name and a window of data relating to the patient. The window of data may be a 3 to 20 second clip (or, more typically, a 6 to 12 second clip) of data relating to the patient which clip of data represents the state of the patient at about the time of the alarm. The length of the window may be predetermined, may be user selectable, or may vary according to the data relating to the patient. The 3 to 20 second clip may include data acquired shortly before the alarm, data from at the time of the alarm, and/or data acquired shortly after the alarm. The timing of when the data is received may also be predetermined, may be user selectable, or may vary according to the data relating to the patient.

This initial portion of the message may be followed by additional information such as live data (discussed below) relating to the patient. This subsequent portion may be transmitted automatically, or may be transmitted in response to a user request (see block 412 below). If both a window of alarm data and live data are sent, the window data and the live data may be displayed at the same time, or a user may be allowed to switch between the window and the live data.

The caregiver receiver 60 to which the data is transmitted at block 314 may be determined based on an association of a user with a particular caregiver receiver at block 313. Associating a user with a caregiver receiver may occur by way of a program at a workstation (such as central station 46) or may occur based on an input received at caregiver receiver 60. Inputs at caregiver receiver 60 that may be used to associate caregiver receiver 60 with a user could include sensing a unique code associated with a user (such as a barcode or an RFID code), could include an input received from a device inserted into caregiver receiver 60 such as a smartcard or a key, could be based on a biometric input, could be based on a voice identification of a user, could be based on a password input to caregiver receiver 60, and/or could include some other method of input.

Data sent at block 314 can include any of a variety of information. For instance, the data can include a simple warning, can include a patient's name, room number, bed number, pre-selected name (nickname), and/or other patient identification, can include ECG data taken at the time of and following the alarm (for instance 6 seconds of data), can include other physiologic data from the patient being monitored, and/or can include some other information. Data may be sent at block 314 from notification server 52, central station 46, monitoring devices 14-24, and/or some other device. Data may be sent point-to-point from a transceiver to caregiver receiver 60 or may be sent by way of a network 42, 44. The types of data to be sent may be customizable to a particular user and/or to a group (for instance all nurses working in a particular care unit would receive certain types/forms of data).

Data may be sent at block 314 to more than one recipient. If data is sent to more than one recipient, the data may be sent serially (i.e. each receiver is sent a separate message one after the other) the data may be sent as a single broadcast message to a plurality of recipients (multi-cast message), or some combination of these methods may be used. If data is multi-cast and is to be customized for the user, the customization may occur by way of a program running on the caregiver receiver 60 which receives the notification message.

After data has been sent at block 314, the monitoring system 10 may be configured to wait at block 320 for a response from the user (which may occur, for instance, by actuating a control of caregiver receiver 60, monitors 14-19, central station 46, or some other device). If a response is received at block 320, an action may be taken at block 322, and the system may continue to receive data from monitoring devices 14-24 at block 310.

If a response is not received from a user at block 320, the system 10 may be configured to transmit the alarm to a group at block 318. The group to which data is sent may be defined by a user at block 316. Further, more than one group may meet the criteria to receive data at block 318. If this occurs, duplicate entries in the group are preferably removed before data is transmitted at block 318. The caregiver receivers 58-62 to which data is transmitted may be based on an association of the caregiver receiver 60 with a user at block 313.

Determining that there is no response at block 320 may include determining that data has not been received by a caregiver receiver 60 (such as by using a protocol to transmit data that would allow notification server 52 to automatically determine that the data has not been received), by determining that no response has been received from the user within a pre-set period of time, and/or by determining that the recipient(s) are too far away from the patient to handle the condition of the patient if the patient does have a condition that requires attention. Determining that a user is too far away may result in a determination of no response in all situations, or only in some situations. For instance, some alarms may appear to be minor alarms. In these situations a determination may be made that data was received, which would then put the responsibility on the caregiver to forward the data to (or otherwise get in contact with) a closer user if the minor alarm does represent a condition of a patient that requires attention. Determining that the recipient(s) are too far away from patient to handle the condition of the patient if the patient does have a condition that requires attention could include determining a location of the patient, determining a location of the user, calculating an estimated response time (for instance, would the caregiver need to wait for an elevator, go to a different building, etc.), and compare the estimated response time to a threshold for the type of alarm. If the user is too far away, the system may further be configured to not send data to the user at all, and, instead, send the data directly to an appropriate group.

The group (a "group" may include one or more persons) to which the data is sent to at block 318 may be affected by more than a pre-selected transmission sequence. For instance, locations of the eligible potential recipients and the patient may be determined. A potential recipient (or more than one recipient) that is closest to the patient may be selected to receive the alarm. The alarm may also be based on the current status of the caregiver. The status of the caregiver may be determined based on schedule information (which may have been entered at the caregiver receiver using the PDA functionality), may be based on an availability input given by the caregiver (e.g. using a switch or toggle button), may be based on the caregiver's proximity to other patients (close proximity to other patients likely means that the caregiver is less likely to be available), or may be based on other factors.

One potential sequence of groups for a health care facility at block 318 includes first sending data to a nurse/group of nurses assigned to a patient, second, sending data to a nurse manager for the care unit in which the patient is located and/or to all the nurses in the care unit, and third, sending data to the managers of each of the care units, to nurses of all the care units, to nurses of a related care unit, and/or to nurses of care units in proximity to the care unit of the patient.

By using a system with more targeted groups, caregivers will receive fewer irrelevant pages due to a failure of an initial recipient to respond. Further, using more targeted groups (and sending fewer less relevant pages) may encourage better responsiveness because a user will understand that they are being targeted as the most, or one of a limited number of, relevant recipients of the notification message.

A faster determination that no response has been received allows a system to incorporate more layers of groups and still maintain a faster response time. It would be advantageous to have a system that can determine immediately (on the order of a couple seconds or less—preferably in less than half a second) that data was not received by a caregiver receiver 60.

A balancing consideration to making a determination in a shorter period of time is that, when data is received by a caregiver receiver 60, a faster determination that no response has been received may result in a larger number of caregivers receiving a message than is necessary. Timing of the groups may be customizable by a user of the system and may come with default settings.

Figure 5:
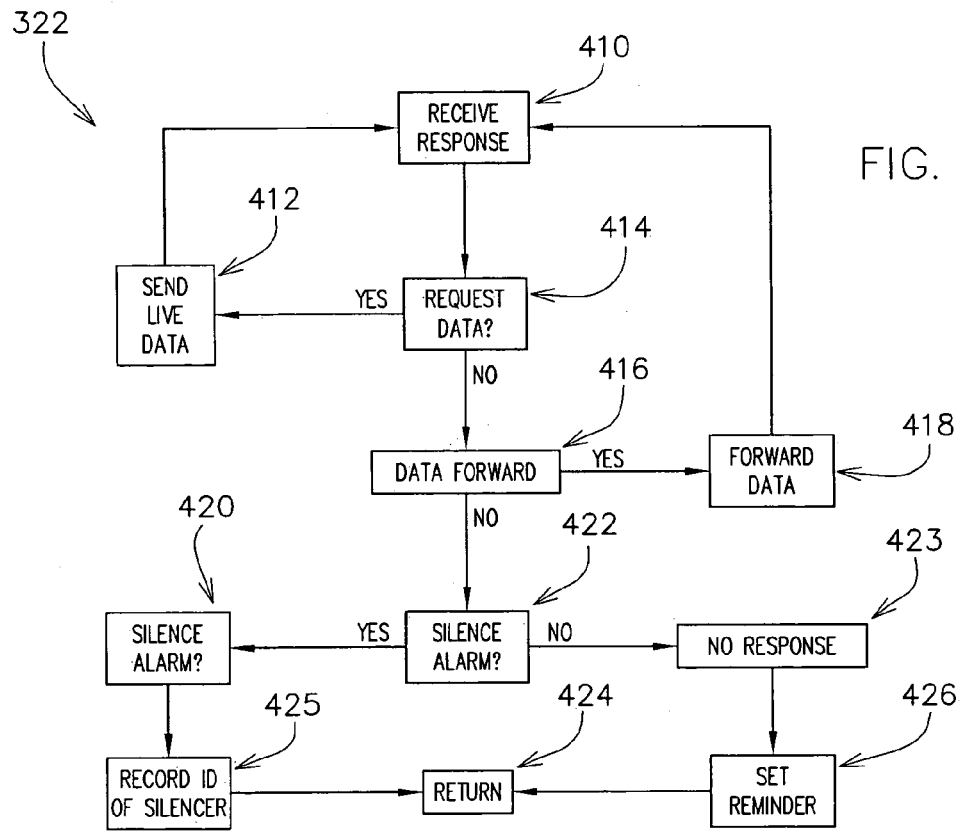
FIG. 5 is a flow chart of server and/or system functions according to one embodiment which may be used in conjunction with the embodiment of FIG. 4.

Referring to FIG. 5, a diagram of possible actions to be evaluated at block 322 include determining at block 414 whether a user has requested that data be sent to caregiver receiver 60, determining at block 416 whether a user has requested that data be forwarded, and determining at block 422 whether a user desires to silence an alarm.

If data is requested to be sent at block 414, data may be sent at block 412. Data sent at block 412 may be live data being acquired from a patient. Live data at block 412 is data that is transferred in real-time or near real-time as it is being acquired. In other words, that patient's waveform and values are being updated dynamically based on the current condition of the patient. Live data should not be construed as requiring that data be received at the recipient device at the same time as it is displayed on a monitor 14-19 since a lag may be incurred due to data transfer methods (for instance, data may be sent in packets of data such as 1 second, 6 second, or nine second packets) and may need to be processed (such as analyzing or formatting the data) by a separate device, such as notification server 52, before it is sent to caregiver receiver 60.

Types of live data that may be requested include ECG waveforms and values, results of data analysis (such as HRT, arrhythmia, HRV, sensor disconnection, and other analysis of data), SpO2 data waveforms or values, cardiac output data, blood pressure data, CO2 data, respiration data, temperature data, and/or other data. A user may choose particular types of data to receive, the system 10 may be configured to transmit the most useful data based on the alarm transmitted, and/or the user may prefer to receive pre-selected sets of data first. Preferably, to facilitate rapid data transfer, not all of the potential monitored parameters are sent at one time. The system may be set such that a certain number of parameters (such as 3 or 5) may be viewed or may be set such that a total amount of data may be selected (some parameters requiring more of the data allotment than other parameters). A common type of data in a Cardiac Step-down Unit would be live ECG data and/or analysis of data relating to a patient's cardiac health (arrhythmia analysis, HRT analysis, HRV analysis, etc.).

Once live data is received on a caregiver receiver 60 a user may take any number of actions. For instance, a processing circuit 156 (FIG. 2) of a caregiver receiver 60 may be configured such that a user may alternate between live data and some other data (particularly, data that was acquired at a time, or about the same time as, when the alarm was triggered. Processing circuit 156 may also be configured to allow a user to pause transmission of live data, go back through data that had previously been received as live, and/or switch the type of data being received.

If a user requests the forwarding of data at block 416, data sent to a caregiver receiver 60 may be sent to a second caregiver receiver 58 or to a different electronic device (such as a cell phone, a PDA, or a computer—notebook, desktop, tablet) at block 418. Caregiver receiver 60 may transmit the data directly to a device within range of a transmitter of caregiver receiver 60, or caregiver receiver may transfer the data by way of a network 42, 44. Alternatively, notification server 52 may receive a request to forward data from caregiver receiver 60 and then transmit data to the second caregiver receiver 58 in response to the request.

All data sent to caregiver receiver 60 may be forwarded, the basic alarm may be forwarded, or a user may be allowed to select which data to forward. For instance, a user may be allowed to set points in a set of live data and only transfer data between two points. As one example, a user may set a start mark in a live ECG waveform that was acquired from a patient/viewed on a receiver at a time T1 and an end mark at a time T2 such that all ECG waveform data between those marks will be transferred. A mark set with respect to one parameter may be carried over to another parameter.

After live data is sent at block 412 and data is forwarded at block 418, the system may be configured to wait for further responses from the user.

If a user requests, using caregiver receiver 60, to silence an alarm at block 422, then the alarm may be silenced at block 420. Silencing an alarm at block 420 may include silencing the alarm locally (i.e. silencing the alarm for that particular user), may include silencing an alarm for the notification system (i.e. stopping the notification system from sending further notification pages for that particular alarm), and may include silencing an alarm for the monitoring system 10 (i.e. silencing the alarm for multiple, and typically all, users of a hospital monitoring system). If a user is able to silence/reset an alarm for the monitoring system by way of caregiver receiver 60, then caregiver receiver 60 may be considered to be a primary enunciator for that alarm. Silencing an alarm at block 420 may include transmitting data to a monitor 14-19, especially where caregiver receiver 60 acts as a primary enunciator. Data may be transmitted to monitors 14-19 by way of notification server 52 and central station 46.

In one embodiment, a user is identified at block 422 when it is determined whether to silence an alarm. In this embodiment, the identity of the user may be determined for purposes of record keeping (and is recorded at block 425). The identity of the user may alternatively (or additionally) be determined to identify whether the user may silence the alarm.

Identifying the user may be accomplished at block 422 by receiving a command to silence an alarm from a caregiver receiver (FIG. 1) that is associated with a particular user. Alternatively, identifying the user may comprise analyzing a spoken command from the user to determine the identity of the user. The user audio input (spoken command) may be compared to data files stored by system 10, and may be compared for particular key words. In still a further embodiment, a user is identified based on one method which may be overridden by an input using a second, different, method. For instance, the system may generally identify a user based on an association of a particular receiver with a particular user, but this identification may be subservient to a spoken command, if one is issued, where the system identifies the spoken command as coming from a different user. If an association is used, the association may need to be verified is some or all circumstances when an alarm is silenced (e.g. by a password, voice match, unique code associated with user, biometric input, etc.).

If an alarm is silenced at block 420 the system may return to the main path for the method 308. If an alarm is ignored then a determination is made that there is no response at block 426. The system may then transmit data to groups at block 318 (FIG. 4).

Method 308 is preferably implemented in a software program running on a processor such as notification server 52, but may alternatively be implemented by other parts of system 10.

Figure 6:
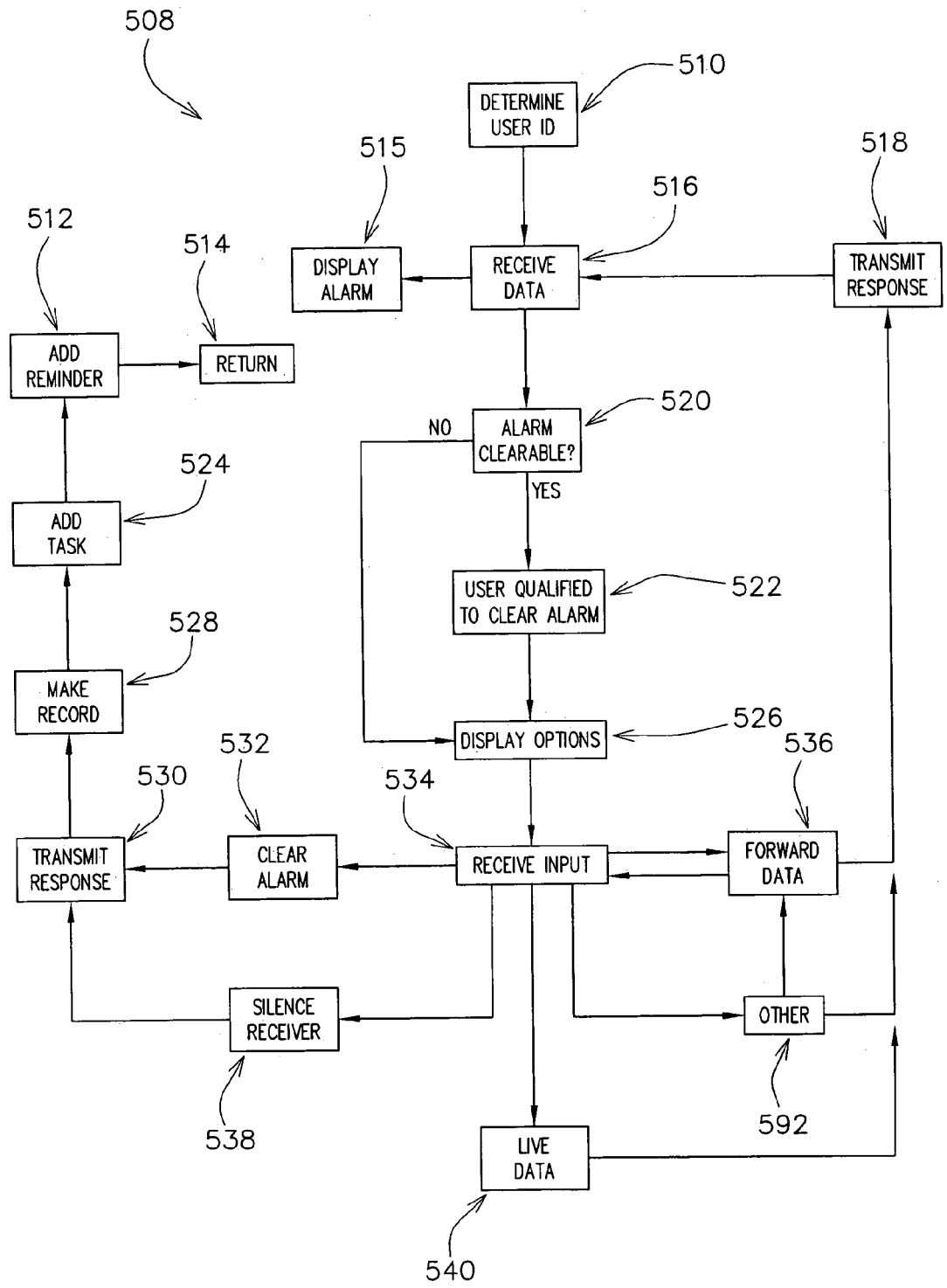
FIG. 6 is a flow chart of receiver and/or system functions according to one embodiment which may be used in conjunction with the embodiment of FIG. 4.

Referring to FIG. 6, a method 508 for implementing a notification feature in a caregiver receiver 60 may include determining the identity of a user at block 510. This identification may be used to determine which data is transmitted to a caregiver receiver 60 and/or how the data is displayed on the caregiver receiver 60. Method 508 may be run as an interrupt that interrupts other programs being run when alarm data is received at block 516. If an alarm is received at block 516, then the alarm may be displayed to a user at block 515. Displaying the alarm to a user may include vibrating the caregiver receiver, may include flashing an LED 142, screen 144, and/or other light source, and/or may include sending an audible signal. The form of the alarm may be adjustable by actuation of a pre-programmed switch.

If an audible signal is used to display the alarm, then the signal used may be customizable by the user. For instance, a user may customize the audible signal such that a different audible signal is used based on the severity of the alarm, based on which patient's physiological characteristics being monitored led to the alarm, based on which patient has the potential condition requiring attention; based on the reason the user is a recipient of the alarm (such as whether they are the primary user receiving the alarm, such as whether they have received the alarm after the primary user has not responded, such as whether another user is forwarding them the alarm, etc.), and/or based on other factors a user may desire to use to customize the alarm.

If caregiver receiver 60 may be a primary enunciator in some instances but not in other instances, then a pair of determinations may be made at blocks 520 and 522. A determination may be made at block 520 as to whether the alarm is clearable using caregiver receiver 60. In some instances, it may not be desirable to clear an alarm without first viewing the condition of the patient (visually, by way of data from multiple monitored parameters, etc.). This may be determined based on the proximity of the user to the patient. Proximity may be determined by whether a short-range link is established between caregiver receiver 60 and a monitoring device 14-24, based on the positions of the user and the patient (which may be determined by a number of methods), or based on some other input. Alternatively, this may be determined when the user clears the alarm using the monitoring device 14-24.

Another determination may be made at block 522 as to whether the user is qualified to clear the alarm using a caregiver receiver 60. The user's identity may be retrieved based on the determination at block 510. In some instances, it may be desirable that a user with a particular level of skill be the only one allowed to clear an alarm using a caregiver receiver 60. The determinations at blocks 520 and 522 may be made based on a type of condition leading to the alarm, based on a severity of a condition leading to the alarm, based on the frequency of alarms for a particular patient, based on configurations of system 10, and/or based on other inputs.

Based on the determinations made at blocks 520 and 522, options are displayed to a user at block 526. Available options may include forwarding data to another user, requesting live data, silencing the alarm at the caregiver receiver, clearing the alarm for the monitoring system, or taking some other action. Options displayed may include forwarding data to a person qualified to silence the alarm for the monitoring system if the user was determined at block 522 to be unable to silence the alarm for the monitoring system. Options displayed may include an icon indicating that the user may not silence the alarm based on the results of blocks 520 and 522 (different icons or a same icon may be used based on the answers to blocks 520 and 522). The available options may be displayed textually and/or graphically.

Caregiver receiver 60 receives a user input at block 534. Caregiver receiver 60 may then send a control signal at block 536 to control monitoring system 10 to forward data, a control signal at block 540 to request live data, or a control signal at block 542 to control some other auction. The control signals are transmitted at block 518 and the system waits to receive data at block 516 or receive further user inputs at block 534.

One possible alternate action controllable at block 542 would be to place a call to another user using caregiver receiver 60. If a call is placed using caregiver receiver at block 542 while alarm data is being displayed on caregiver receiver 60, that alarm data may automatically be forwarded at block 536 to the person receiving the call from the user if the person receiving the call has a means to view the data. Alternatively, a user may forward data to the recipient using a single user input. For instance, a single button or screen area actuated may forward data to the voice call recipient. A single user input may include double clicking a button and/or actuating two buttons at a same time.

Another possibility at block 542 is an indication that the user accepts responsibility for handling the alarm. For instance, if the alarm represents a condition of a patient requiring attention, a caregiver may indicate that they can handle it. By indicating to others that an alarm is being handled (including a minor alarm that does not require further attention), the other caregivers would be allowed to operate more efficiently because they would be able to receive notifications of conditions of patients but be spared from at least some duplication of work.

Still another possibility at block 542 is to set markers in a set of data. Setting markers may be accomplished by any number of methods. For instance, data may be displayed in a graphical manner on a touch display screen. A user may then tap the screen at the point desired to set the marker. As another (or additional) alternative, a user may scroll through the data using buttons/arrows until the point at which the marker is to be set is reached.

Markers could include start and stop markers to identify ranges of interest in the data. Markers may also be set to identify interesting events. Markers may further be set to mark each (or at least a plurality) of parameters viewed on the portable device. In this way, if only a limited number of parameters are viewable at any one time, a user can mark a particular point in time and can then scroll through the various parameters (such as SpO2, ECG, CO, etc.) while maintaining a frame of reference (such as the occurrence of a suspicious event). A user may be able to add text to a marker such that the user may make notes to themselves or others.

If data is forwarded at block 536 after markers have been set at block 542, the markers may also be forwarded in some embodiments.

As yet another possibility at block 542, a user may choose to jump to markers that have been set in the data. In this manner, the display will quickly and efficiently move backward and/or forward through the data in response to a user input at block 534 to the points in the data that a user previously thought to be interesting and worth marking.

As a further possibility at block 542, a user may input a desire to switch parameters viewed and/or scroll in time through the parameters already being viewed. A user may switch all parameters with a single input, may switch selected parameters with an input, or may switch one parameter at a time. The order of the parameters may be preset or may be user configurable. If a user scrolls in time through data received (typically live data) the user may be able to scroll (typically through data acquired live) at different speeds (for instance, based on inputs from different input devices or based on a length of time a signle input is recorded). A user may also be allowed to pause data.

Caregiver receiver 60 may also receive user inputs at block 534 to clear an alarm for the monitoring system at block 532 or to silence the caregiver receiver 60 at block 538. If a user inputs a command to globally clear an alarm, then that request is transmitted at block 530. If a user requests to silence the alarm only at the caregiver receiver 60 at block 538, that request may also (but need not be) transmitted at block 530. The request transmitted at block 530 may be sent to other users of the notification system 64 (FIG. 1) such that the other users know that they do not need to be responsible for responding to the alarm.

Once an alarm has been silenced at the caregiver receiver 60, the caregiver receiver 60 may make a record of the event at block 528 such that a user may review data associated with the event at a later time. These records may be organized by time at which the event occurred, patient for whom the event occurred, or other organizational method. The records may be saved as memos/notes and may be accessible by actuation of a pre-programmed key 106. The record may also be used for billing purposes and/or may be used to help a user reconstruct their day. These records may be combined with other records based on the use of various system functions. For instance, these records may be combined with records of phone usage, which records of phone usage may be associated with a particular patient. Further, these records may be combined with location tracking records such that a user may recreate their steps generally and/or may recreate where they were when an alarm occurred and was silenced.

Also, once an alarm has been silenced at caregiver receiver 60, a task may be added to a task list based on the alarm. For instance, if a user receives an alarm indicating that one of their patients has an electrode, or probe, or other sensor that was disconnected or misaligned, a user may silence the alarm at caregiver receiver 60 at block 538 and then receive the option to add a task to reconnect/realign the sensor for the patient to a list of tasks saved in an organizer program (which may be a function of caregiver receiver 60). Fields for the task may be automatically set by the caregiver receiver (such as the type of task and patient name). A user may also be able to select from a list of tasks which might possibly correspond to the subject. For instance, if the user is a clinician in a Cardiac Step-down Unit, a pair of minor alarms that were likely caused by noise-induced muscle alarm may allow the user to add a task of "check patient X," "check alignment of patient X's sensors," or some other task.

A user may also set a reminder at block 512 once an alarm has been silenced. For instance, a user who forwards data at block 536 to obtain the opinion of another user may silence an alarm at block 532 or block 538 and then set a time-based reminder to re-contact the person to whom data was sent if that person has not responded within a predetermined amount of time. If the person does respond, that reminder may be cleared automatically from the organizer function. As with tasks, fields for the reminders may be set automatically and pre-determined reminders may appear to make it easier for a user to enter a commonly used reminder. Also, with the tasks and reminders, data viewed with the notification message may be attached to the entry made in the task list and calendar. The data may be attached textually or as a link to a file.

Once a user has determined whether to set a task at block 524 and whether to add a reminder at block 512, the notification function 508 may end and the system may return at block 514 to its regular operation.

While tasks and reminders are being shown as options after an alarm has been silenced, various tasks and reminders may be options at other points as well (such as when data is forwarded). Further, while FIGS. 4-6 have been described with respect to a patient monitoring system, other systems (especially other monitoring systems) may implement the features described with respect to FIGS. 4-6. Also, while user identification block 510 is shown as a step taken before an alarm is received, the user identification block 510 may come after the alarm is received. For instance, a user may select an option by speaking a command. Based on the user audio input (the signal representing the spoken command), the system 10 may identify an option selected (thereby controlling a function of notification server 52 based on the audio input), may identify a user, or may both identify the user and the selection. Also, while blocks 520 and 522 are shown as occurring before options are displayed to a user, blocks 520 and 522 may occur after options are displayed to a user. For instance, blocks 520 and 522 may be implemented only after a user chooses to clear an alarm at block 532.

Referring to FIG. 7, a system for transferring data according to one embodiment includes a computer 616. Computer 616 may be notification server 52, central monitor 46, some other processing device, or a combination of these devices. Computer 616 is coupled to a docking station 614 which is configured to receive a user's personal digital assistant (PDA) 612 and/or wireless phone 610. Docking station 614 may also be configured to recharge the batteries of PDA 612 and wireless phone 610. Instead of forming a wired link with PDA 612 and wireless phone 610, docking station 614 may form a wireless link. The wireless link may be a WiFi link, may be a BLUETOOTH link, or may use some other means of data communication.

Data stored on PDA 612 and/or wireless phone 610 may be transferred to computer 616 and stored in an organizer program 624 running on computer 616, and vice versa. Data to be transferred may include schedule information, may include phonebook information, may include task list information, may include notes, may include voice dialing files, and/or may include any number of other types of information.

Data in the organizer program 624 may be accessed by caregiver receiver 60. In one embodiment, data from organizer program 624 is transferred to caregiver receiver 60 when a user of caregiver receiver 60 is identified (which may be automatically if caregiver receiver 60 is assigned to a particular user). In another embodiment, caregiver receiver 60 may not be configured to store the entire files of a user's data in the organizer program. Rather, caregiver receiver 60 may be configured to transfer data from organizer program 624 of computer 616 in response to a user input to view that information. In this embodiment, caregiver receiver 60 may also receive data related to the data requested by the user so that caregiver receiver may be able to respond to further data requests more quickly. Data may be related by function (phone and voice data, task data, memo data), may be related by patient, may have a data-base link, and/or may be related by any other characteristic of the data.

Caregiver receiver 60 may also serve as a wireless phone. Serving as a wireless phone means that voice communication is facilitated by caregiver receiver 60. For instance, caregiver receiver 60 may receive user audio inputs from microphone 146 and output audio data using speaker 148 (FIG. 2). Caregiver receiver 60 and transceiver 618 may be configured to transfer this data between each other.

In one embodiment, caregiver receiver 60 has a wireless transceiver capable of wirelessly transmitting data to docking station 614 (e.g. caregiver receiver 60 transmits data which is received by transceiver 618 which is, in turn, connected to a common hospital network 44 as docking station 614). In this embodiment, docking station 614 may have a processor configured to control wireless phone 610 based on commands from caregiver receiver 60. In this manner, a user may actuate caregiver receiver 60 to place a call using wireless phone 610. Also, docking station 614 may have a processor configured to determine that wireless phone 610 has an incoming call and to transfer that information to caregiver receiver 60 (including other associated information such as the identity of the caller). A user may then use caregiver receiver 60 to answer the call. In this manner, a user may use his or her own personal wireless phone to make and receive calls. This would allow a user to carry fewer devices through the hospital while still having access to his or her personal wireless phone 610. Further, this would allow a user to place the personal wireless phone 610 in a location of a healthcare facility that has reception from a service provider's cellular network and be able to use the phone from anywhere in the health care facility network. This is particularly advantageous for healthcare facilities where the structures are constructed such that cellular reception may be blocked in most areas of the facility and where cellular phones are prohibited in certain areas due to potential adverse effects.

Further, a user may place and receive calls from a wired phone connection 626. The wired phone connection may be made by way of a private branch exchange (PBX). Still further, a user may choose, when placing a call using notification device, to make the call using either the wired phone 626, the wireless phone 610, or some other voice connection type (such as voice over IP). Even further, the system may be configured to choose the proper connection (such as a voice over IP for an in-hospital call if available, a wired phone 626 for a local call if there is a free line, a wired phone 626 for a hospital related long-distance call, and a personal wireless phone 610 for a personal long-distance call).

The system may also include a communication device 620 used to receive and/or output audio data to be transferred in a voice communication application.

While shown as separate components, computer 616 and docking station 614 may be a common device. Further, docking station 614 may be configured to receive caregiver receiver 60 and transfer data using a wired connection. Also, while reference was made to a processor of docking station 614 controlling wireless phone 610, an alternate embodiment could have docking station 614 merely be a conduit for data (or even merely a wireless transceiver) that is controlled by a different processor.

Referring to FIG. 8A, a set of devices for use in a voice communication system include a caregiver receiver 60 configured to transfer voice data between a user 714 of caregiver receiver 60 and another person using a network 716. Network 716 may be a cellular network, a hospital's local area network, a wide area network, or some other network.

The devices may also include a separate speaker/microphone devices 710, 712 configured to receive audio inputs from user 714 and to output audio inputs based on data received from caregiver receiver 60. Speaker/microphone devices 710, 712 are preferably hands-free communication devices 710, 712 comprising a microphone and a speaker in a common housing that is configured to be placed in a proper position for audio communication without requiring a user to hold the device. Communication devices 710, 712 may be connected to caregiver receiver 60 by a physical connection or by way of a wireless connection. If communication devices 710, 712 are configured to make a connection by way of a wireless connection, communication devices 710, 712 may include a short-range link transceiver. The short-range link transceiver of communication devices 710, 712 may use BLUETOOTH technology as discussed above for short-range link transceiver 122 (FIG. 2) of caregiver receiver 60. Data may be transferred wirelessly from communication devices 710, 712 to caregiver receiver 60 which processes the data and transfers the data to network 716, and vice versa.

Communication devices 710, 712 may include one or more user input devices (such as a power switch, volume buttons, a link establishing button, etc.). If communication devices 710, 712 are wireless, they may be configured to be associated or capable of being associated with a particular caregiver receiver 60 to prevent communication devices 710, 712 from accidentally receiving and transmitting data to other devices. Communication device 712 is configured to be attachable to a user's 714 clothing. Attachment means may include a hook and loop type fastener such as VELCRO, a pin, a button, or some other means of attachment. Communication device 710 may be configured to be attached to a user, such as an ear-bud speaker with a microphone supported by a housing that is, in turn, configured to be supported by a user's ear.

Figure 8B:
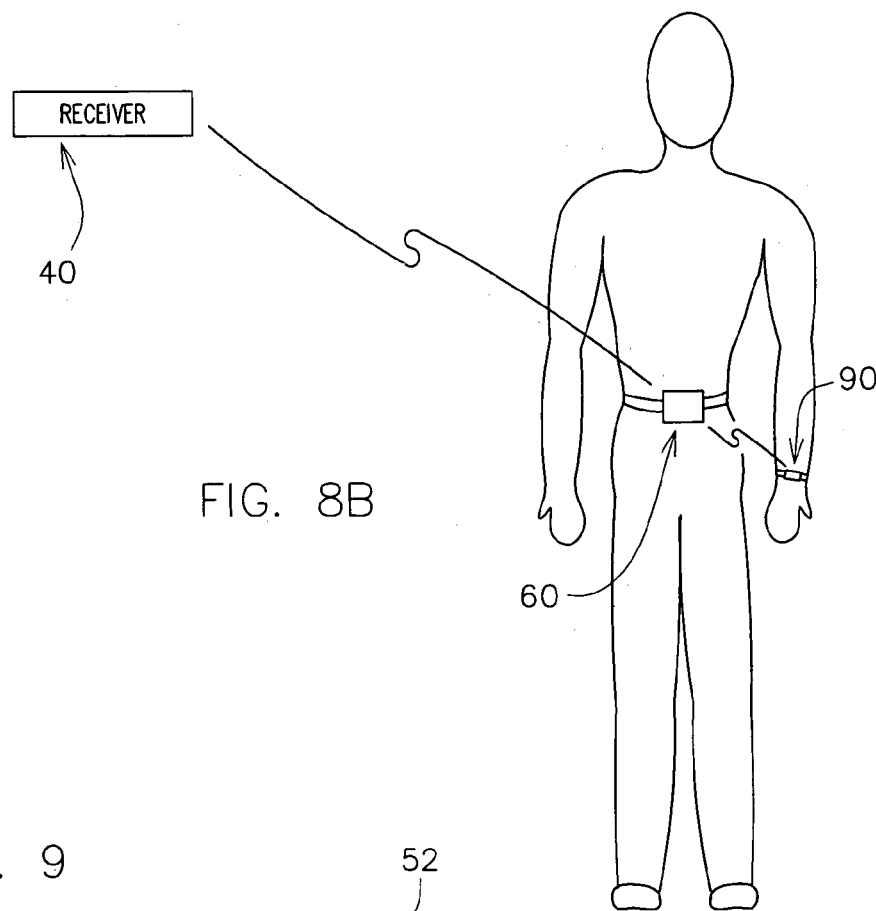
FIG. 8B is a diagram of a notification system that may be used by a user which may be used in conjunction with the system of FIG. 1.

Referring to FIG. 8B, caregiver receiver 60 may be configured to work with a peripheral device 90. Peripheral device 90 may have a band and may be configured to be attached to a user's limb (such as attaching to a wrist like a watch). Peripheral device 90 may include a display/touch screen which may display data to a user. Peripheral device 90 may also include a transceiver (preferably a low-power transceiver such as a short-range link transceiver). The transceiver may use a wireless protocol such as an IEEE 802 wireless protocol or a BLUETOOTH™ protocol. Peripheral 90 may also include a speaker, a microphone, a vibrator, a biometric input, and an accelerometer.

Caregiver receiver 60 may receive data (such as an alarm) from a transceiver (such as notification transceiver 40) and communicate that data to peripheral device 90 where a user may quickly view that data. Alternatively, peripheral device 90 and caregiver receiver 60 may be a same device.

If peripheral device 90 includes an accelerometer, the accelerometer may be used to control functions of peripheral device 90, particularly notification functions. For instance, if an alarm is received from notification transceiver 40 and is displayed on a display screen of peripheral device 90, the system may be configured to monitor the outputs of the accelerometer for movements representative of a user turning his or her wrist to view the display screen of peripheral device 90 and then placing his or her arm back down to the side. If this motion is detected, the alarm may be silenced for that user.

Figure 9:
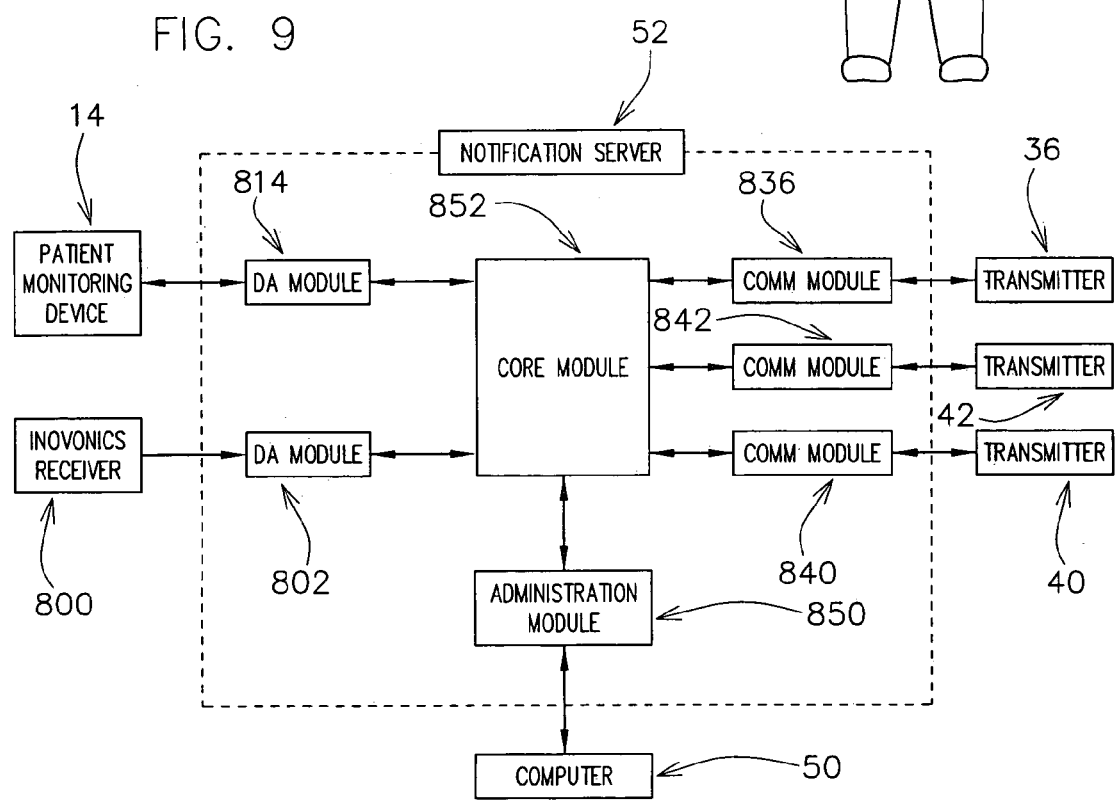
FIG. 9 is a diagram of a server of a notification system according to one embodiment which may be used in conjunction with the system of FIG. 1.

Referring to FIG. 9, a notification system 64 of the patient monitoring system 10 (FIG. 1), converts the data to an appropriate form, and sends the converted data to the caregiver receivers 60 in a typical embodiment. In one embodiment, the alarm notification, system 64 includes a notification server 52 which includes data acquisition modules 814 that collect data from the patient monitoring system 10 data acquisition modules 814 may collect data from a wireless receiver or a wired tap into the patient monitoring system 10. Notification server 52 may be required to use more than one data acquisition module if more than one brand of monitoring device 12-24 is used.

Data collected by data acquisition modules 814 is sent to a core module or computer system 852 that analyzes the collected data and determines what information should be sent to the caregivers. The core module 852 may be required to perform a conversion of the data, such as the conversion of an ECG waveform to binary data representing the waveform.

Also, notification server 52 may include a number of communication modules 836-842 which may be utilized to send the data from the core module 852 to individual caregiver receivers 58-62 by way of transmitters 36, 40, 42. Different communication modules may be needed for communicating with transmitters that use different protocols and/or technologies. Alternately, a single communication module may be used to communicate with all of the transmitters 36, 40, 42.

Notification server 52 may further include an administration module 850 configured to operate the administrative features of notification system 64. Some administrative features include setting up which monitoring devices will be monitored by notification system 64, assigning caregivers to patients (or vice versa), setting up acceptable communication paths and settings, setting up which alarms will result in notification messages, setting up which physiological characteristics to monitor, adding caregivers and caregiver receivers, determining which users may use a caregiver receiver as a primary enunciator and under which circumstances (which may effect blocks 520 and/or 522 of FIG. 6 below), and other administrative tasks.

Computer 50 may be used to access and control administration module 850. Administration module 850 may be configured such that computer 50 may use a web browser to access the functions of the module. Computer 50 may be able to access administration module 850 by way of a network, including a local area network (wired or wireless), a wide area network (including the Internet), and/or some other network. Any number of devices could operate as computer 50, including caregiver receivers 58-62, if the device 50 and administration module 850 are configured to allow such access.

While FIGS. 7, 8A, 8B, and 9 have been described with respect to a patient monitoring system, novel aspects of the embodiments described with respect to those figures may be incorporated in other systems—especially other monitoring or communication systems. Further, while the components are shown in a particular arrangement, it should be understood that each of the various components of these systems may be rearranged. It should also be understood that some items shown individually may have their function separated between two or more devices and others shown separately may be combined in a single device. For instance, docking station 614 may actually be two docking stations—one for the PDA and another for the phone. Reference in the claims to one component (such as "a docking station") should not be construed to mean only one component unless otherwise recited by the claim.

Figure 10A:
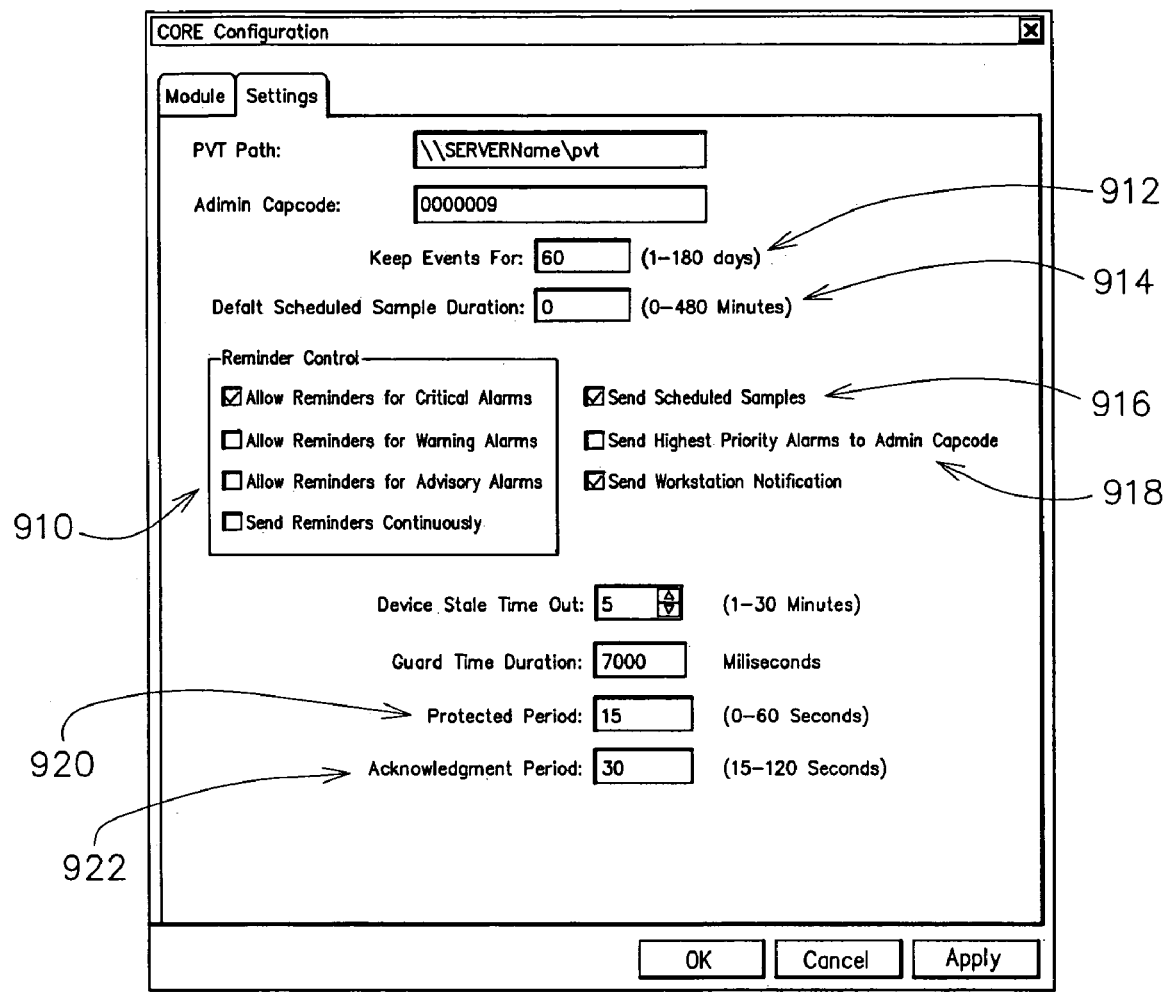
FIGS. 10A-C are exemplary user interfaces for configuring a notification system according to one embodiment which may be implemented by the server of FIG. 9.

Referring to FIG. 10A, a user interface for controlling some of the administrative functions which may be implemented by administration module 850 of notification server 52 includes a reminder control section 910. Reminders may be sent to users of notification system 64 based on the selections made by a user in reminder control section 910. Reminders may be controlled based on any number of factors and may include controlling whether to send reminders based on a severity of the condition leading to the alarm. Severity may be grouped into critical alarms, warning alarms, and advisory alarms. Critical alarms are the most serious alarms and may include events such as asystole, ventricular fibrillation, and called crisis, red, or other life threatening events on monitoring system 10. Warning alarms are a level of alarms below critical alarms and may include events such as non-life threatening arrhythmia, parameter limit alarms, called warnings, yellow, or other serious alarms on monitoring system 10. Advisory alarms are the next lower level alarm and may include events such as leads off, equipment/system warning alarms, patient connection alarms, and called advisory or INOP alarms on a monitoring system.

Other control options may include the duration for which a record is kept at entry 912 and the default scheduled sample duration at entry 914. These entries may have minimum and maximum values to prevent unintended values from being entered.

Additionally control options include controlling at entry 916 whether scheduled samples (e.g. samples of patient physiological data acquired at scheduled periods) may be sent to caregiver receivers of the system, and controlling at entry 918 whether highest priority alarms are initially sent to a group larger than (or in addition to) the primary receivers of alarms for a particular patient (e.g. sending an alarm to the entire group of caregivers in a particular care unit if an alarm is critical).

The user may also set a protected time between when the caregiver receiver receives an alarm and when the notification program of notification server 52 will accept acknowledgement of the alarm at entry 920. This may protect against accidental acknowledgement of the alarm by a caregiver. A user may also set an acknowledgement period which is an amount of time that a system will wait for a response from a caregiver receiver that has been determined to have received the alarm before taking further actions (such as transmitting the notification message to groups)—see blocks 318 and 320 of FIG. 4.

Figure 10B:
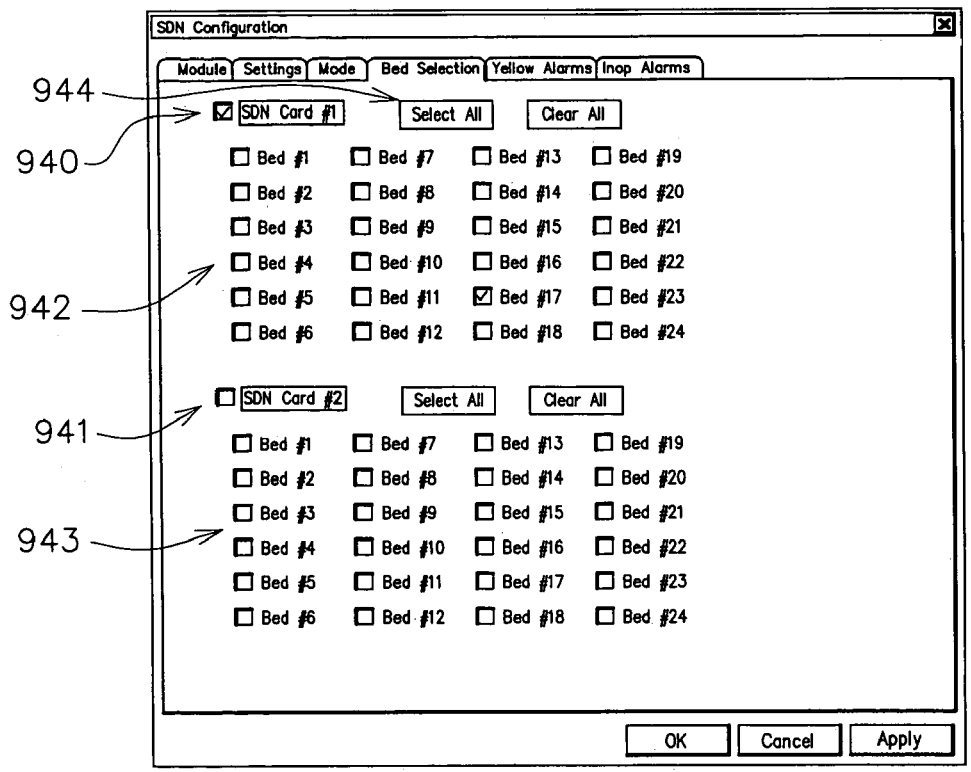

Referring to FIG. 10B, a user of notification system 64 may set which patients are to be monitored by the notification system 64. The user may make certain groups of patients eligible by selection at entries 940 and 941. The user may also select which individual patients (here, represented by bed # to which the patient would be assigned) may be monitored at entries 942 and 943. Certain entries may be excluded based on the selection at entries 940 and 941. A user may also select an entire group at block 944.

Figure 10C:
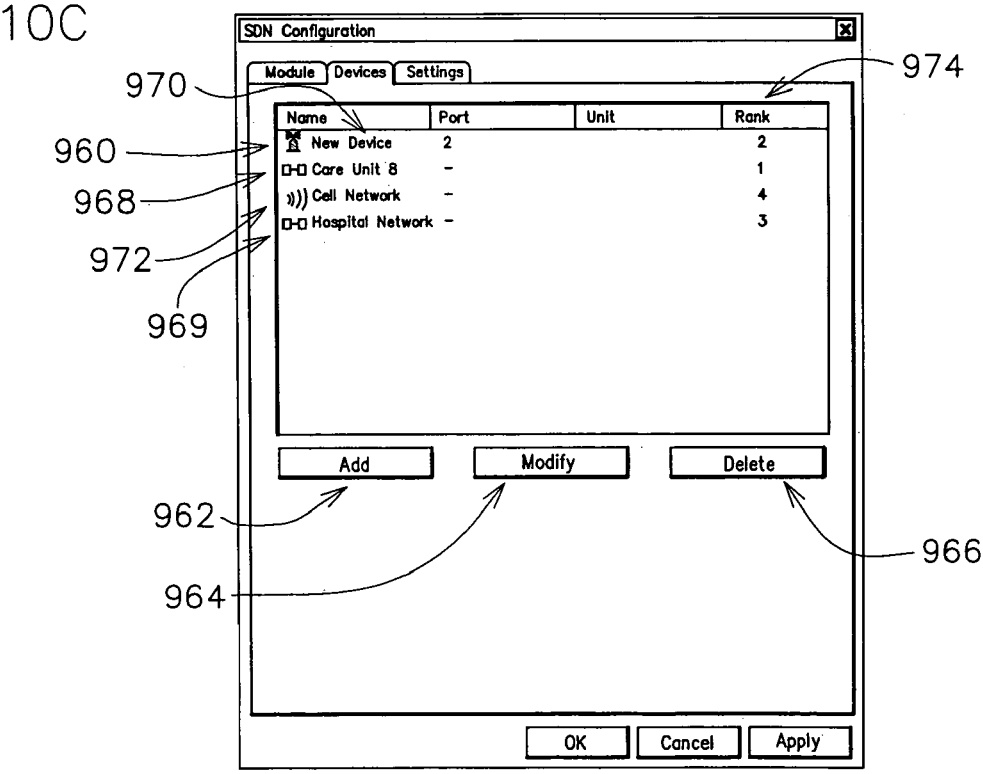

Referring to FIG. 10C, a list of wireless devices that may be used to transmit notification messages may be selected at administration module 850. A list of current used devices 960 may be displayed to a user. The wireless devices to be used can include any of those listed above with respect to FIG. 1. The list may include a local area network 969 or a portion of a local area network 968. The list may include a point-to-point transmitter 960 such as notification transmitter 40. The list may additionally include a cellular network 972. The order in which a system uses the various transmitters may be configurable at option 974. A user may configure a system to primarily use the local area network wireless access points located in the care unit with which a patient is associated, a point-to-point transmitter if the local area network is unavailable, a hospital network as a third option and a cellular network as a fourth option. The availability of a mode of communication, as discussed above, may be determined before a notification message needs to be sent or may be determined based on whether data is received.

A user may be allowed to add, modify, or delete the list of usable wireless devices and their associated properties.

Referring to FIG. 11A, a user may configure administration module 850 to transmit notification messages to proper recipients. Administration module 850 may be configured in this manner from computer 50 and may be controlled from caregiver receiver 60. If control is allowed from a caregiver receiver 60, then a user of caregiver receiver 60 may only be allowed to change settings related to the caregiver currently associated with the caregiver receiver. Settings may include assigning the caregiver to particular groups and to particular patients. Settings may also include changing the responsibility for a patient for whom the caregiver is designated as a recipient of notification messages.

A first display screen available to a user may include a list of caregivers 1402 associated with the notification system. List 1402 may include a name for the caregiver 1404, a number/address 1406 of the caregiver receiver 60 with which the caregiver is associated, a designation 1408 of the unit with which the caregiver is associated, an entry for additional devices 1410 associated with the caregiver, and control options 1412 for the user with respect to each caregiver. Control options 1412 with respect to individual caregivers may include options to page the caregiver, change the name or other properties of the caregiver, assign patients to the caregiver, and schedule periodic patient data samples of a patients physiologic data to be sent to the caregiver.

List 1402 may include a list of individual caregivers and may include a list of groups. The list may be organized such that the individual caregivers always appear before the groups, or may have some other organization. Here, groups can include a group of every caregiver ("everyone") or may include a smaller group ("Group 1"). Smaller groups may have additional options 1412 that the omnibus group does not have associated with it.

A user may also have more global options such as an option 1414 to go to a caregiver setup menu, an option 1416 to clear assignments for all caregivers, and an option 1418 to go to a group setup menu.

Referring to FIG. 11B, a caregiver setup menu includes a list of caregivers 1420 already in the system. List 1420 may be a display of those users which are currently active (currently associated with a caregiver receiver) or may include all caregivers entered in the system. Information which may be displayed may include caregiver names 1404, receiver associated with the caregiver 1406, unit to which the caregiver is assigned 1408, other devices associated with a user 1410, and options associated with the caregiver 1422. Options 1422 may include an option to remove a caregiver and an option to edit a caregiver. A user may also be allowed to add caregivers by actuating an add caregiver control option 1421.

Referring to FIG. 11C, actuation of an add caregiver control option 1421 may bring up an additional screen to input information regarding the caregiver. The information to be added could include a name for the caregiver 1424, the identity of the caregiver receiver 60 associated with the caregiver 1426, the unit to which the caregiver is assigned 1428, any additional devices associated with the caregiver 1430, and the groups to which the caregiver belongs 1432.

The identity of the caregiver receiver 60 associated with the caregiver 1426 may be variable and may be a field that is filled in when a caregiver receiver 60 is associated with a caregiver at the caregiver receiver (e.g. biometric ID, password, unique code associated with caregiver, etc.).

Groups to which the caregiver belongs 1432 may be used to facilitate a paging order for a patient. Associating a group with a patient would then also be associating the caregiver who belongs to the group with the patient. Some groups may be added automatically based on the entry 1428 for the unit with which the caregiver is associated. For instance, an entry of LAB1 in the unit entry 1428 may result in an automatic association of the caregiver with group "LAB1-All" which would be a group comprising all of the members of LAB1. Groups may also be added from a list of available groups 1434. Assigning a caregiver to a group from list 1434 may comprise highlighting the group in list 1434 and actuating an assign caregiver control option 1435. The groups listed as available in list 1434 may be affected by entry 1428 indicating the unit with which the caregiver is affiliated.

A use may also have an option to set information for identifying a caregiver by actuating control option 1427. Information that may be used to identify a user may include biometric inputs such as a fingerprint identification, a unique code associated with the caregiver such as an RFID code or barcode, a password, a voice pattern or code word data, etc. The information entered may then be used to later associate a caregiver receiver 60 with the profile for the particular caregiver.

Figure 11D:
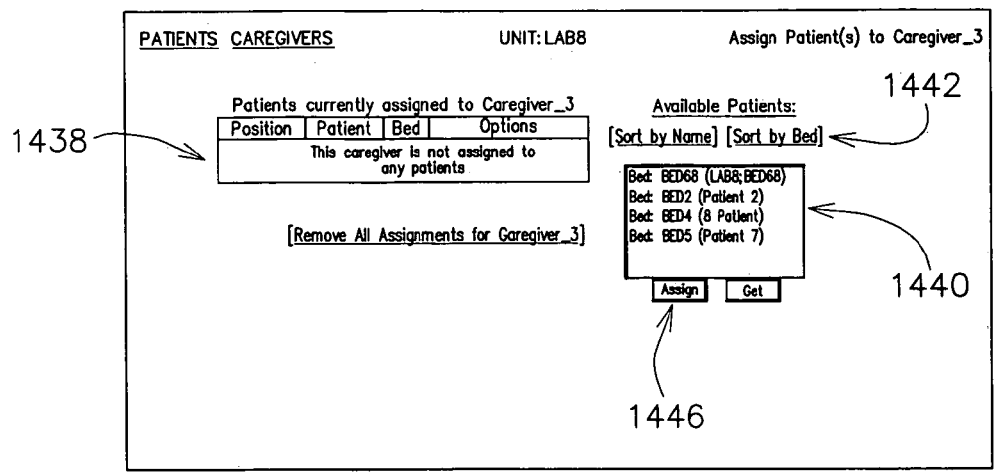

Referring to FIG. 11D, a user interface that may be used to associate patients with particular caregivers includes a list of patients already associated with the caregiver 1438, a list of available patients 1446, control options to sort available patients 1442. A user may assign patients to a caregiver in a same manner discussed above with respect to assigning groups to a caregiver in FIG. 11C. Available patients in list 1440 may be obtained from information directly entered by a user in notification system 64, or may be obtained from data acquired from some other part of system 10 such as from monitors 12-19 (adding available patients when monitoring devices 12-19 are associated with a patient). List 1440 may also be affected by which unit a particular caregiver is associated. Further list 1440 may be sorted by patient name, patient bed #, unit in which a patient is located, and/or other information. A user may also request that the system get more patients to be added to the list (e.g. from other care units).

Figure 11E:
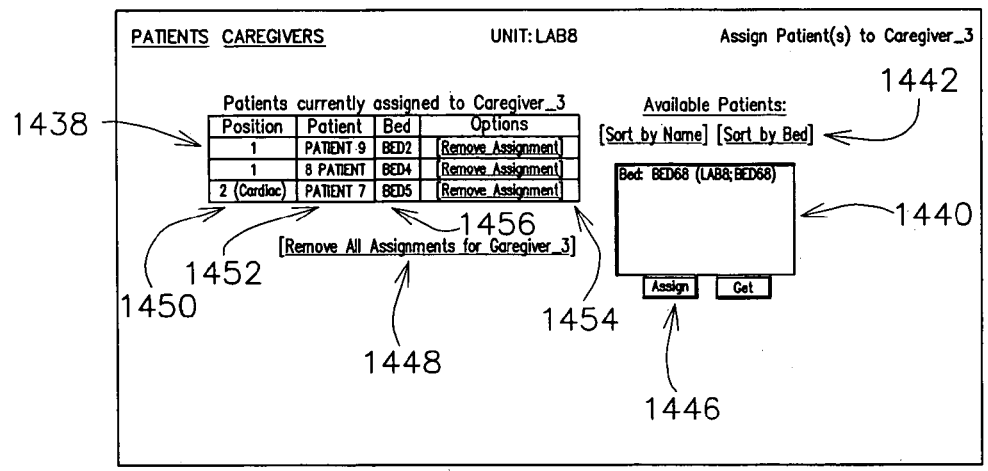

Referring to FIG. 11E, once patients are assigned to a particular caregiver, the patients name 1452 is displayed on list 1438. Additional information that may be displayed in list 1438 includes a patient's bed number 1456, and options 1454 associated with the patient such as removing the assignment of the patient to the caregiver. An option 1450 may also be used to assign a user as a primary recipient of notification messages from a patient or a secondary recipient of messages. Most individual users will generally be a primary recipient (since secondary recipients will most likely be chosen to be groups). Patients with which the caregiver is affiliated based on the caregiver's affiliation with a group may also show up in list 1438 and may include the caregiver's position 1450 by virtue of the group and may include a reference to the group assigned to the patient. Once patients are assigned to a user, those patients may be removed from list 1440.

A user interface similar to that shown in FIGS. 11D and 11E may be used to assign patients to groups. Further, a patient may be assigned to a particular group based on the unit in which the patient is located and/or the unit which a primary recipient of notification messages from the patient is associated. For instance, if a patient is assigned to a bed # located in a critical care unit, the "critical care-all" group may be automatically assigned as a secondary or tertiary recipient of notification messages relating of that patient. Also, if a nurse from a cardiac step-down unit is assigned to the patient as a primary recipient, a group called "cardiac step-down-all" or "cardiac step-down-team 1" may automatically be assigned as a secondary or tertiary recipient. A user interface for the group may also show which caregivers belong to the group an option to add or remove caregivers from the group.

Figure 11F:
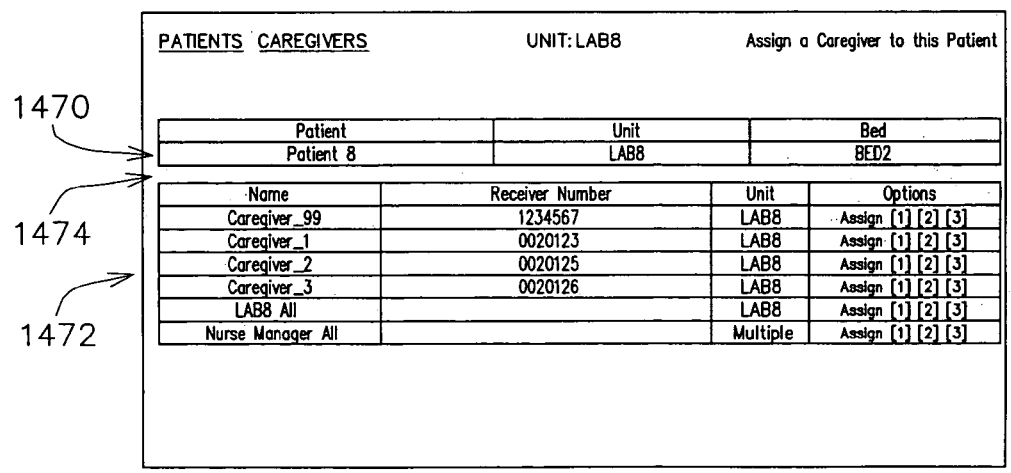

Referring to FIG. 11F, assignments may also be viewed and made on a patient-by-patient basis. A list 1474 of caregivers and caregiver groups associated with the patient may be listed under a patient identifier 1470. List 1474 may include which caregivers and groups are associated with the patient and what their order ($1^{st}$, $2^{nd}$, $3^{rd}$, etc.) is with respect to receiving pages. List 1474 may also include information associated with the caregiver including an option to contact the caregiver.

The user interface may also include a list of available caregivers and groups 1472. List 1472 may include information relating to the caregiver/group such as name, receiver number associated with the caregiver, unit to which the caregiver belongs, and options associated with each caregiver. One option may be to assign a caregiver to the patient which may be divided into sub-commands to assign the recipient level of the caregiver (such as a primary, secondary, or tertiary recipient) of notification messages for the patient.

Figure 12B:
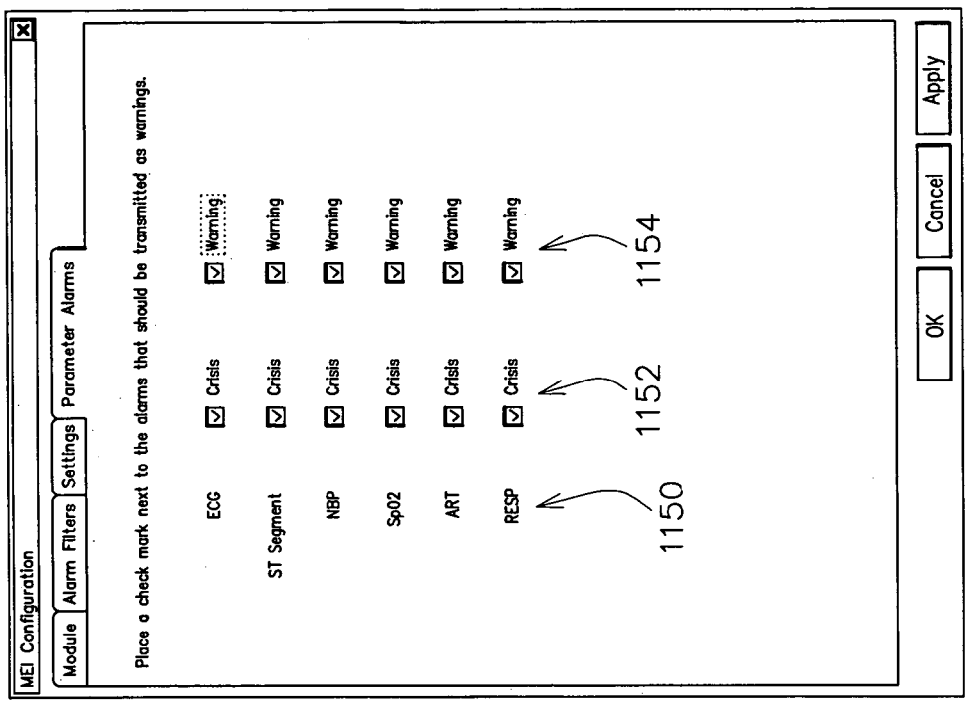
FIGS. 12A-B are exemplary user interfaces for controlling parameters monitored by a notification system according to one embodiment which may be implemented by the server of FIG. 9.
Figure 12A:
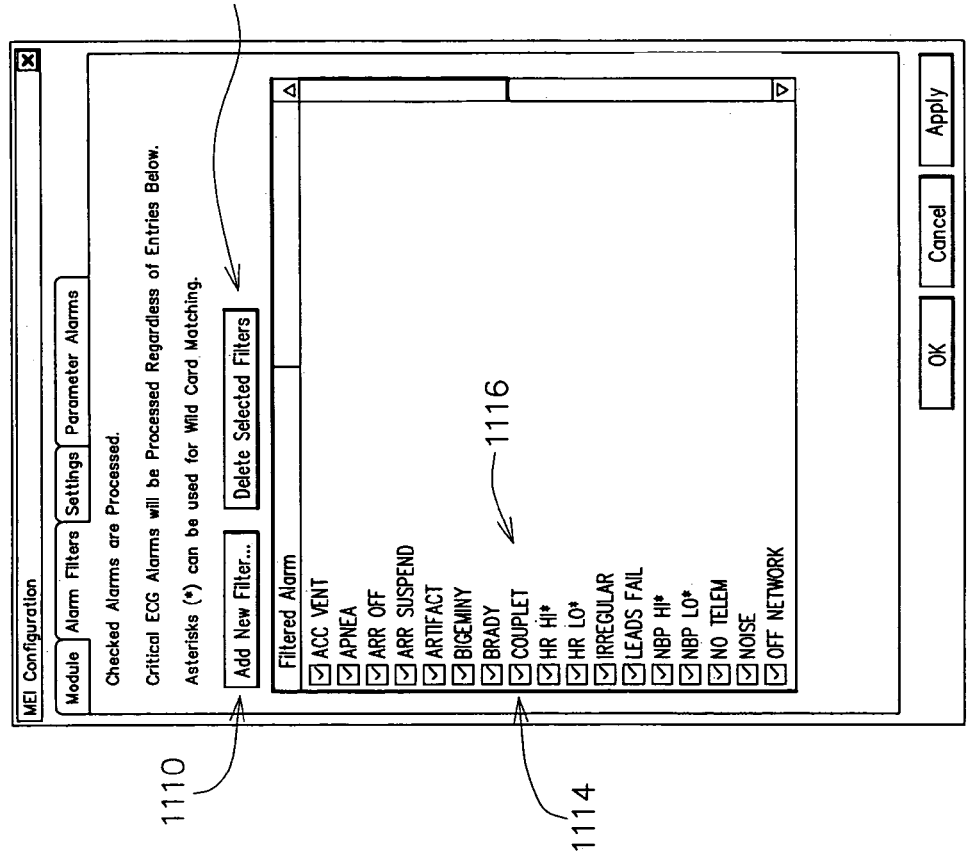

Referring to FIG. 12A, the filters used by notification system 64 may be controlled. A user interface may include a list of filters 1116 which may be selected using an entry 1114 such as an entry that is either checked or unchecked. The user interface may also include an option 1112 to delete filters and an option 1110 to add a new filter.

Referring to FIG. 12B, the parameters monitored by notification system 64 may be controlled by a user. A user interface may include a list 1150 of parameters that may be monitored, an entry 1152 for alarms of a first severity, and an entry 1154 for alarms of a second severity. The user interface may include additional entries for additional alarm severities and/or a more detailed list of criteria for selecting when a notification message will be sent for a parameter.

The user interfaces described with respect to FIGS. 12A and 12B may be used for the entirety of notification system 64, for the entirety of subsystems of notification system 64 (such as individual care units), or for individual patients or caregivers. Alternately, these user interfaces may be used to set defaults for particular systems or sub-systems which may then be modified for a particular patient or care unit.

While FIGS. 10A to 12B have been described with respect to a patient monitoring system, novel aspects of the embodiments described with respect to those figures may be incorporated in other systems—especially other monitoring or communication systems. Further, while reference has been made to a nurse as a caregiver and many of the paging structures have been described with respect to nurses, it should be understood that a caregiver could include other clinicians as well (such as doctors) and need not include nurses.

Also, the various functions listed above for the various user interfaces may be carried out by user interfaces taking numerous other forms. Further, while some user interfaces are shown as being separate screens, the functions of those interfaces may be combined. Further still, while some screens are shown as having numerous functions, those functions may be divided between multiple screens. Reference in the claims to a user interface should not be construed as requiring a single screen implementing each of the functions of the user interface unless otherwise required by the claim.

Figure 13:
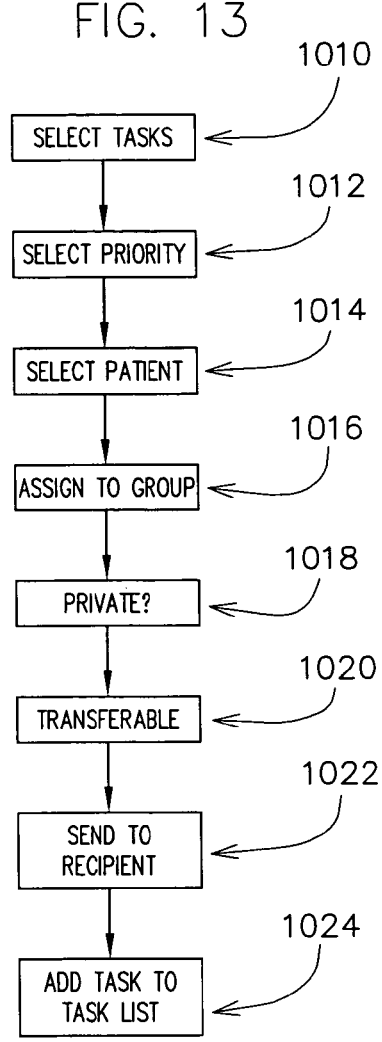
FIG. 13 is a task list generation flow chart according to one embodiment which may be used in conjunction with the embodiment of FIG. 4.

Referring to FIG. 13, a method for adding tasks (and/or reminders) in a system operating in a health care facility includes inputting a task at block 1010. This could include manually inputting data for the task or could include selecting the task from a list of commonly used tasks. The task may be added in response to a voice command to add a task. Common tasks for nurses in a hospital include administering and adjusting medications; assessing for side effects of medications; monitoring the ECG and all applicable vital signs; analyzing and notifying physician of changes in patient condition; assessing multiple body systems; adjusting medications as ordered and needed; administering treatments such as dressing changes, blood transfusions, and other treatments; assisting with activities of daily living as needed; providing emotional support for the patient and family; documenting assessment, daily activities, and other interaction with the patient and family, and planning for discharge from the hospital. The task may be entered at the caregiver receiver 60, at a central station 46, at a monitor 14-19, or at some other device coupled to the caregiver receiver 60. The task may also be entered automatically based on a patient's treatment schedule (such as taking medicine at set intervals).

Once a task is selected at block 1010, the task may be assigned a priority at block 1012. The priority may be fixed, or it may be set to increase over time if it has not yet been completed. The rate at which the priority increases may be set by a user, may be pre-selected, and/or may have a default setting based on the type of task (e.g. a hospital may desire that certain tasks are completed within a certain timeframe).

A task that has been selected at block 1010 may be assigned to a patient associated with the user. If a limited number of patients are associated with the user, this may allow a user to more quickly enter a relevant field into the task list.

A task selected at block 1010 may be assigned to more than one clinician within a health care facility. For instance, a team of nurses may be assigned to take care of a group of patients. A task that is selected at block 1010 may be assignable to the entire team. The task may be set such that each member of the team receives the task and when one member of the team clears the task, the task is cleared for each team member who received the task. If a group approach is taken, the task may have two settings for completeness—in-process and completed. The in-process setting may be used to clear the task from other members of the group and the completed setting may clear the task from the user's list.

A task selected at block 1010 may also be designated as private at block 1018 such that no other user may receive access to the task. Examples of tasks that a user may desire to designate as private would includes tasks a user enters that are unrelated to work responsibilities (paying bills, social schedule, etc.). Tasks designated as private may be transferred to a user's personal PDA 612 (FIG. 7) when a user logs off of caregiver receiver 60 (or at periodic intervals, on request, etc.). Also, a user may be able to designate which tasks to transfer to their personal PDA and which not to transfer independently of other designations.

A task selected at block 1010 may be designated as transferable at block 1020. A transferable task would be a task that would be transferred to another person upon occurrence of an event. A first type of transferable task may be a task that requires a first user to complete one task before a second user can complete a second task. When the first user indicates that they have completed the first task, then the second task is automatically added to the second user's task list. This may be used for obtaining lab results (where a nurse would indicate that lab results have been obtained, and then a doctor would receive a task of checking in on a patient). A second type of transferable task would be a task that is transferred to a user's replacement when the user's replacement arrives. These tasks are tasks that may be completed by either the user or the user's replacement and that have a shorter deadline to be completed. This may save time in explaining what needs to be done.

Once selections have been made for the task at blocks 1010 to 1020, the task may be sent at block 1022 to any appropriate devices as is necessary. Caregiver receiver 60 may alert a user to an arrival of a task sent to it by another device. Also, the task (entered at caregiver receiver 60 or received by caregiver receiver 60) may be added to the task list of caregiver receiver 60.

The tasks saved on caregiver receiver 60 may be arranged by patient, by priority, by personal tasks and group tasks, and/or by some other method.

The task list may also be used to maintain records. For instance, notes may be added to a patient's medical record based on the tasks completed. If the record is an electronic record, the task may be added as an entry in the record. If the patient record is a paper record, then tasks completed may be printed off automatically or periodically such that they may be added to the patient's record.

Figure 14:
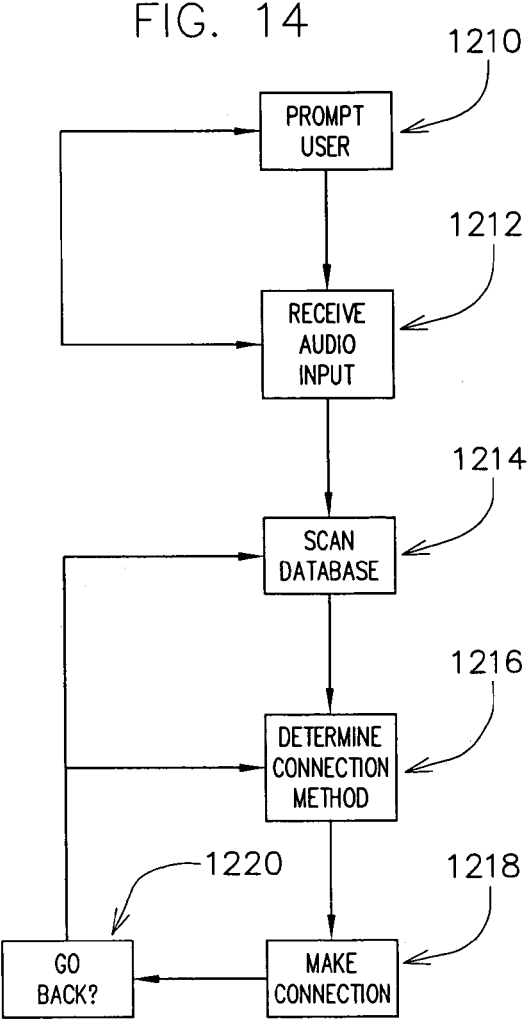
FIG. 14 is a flow chart of phone functions according to one embodiment which may be used in conjunction with the embodiment of FIG. 4.

Referring to FIG. 14, a voice-activated calling method that may be implemented in a health care facility includes prompting a user at block 1210 for an input. The audio input may be received at block 1212. If more information is needed (for instance if the phone system operates in a hierarchy such as personal/business then department then position/name, etc.) then a user may be prompted for more information at block 1210. A user may contact another person based on their name, or they may attempt to contact the appropriate person based on the person's position (such as radiology technician). Prompting a user for information may include a simple tone, an image on a display screen, instructions, etc.

Once sufficient information is obtained at block 1212, the program is set to scan a database at block 1214 for the person the user is attempting to contact. Scanning may include finding the person's entry if a name is entered and/or may include finding an appropriate person if a position is entered. Finding an appropriate person may include searching for the person assigned to the department to which the caller belongs, may include determining which person is available, may include determining which person is on-call, and/or may include some other search.

Once the appropriate person to be contacted is determined at block 1214, the system may determine the appropriate connection method at block 1216. The appropriate connection may be voice-over-IP, may be a land line, may be a cellular line, and may be a user's personal phone.

Once the appropriate connection is determined, the system may attempt to make the connection at block 1218. If a connection cannot be made at block 1218, then the system may be configured to go back to block 1216 or block 1214 to find a different connection method and/or different person to contact. The system may be configured to only re-determine the appropriate person/connection if a user requests that the system redo the determination.

This method may be implemented in a caregiver receiver 60 (FIG. 1), but may also be implemented in a processor of a hospital system 10 (FIG. 1) that the caregiver receiver 60 may contact. In this manner, the caregiver receiver 60 may use less memory without losing functionality while it is within the hospital system.

Figure 15:
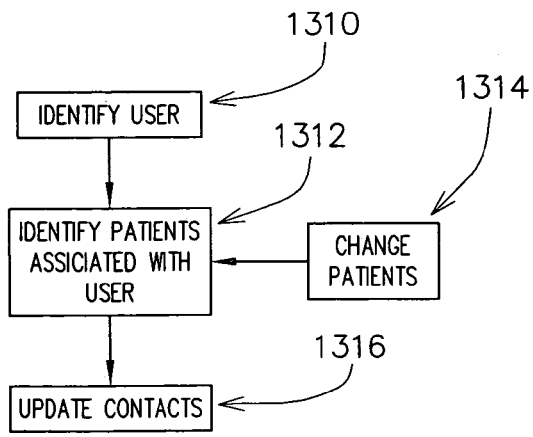
FIG. 15 is a flow chart of a contact list function according to one embodiment which may be used in conjunction with the embodiment of FIG. 14.

Referring to FIG. 15, a method of organizing a user's contacts on a caregiver receiver 60 (FIG. 1) includes identifying the user at block 1310. Once a user is identified, a determination is made at block 1312 as to which patients are associated with the user. The determination of block 1312 may be influenced by a database (such as a hospital's record database) containing information regarding which patients are associated with the user. In this manner, shortly after a patient is discharged from the hospital's system, they may be removed as a patient associated with the user.

Once the patients associated with the user have been determined at block 1312, the contacts in the user's organizer program may be updated. For instance, contacts may be added for patients that are added and removed for patients that are discharged. Contacts that may be added/removed may include a contact for the patient's primary physician, treating physician, specialist, physical therapist, administration worker, social worker, or other hospital staff members associated with the patient. This allows a user to have easy access to important contact information without having to manually add and remove each entry from the organizer program of caregiver receiver 60 (FIG. 1).

Figure 16:
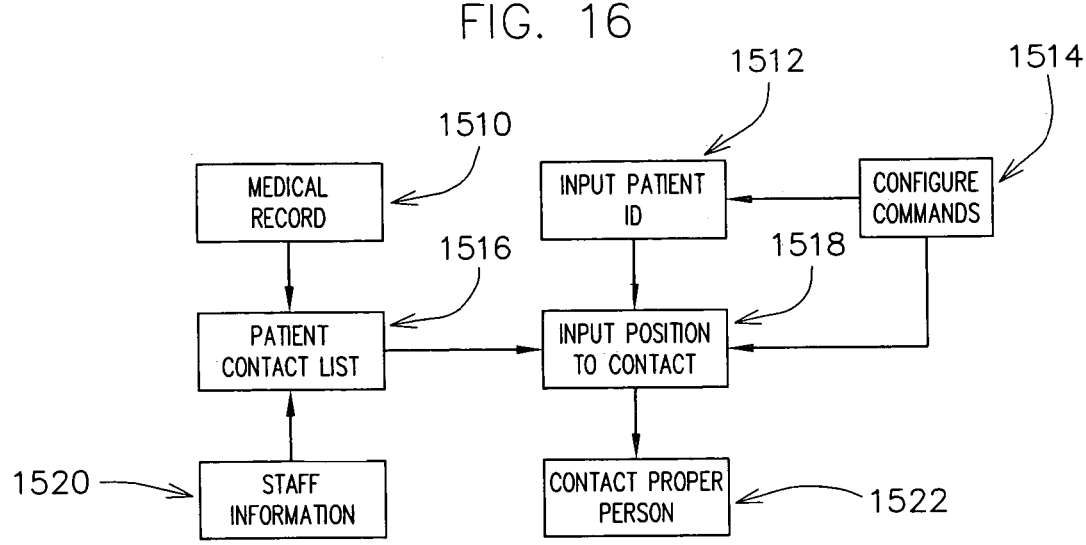
FIG. 16 is a flow chart of a phone and contact function according to one embodiment which may be used in conjunction with the embodiment of FIGS. 15 and 16.

Referring to FIG. 16, a method for initiating a call in a health care facility using a caregiver receiver or other portable electronic communication device includes receiving information at block 1512 regarding a patients identification (name, room number, nickname, hospital ID number, etc.). The information may be an audible input from a user in a voice-dialing system, or may be based on some other input.

Once a patient has been identified, the system may be configured to receive information at block 1518 relating to a person based on their relationship to the patient, based on their name, and/or based on some other factor. For instance, possible inputs include primary physician, treating physician, specialist, physical therapist, administration worker, social worker, or other hospital staff members associated With the patient. Other possible inputs include husband, wife, contact person, attorney, and other common contacts.

Based on the input received at block 1518, a voice connection may be established with the appropriate person at block 1522. This may be done in a manner similar to that described above with respect to blocks 1216-1220 of FIG. 13.

The data used to identify the proper contact person at block 1518 may be customized based on a patient contact list from block 1516. The patient contact list can, in turn, be based on information from a patient medical record entered at block 1510 and a hospital staff information list at block 1520. Information obtained from the medical record at block 1520 may include primary physician, husband, wife, contact person, pharmacist, attorney, treating physician, specialist, physical therapist, administration worker, social worker, other hospital staff members associated with the patient, and other common contacts. Information obtained from the staff information list at block 1520 may include treating physician, specialist, physical therapist, administration worker, social worker, or other hospital staff members associated with the patient.

The list at block 1520 may he updated based on time of day and on shift changes such that a caregiver who is available may be contacted. For instance, during the day the specialist who treated the patient may be contacted but at night, the specialist who is on call would be contacted first. This may be true of any other position where a person is listed as on-call. Also, a primary physician may be contacted directly during normal business hours for the physician, but the physician's calling service may be contacted at other times. Also, one administration staff person may be in charge of the patient during one shift and another administration staff person may be in charge during a different shift. The person contacted may be configured to change with the shift change. This may be true of other positions that are subject to shift changes and common assignment responsibilities.

The patient contact list at block 1516 may be updated such that when a user views their patient's contacts on caregiver receiver 60 (FIG. 1) or places a call using caregiver receiver 60, the user may rely on the updated information.

The inputs received at block 1518 need not be a keyword, but may instead be based on a phrase uttered by the user. The system may be configured to scan the user input for keywords that it may piece together to give the user options. The system may use techniques such as word matching and word spotting to analyze the user input.

Also, the system may receive at block 1518 a person's name to be contacted (such as a particular doctor's name), may recognize that the person (doctor) is not available, and may suggest alternate suggestions which may be other people listed by name and/or position (such as listing other doctors in the particular doctor's group, listing other doctors who have the same specialty as the particular doctor, and/or listing the doctor on call who is responsible for the particular doctor's patients).

The system may also be configured at block 1516 to initially associate certain position keywords (such as lab technician) with a generic phone number and then re-associate that position keyword with a particular person when that particular person takes responsibility for a task associated with the patient (such as processing and/or analyzing lab results).

While FIGS. 13 to 16 have been described with respect to a patient monitoring system, novel aspects of the embodiments described with respect to those figures may be incorporated in other systems—especially other monitoring or communication systems. Also, these figures show exemplary embodiments only and it should be understood that the order of some of the blocks may be rearranged without departing from the scope of an appended claim.

Figure 17:
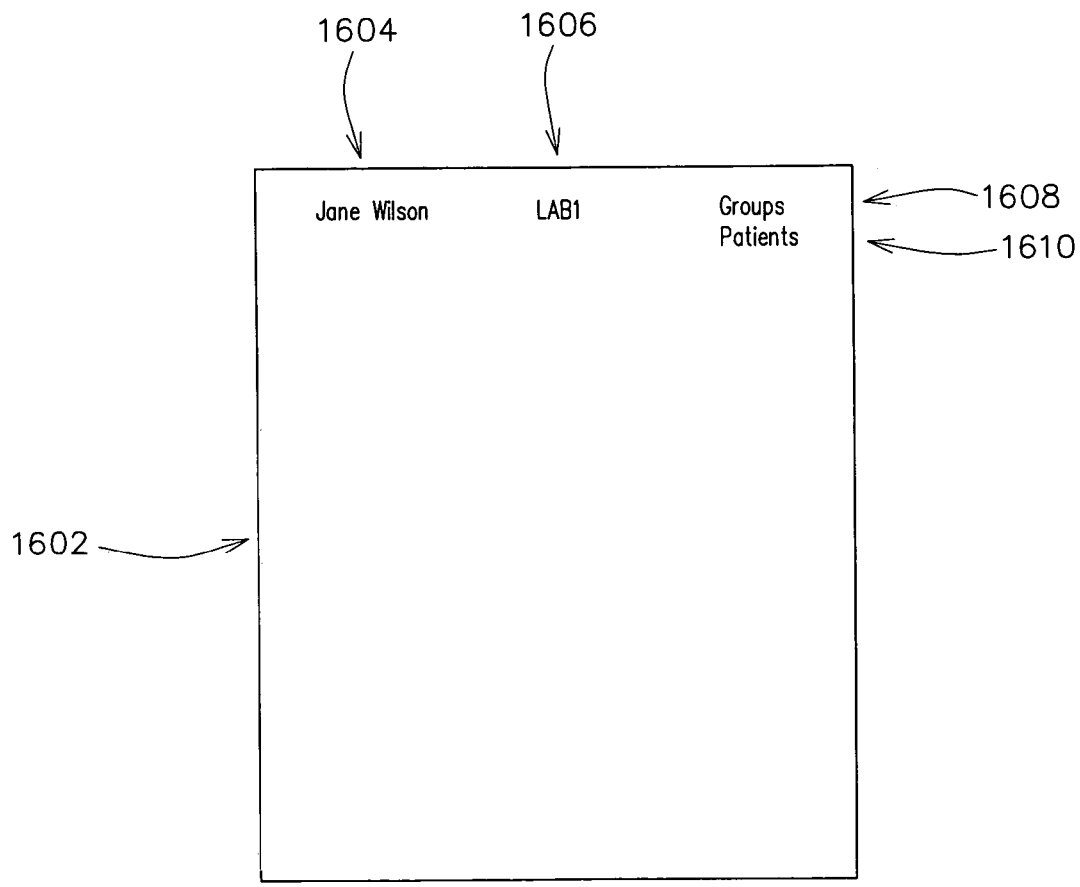
FIG. 17 is a control/display screen according to one embodiment of a notification system which is part of a monitoring system that monitors a plurality of patients, which screen may be implemented on a portable electronic device.

Referring to FIG. 17, a user interface 1602 of a caregiver receiver 60 may include a name 1604 and a care unit ID 1606 of the caregiver profile associated with caregiver receiver 60. This may allow a user to determine that the caregiver receiver is associated with the appropriate caregiver profile of the notification system 64. Actuating a control associated with name 1604 and/or care unit ID 1606 (e.g. tapping a touch screen or highlighting an area of user interface followed by actuation of a button) may allow a user to edit the profile of the caregiver associated with caregiver receiver 60, such as was described with respect to FIG. 11C above.

User interface 1602 may also include a groups option 1608 and/or a p patients option 1610 which allow a user to view the groups and/or patients with which they are associated. Actuation of one of options 1608 and 1610 may alternatively be used to edit the patients and/or groups with which the caregiver profile displayed on the caregiver receiver 60 is associated, such as was described with respect to FIGS. 11D and 11E above.

The invention has been described with reference to various specific and illustrative embodiments and techniques. However, it should be understood that many variations and modifications may be made while remaining within the spirit and scope of the invention.

For instance, while the various systems, devices, programs, and methods have been described with respect to a patient monitoring system, novel aspects of the embodiments described may be incorporated in other systems—especially other monitoring or communication systems. Also, the description is made with respect to exemplary embodiments only and it should be understood that the arrangement of many of the method blocks and system, device, and program components may be changed without departing from the scope of an appended claim. Also, it should be understood that in alternate embodiments claimed in the claims, many of the components described with respect to the exemplary embodiments may be withheld or may be replaced by equivalent structures.

What is claimed is:

1. A portable electronic device for use in a medical monitoring system, wherein the medical monitoring system generates notification messages indicating that a patient being monitored may have a condition that requires attention and wirelessly transfers the notification messages to the portable electronic device, the portable electronic device comprising:
   a processing circuit configured to receive the data associated with the notification messages;
   a first wireless transceiver coupled to the processing circuit and configured to receive data associated with the notification messages and transfer at least some of the data to the processing circuit, the first wireless transceiver configured to operate using a first wireless data transfer method;
   a second wireless transceiver coupled to the processing circuit and configured to receive data associated with the notification messages and transfer at least some of the data to the processing circuit, the second wireless transceiver configured to operate using a second wireless data transfer method different than the first wireless data transfer method; and
   a housing configured to house the processing circuit, and the first and second wireless transceivers.

2. The device of claim 1, wherein the first wireless data transfer method is a cellular data transfer method.

3. The device of claim 1, wherein the first wireless data transfer method is adapted to transfer data within a wireless local area network.

4. The device of claim 1, wherein the first wireless data transfer method comprises an IEEE 802.11 protocol.

5. The device of claim 4, wherein the second wireless data transfer method uses a cellular data transfer protocol.

6. The device of claim 1, wherein the processing circuit is configured to ascertain if data transfer is possible using the first wireless data transfer method.

7. The device of claim 6, wherein the processing circuit is configured to use the first wireless data transfer method if data transfer is possible using the first wireless data transfer method and to use the second wireless data transfer method if data transfer is not possible using the first wireless data transfer method.

8. The device of claim 1, wherein the processing circuit is configured to forward data received by the processing circuit using the first wireless transceiver and using the second wireless transceiver.

9. A method to be implemented by electronic devices of a medical monitoring system of a health care facility where a patient's physiological characteristics are being monitored for conditions that may require attention by a clinician, the method comprising:
   receiving data from a monitoring device configured to monitor a patient;
   determining whether the patient has a condition that may require attention based on the data received from the monitoring device;
   sending a notification message to a portable electronic device using a first wireless data transfer method if the patient has a condition that may require attention; and
   sending the notification message to the portable electronic device using a second wireless data transfer method different than the first wireless data transfer method if the patient has a condition that may require attention, wherein the portable electronic device is configured to receive the notification message in the first and second wireless data transfer method.

10. The method of claim 9, further comprising determining whether it is possible to transfer data to the portable electronic device using the first data transfer method.

11. The method of claim 10, wherein sending a notification message using the first wireless data transfer method and sending a notification message using the second wireless data transfer method comprises sending a particular notification message using only one of the first and second data transmission methods based on the determination whether it is possible to transfer data to the portable electronic device using the first data transfer method.

12. The method of claim 9, further comprising:
receiving a user input; and
transferring data associated with a notification message received by the portable electronic device using the first wireless data transfer method in response to the user input.

13. The device of claim 9, wherein the first wireless data transfer method is a cellular data transfer method.

14. The device of claim 9, wherein the first wireless data transfer method is adapted to transfer data within a wireless local area network.

15. The device of claim 9, wherein the first wireless data transfer method comprises an IEEE 802.11 protocol.

16. The device of claim 15, wherein the second wireless data transfer method uses a cellular data transfer protocol.

17. The method of claim 9, further comprising sending a notification message to the portable electronic device using a third wireless data transfer method different than the first wireless data transfer method and the second wireless data transfer method if the patient has a condition that may require attention.

18. The method of claim 17, wherein
the first wireless data transfer method comprises a cellular data transfer protocol; and
the second wireless data transfer method comprises a IEEE 802.11 data transfer protocol.

19. The method of claim 18, wherein the third wireless data transfer method comprises a Bluetooth data transfer protocol.

20. The method of claim 9, wherein the portable electronic device has a volume of no more than about 30 cubic inches.

21. A method to be implemented by electronic devices of a medical monitoring system of a health care facility where a patient's physiological characteristics are being monitored for conditions that may require attention by a clinician, the method comprising:
receiving data from a monitoring device configured to monitor a patient;
determining whether the patient has a condition that may require attention based on the data received from the monitoring device;
sending a notification message to a first portable electronic device using a first wireless data transfer method if the patient has a condition that may require attention;
sending the notification message to a second portable electronic device using a second wireless data transfer method if the patient has a condition that may require attention;
receiving a user input from a user input device; and
sending data associated with the notification message, which data was received by the first portable electronic device, to a second portable electronic device based on the user input, wherein the portable electronic device is configured to receive the notification message in the first and second wireless data transfer method.

22. The method of claim 2, wherein the first portable electronic device comprises the user input device.

23. The method of claim 21, wherein sending a notification message to a first portable electronic device using a wireless data transfer method comprises determining whether data transfer is available using a first wireless data transfer method and sending the notification message using only one of the first wireless data transfer method and the second wireless data transfer method based on whether data transfer is available using the first wireless data transfer method.

24. The method of claim 21, wherein the notification message comprises physiological data acquired from the patient.

25. The method of claim 21, wherein the data associated with the notification message comprises physiological data of the patient.

26. The method of claim 25, wherein the physiological data comprises waveform data.

27. The method of claim 26, wherein the waveform data comprises ECG waveform data.

28. The method of claim 21, wherein the portable electronic device has a volume of no more than about 30 cubic inches.

29. A method to be implemented by electronic devices of a medical monitoring system of a health care facility where a patient's physiological characteristics are being monitored for conditions that may require attention by a clinician, the method comprising:
receiving data from a monitoring device configured to monitor a patient;
determining whether the patient has a condition that may require attention based on the data received from the monitoring device;
sending a notification message to a first portable electronic device using a first wireless data transfer method if the patient has a condition that may require attention; and
sending the notification message to a second portable electronic device using a second wireless data transfer method different than the first wireless data transfer method, wherein the portable electronic device is configured to receive the notification message in the first and second wireless data transfer method.

30. The method of claim 29, further comprising receiving a user input from a user input device of the first portable electronic device and sending data which had been displayed on the first portable electronic device and which is associated with a notification message to the second portable electronic device in response to the user input.

31. The method of claim 29, further comprising
receiving a user input from a user input device of the second portable electronic device when voice communication has been established between the first portable electronic device and the second portable electronic device; and
sending data which had been displayed on the first portable electronic device and which is associated with a notification message to the second portable electronic device in response to the user input.

32. The method of claim 29, wherein the first wireless data transfer method is a cellular data transfer method.

33. The method of claim 29, wherein the first wireless data transfer method comprises an IEEE 802.11 protocol.

34. The method of claim 29, wherein the second wireless data transfer method uses a cellular data transfer protocol.

35. A portable electronic device for use in a medical monitoring system that generates notification messages indicating that a patient being monitored may have a condition that requires attention and wirelessly transfers the notification messages to the portable electronic device, the portable electronic device comprising:

a processing circuit configured to receive the notification messages indicating that the patient being monitored may have a condition that requires attention;

a first radio frequency wireless transceiver coupled to the processing circuit and configured to receive data associated with the notification message, the first wireless transceiver configured to operate using a first wireless data transfer method;

a second radio frequency wireless transceiver coupled to the processing circuit and configured to receive data associated with the notification message, the second wireless transceiver configured to operate using a second wireless data transfer method different than the first wireless data transfer method; and a housing configured to house the processing circuit, the first radio frequency wireless transceiver and the second radio frequency transceiver.

36. The method of claim 35, further comprising receiving a user input from a user input device of the first portable electronic device and sending data which had been displayed on the first portable electronic device and which is associated with a notification message to the second portable electronic device in response to the user input.

37. A portable electronic device for use in a medical monitoring system that generates notification messages indicating that a patient being monitored may have a condition that requires attention and wirelessly transfers the notification messages to the portable electronic device, the portable electronic device comprising:

a processing circuit configured to receive the notification messages indicating that the patient being monitored may have a condition that requires attention;

a first wireless transceiver coupled to the processing circuit and configured to receive data associated with the notification message, the first wireless transceiver configured to operate using a cellular data transfer protocol;

a second wireless transceiver coupled to the processing circuit and configured to receive data associated with the notification message, the second wireless transceiver configured to using wireless local area network data transfer protocol; and a housing configured to house the processing circuit, the first wireless transceiver and the second wireless transceiver.

38. The device of claim 37, wherein the wireless local area network data transfer protocol is a IEEE 802.11 data transfer protocol.

39. A system for use in a medical monitoring system of a health care facility where a patient's physiological characteristics are being monitored for conditions that may require attention by a clinician, the system comprising:

a first processing circuit configured to receive data from a monitoring device configured to monitor a patient, and further configured to determine whether the patient has a condition that may require attention based on the data received from the monitoring device, and further configured to generate a control signal to send a notification message to a portable electronic device using a first wireless data transfer method if the patient has a condition that may require attention, and generate a control signal to send a notification message to the portable electronic device using a second wireless data transfer method different than the first wireless data transfer method if the patient has a condition that may require attention, wherein the protable electronic device includes a first transceiver using the first wireless data transfer method, a second transceiver using the second wireless data transfer method and a housing configured to house the first and second transceivers; and the portable electronic device comprising a second processing circuit configured to receive data from a wireless signal comprising a notification message.

40. The system of claim 39, wherein the portable electronic device has a volume of no more than about 30 cubic inches.

41. The system of claim 39, wherein the first processing circuit is further configured to determine whether it is possible to transfer data to the portable electronic device using the first data transfer method.

42. The system of claim 39, wherein the first processing circuit is configured to associate particular portable electronic devices with particular patients being monitored.

43. A method to be implemented by electronic devices of a medical monitoring system of a health care facility where a patient's physiological characteristics are being monitored for conditions that may require attention by a clinician, the method comprising:

receiving data from a monitoring device configured to monitor a patient;

determining whether the patient has a condition that may require attention based on the data received from the monitoring device;

generating a notification message based on the determination that the patient has a condition that may require attention;

determining whether data transfer to a caregiver receiver is possible using a first wireless data transfer method;

sending the notification message to the caregiver receiver using the first wireless data transfer method if the patient has a condition that may require attention and data transfer is possible using the first wireless data transfer method; and sending the notification message to the caregiver receiver using a second wireless data transfer method, different than the first wireless data transfer method, if the patient has a condition that may require attention and data transfer is not possible using the first wireless data transfer method, wherein the caregiver receives the notification with a portable electronic device configured to receive the notification in the first and second wireless data transfer methods;

wherein the first wireless data transfer method comprises using a local area network of the health care facility; and wherein the notification message comprises physiological data acquired from the patient, the physiological data comprising one of live physiological data acquired from the patient and a window of physiological data acquired from the patient at about the time of the alarm.

44. The method of claim 43, wherein the physiological data included in the notification message comprises ECG waveform data.

45. The method of claim 44, wherein the second wireless data transfer method comprises using a cellular network to transfer data associated with the notification message.

* * * * *